(12) United States Patent
Murata et al.

(10) Patent No.: US 9,324,951 B2
(45) Date of Patent: Apr. 26, 2016

(54) PYRAZINE DERIVATIVE, AND LIGHT EMITTING ELEMENT, DISPLAY DEVICE, ELECTRONIC DEVICE USING THE PYRAZINE DERIVATIVE

(71) Applicant: Semiconductor Energy Laboratory Co., Ltd., Kanagawa-ken (JP)

(72) Inventors: Hiroko Murata, Kanagawa (JP); Masakazu Egawa, Tochigi (JP); Harue Nakashima, Kanagawa (JP); Sachiko Kawakami, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 14/584,311

(22) Filed: Dec. 29, 2014

(65) Prior Publication Data

US 2015/0112065 A1 Apr. 23, 2015

Related U.S. Application Data

(63) Continuation of application No. 11/645,286, filed on Dec. 22, 2006, now Pat. No. 8,920,941.

(30) Foreign Application Priority Data

Dec. 28, 2005 (JP) ................................. 2005-378811

(51) Int. Cl.
*H01L 51/00* (2006.01)
*C07D 241/12* (2006.01)
(Continued)

(52) U.S. Cl.
CPC .......... *H01L 51/0067* (2013.01); *C07D 241/12* (2013.01); *C07D 403/12* (2013.01);
(Continued)

(58) Field of Classification Search
None
See application file for complete search history.

(56) References Cited

U.S. PATENT DOCUMENTS

| 5,077,142 A | 12/1991 | Sakon et al. |
| 5,405,709 A | 4/1995 | Littman et al. |

(Continued)

FOREIGN PATENT DOCUMENTS

| EP | 1 029 909 A1 | 8/2000 |
| EP | 1 616 864 A1 | 1/2006 |

(Continued)

OTHER PUBLICATIONS

Yamagami, C. et al., "Measurement and Prediction of Hydrophobicity Parameters for Highly Lipophilic Compounds: Application of the HPLC Column-Switching Technique to Measurement of log P of Diarylpyrazines," Journal of Pharmaceutical Sciences, Oct. 22, 1999, vol. 88, No. 12, pp. 1299-1304.

(Continued)

*Primary Examiner* — J. L. Yang
(74) *Attorney, Agent, or Firm* — Husch Blackwell LLP

(57) ABSTRACT

It is an object to provide a novel material having a bipolar property, a light emitting element provided with the novel material, and a display device that includes the light emitting element. It is an object to provide a pyrazine derivative represented by the following general formula (g-1).

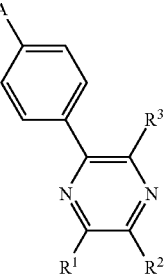

(g-1)

8 Claims, 52 Drawing Sheets

(51) Int. Cl.
   *C07D 403/12* (2006.01)
   *C07D 403/14* (2006.01)
   *C09K 11/06* (2006.01)
   *H05B 33/14* (2006.01)
   *H01L 51/50* (2006.01)

(52) U.S. Cl.
   CPC ............. *C07D403/14* (2013.01); *C09K 11/06* (2013.01); *H01L 51/0061* (2013.01); *H05B 33/14* (2013.01); *C09K 2211/1011* (2013.01); *C09K 2211/1014* (2013.01); *C09K 2211/1029* (2013.01); *C09K 2211/1044* (2013.01); *C09K 2211/185* (2013.01); *H01L 51/0071* (2013.01); *H01L 51/0072* (2013.01); *H01L 51/5012* (2013.01); *H01L 51/5016* (2013.01); *Y10S 428/917* (2013.01); *Y10T 428/265* (2015.01); *Y10T 428/31504* (2015.04)

(56) References Cited

U.S. PATENT DOCUMENTS

| | | | | |
|---|---|---|---|---|
| 5,430,123 | A * | 7/1995 | Kvakovszky et al. | ........ 528/172 |
| 6,004,685 | A | 12/1999 | Antoniadis | |
| 6,091,078 | A | 7/2000 | Codama | |
| 6,541,129 | B1 | 4/2003 | Kawamura et al. | |
| 7,399,537 | B2 | 7/2008 | Kawamura et al. | |
| 7,601,435 | B2 | 10/2009 | Shitagaki et al. | |
| 2003/0143430 | A1 | 7/2003 | Kawamura et al. | |
| 2004/0259453 | A1 | 12/2004 | Fukunaga et al. | |
| 2005/0233166 | A1 | 10/2005 | Ricks et al. | |
| 2007/0080628 | A1 | 4/2007 | Schafer et al. | |
| 2008/0241591 | A1 | 10/2008 | Kawamura et al. | |
| 2010/0069636 | A1 | 3/2010 | Shitagaki et al. | |

FOREIGN PATENT DOCUMENTS

| | | | |
|---|---|---|---|
| JP | 62-201446 A | | 9/1987 |
| JP | 02-072370 A | | 3/1990 |
| JP | 09-188875 A | | 7/1997 |
| JP | 09-249876 A | | 9/1997 |
| JP | 2000-309566 A | | 11/2000 |
| JP | 2004-355898 A | | 12/2004 |
| JP | 2005-170851 A | | 6/2005 |
| WO | WO 2004/094389 A1 | | 11/2004 |
| WO | WO 2005/053048 A1 | | 6/2005 |

OTHER PUBLICATIONS

Broser, W. et al., "Darstellung Von Tetraaryl-Pyrrolen Und Vergleichende Epr-g-Faktor-Untersuchung Von Pyrryl-Radikalen Mit Tetracyclon-Ketylen," Tetrahedron, 1973, vol. 29, No. 23, pp. 3959-3971.

Gelmi, M.L. et al., "5(4H)-Oxazolones. Part X.1 Acid and Base Effects on the Translactonization Reaction of 4-(2-Oxa-alkylidene)-5(4H)-oxazolones: New Synthesis of 5-Alkylidene-3-benzoylamino-2(5H)-furanones," Tetrahedron, 1997, vol. 53, No. 5, pp. 1843-1854.

Thomas, K.R.J. et al., "Quinoxalines Incorporating Triarylamines: Potential Electroluminescent Materials With Tunable Emission Characteristics," Chemistry of Materials, 2002, vol. 14, No. 6, pp. 2796-2802.

Gao, B. et al., "New Fluorescent Dipolar Pyrazine Derivatives for Non-Doped Red Organic Light-Emitting Diodes," Materials Chemistry and Physics, Oct. 10, 2006, vol. 99, pp. 247-252.

* cited by examiner

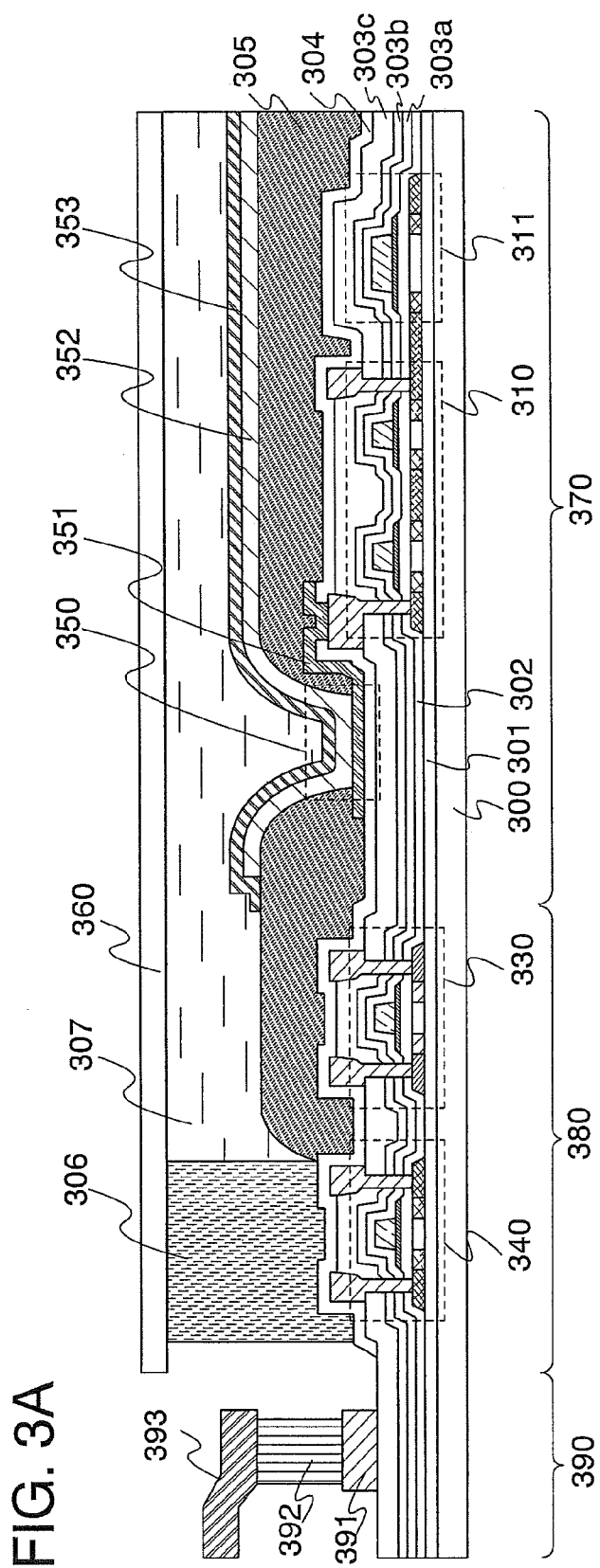
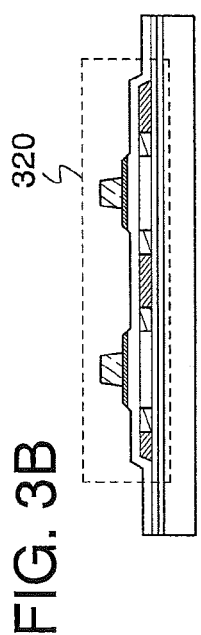
FIG. 3A
FIG. 3B

PYRAZINE DERIVATIVE, AND LIGHT EMITTING ELEMENT, DISPLAY DEVICE, ELECTRONIC DEVICE USING THE PYRAZINE DERIVATIVE

This application is a continuation of copending U.S. application Ser. No. 11/645,286, filed on Dec. 22, 2006 which is incorporated herein by reference.

BACKGROUND OF THE INVENTION

1. Field of the Invention

The present invention relates to a pyrazine derivative. The present invention also relates to a light emitting element containing the pyrazine derivative and a display device that includes a light emitting element containing the pyrazine derivative.

2. Description of the Related Art

In recent years, a light emitting element using a light emitting compound has been attracted attention as a display (a display device) of the next generation because it has a feature of low power consumption and a lightweight and thin type. In addition, the light emitting element using a light emitting compound is a self-luminous type; accordingly, it is considered that the light emitting element using a light emitting compound has superiority in visibility without problems such as a viewing angle as compared with a liquid crystal display (an LCD).

A basic structure of a light emitting element is a structure that has a light emitting layer containing a light emitting compound interposed between a pair of electrodes. It is said that, in such a light emitting element, by applying a voltage, holes injected from an anode and electrons injected from a cathode are recombined in an emission center of a light emitting layer to excite a molecule, and the excited molecule discharge energy in returning to a ground state; accordingly light is emitted. It is to be noted that an excited state that is generated by recombination has a singlet excited state and a triplet excited state. Light emission is considered to be possible through a singlet excited state and a triplet excited state. In particular, light emission in a case of returning from the singlet excited state to the ground state directly is defined as fluorescence, and light emission in a case of returning from the triplet excited state to the ground state is defined as phosphorescence.

It is considered that the singlet excited state and the triplet excited state, which are an excited state, are generated at a ratio of 1:3 statistically. Accordingly, when phosphorescence that is light emission in a case of returning from the triplet excited state to the ground state is used, it is theoretically considered that a light emitting element having internal quantum efficiency (a ratio of photon that is generated with respect to injected carriers) of 75 to 100% can be obtained. That is to say, if phosphorescence can be utilized, light emitting efficiency can be remarkably improved as compared with utilizing fluorescence.

However, phosphorescence can not be observed at a room temperature in a general organic compound. This is because that the ground state of an organic compound is ordinarily in the singlet ground state, and transition from the triplet excited state to the singlet ground state becomes forbidden transition. On the other hand, transition from the singlet excited state to the singlet ground state becomes allowed transition, and therefore, fluorescence can be observed. However, in recent years, a compound capable of emitting phosphorescence, in other words, a compound capable of converting light in returning from the triplet excited state to the ground state into light emission (hereinafter, referred to as a phosphorescent compound) is discovered as shown in Patent Document 1, and it has been actively researched (for example, see Patent Document 1: Japanese Published Patent Application No. 2005-170851).

When a light emitting element is manufactured using a phosphorescent compound, the phosphorescent compound is used in a state where the phosphorescent compound is dispersed in a host material in order to prevent decrease of light emitting efficiency due to concentration quenching. Therefore, in order to efficiently obtain light emission from the phosphorescent compound, selection of the host material becomes important.

In order to efficiently obtain light emission from the phosphorescent compound, it is found that a host material having a bipolar property is suitable. However, many of organic compounds are a material having a monopolar property, which has either a hole transporting property or an electron transporting property. Therefore, a material having a bipolar property, which has both the hole transporting property and the electron transporting property, is required to be developed.

SUMMARY OF THE INVENTION

Consequently, it is an object of the present invention to provide a novel material having a bipolar property, a light emitting element provided with the novel material, and a display device that includes the light emitting element.

In addition, it is also an object of the present invention to provide a novel material having a bipolar property, which can be used as a host material for dispersing a light emitting compound. In particular, it is an object of the present invention to provide a novel material having a bipolar property, which can be used as a host material for dispersing a phosphorescent compound.

Moreover, it is an object of the present invention to provide a novel material having a bipolar property, which can be used as a light emitting compound.

One aspect of the present invention is a pyrazine derivative represented by the following general formula (g-1).

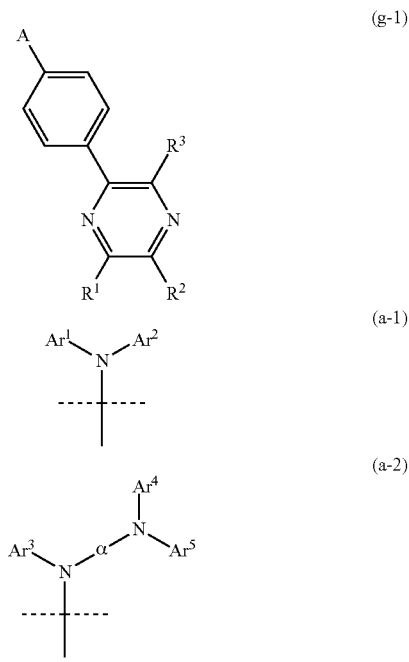

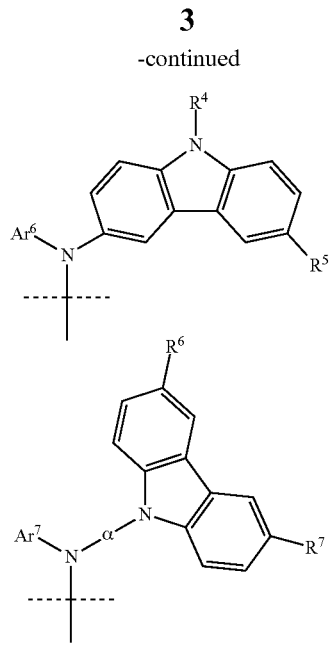

In the above general formula (g-1), each of $R^1$, $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Further, A in the formula represents a substituent represented by any of a general formula (a-1), a general formula (a-2), a general formula (a-3), and a general formula (a-4). $R^4$ in the formula represents an alkyl group having greater than or equal to 1 and less than or equal to 4 carbon atoms or an aryl group having greater than or equal to 6 and less than or equal to 25 carbon atoms. Each of $R^5$, $R^6$, and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $Ar^1$, $Ar^2$, $Ar^3$, $Ar^4$, $Ar^5$, $Ar^6$, and $Ar^7$ may be same or different, and represents an aryl group having greater than or equal to 6 and less than or equal to 25 carbon atoms. Further, α represents an arylene group having greater than or equal to 6 and less than equal to 25 carbon atoms. It is to be noted that the aryl group may have a substituent or be unsubstituted. Further, the arylene group may have a substituent or be unsubstituted.

Another aspect of the present invention is a pyrazine derivative represented by the following general formula (g-2).

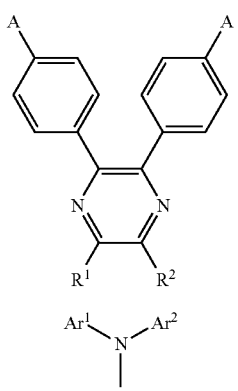

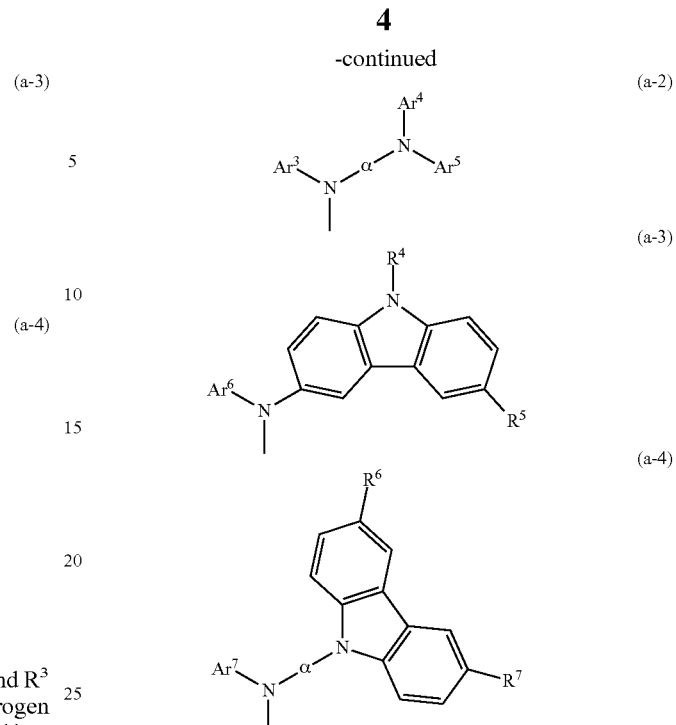

In the above general formula (g-2), each or $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Further, A in the formula represents a substituent represented by any of a general formula (a-1), a general formula (a-2), a general formula (a-3), and a general formula (a-4). $R^4$ in the formula represents an alkyl group having greater than or equal to 1 and less than or equal to 4 carbon atoms or an aryl group having greater than or equal to 6 and less than or equal to 25 carbon atoms. Each of $R^5$, $R^6$, and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $Ar^1$, $Ar^2$, $Ar^3$, $Ar^4$, $Ar^5$, $Ar^6$, and $Ar^7$ in the formula may be same or different, and represents an aryl group having greater than or equal to 6 and less than or equal to 25 carbon atoms. Further, α represents an arylene group having greater than or equal to 6 and less than equal to 25 carbon atoms. It is to be noted that the aryl group may have a substituent or be unsubstituted. Further, the arylene group may have a substituent or be unsubstituted.

Another aspect of the present invention is a pyrazine derivative represented by the following general formula (g-3).

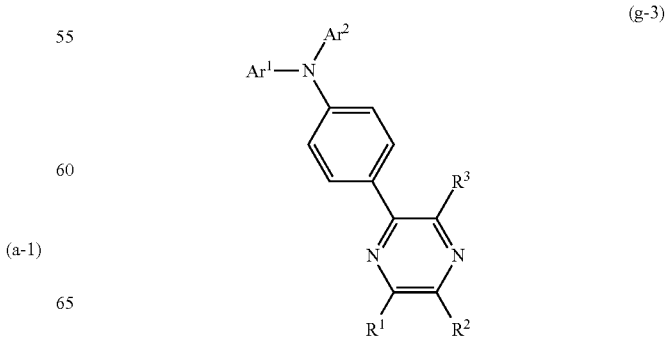

In the above general formula (g-3), each of $R^1$, $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. It is to be noted that the aryl group may have a substitute and be unsubstituted. Further, each of $Ar^1$ and $Ar^2$ may be same or different, and represents any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group.

Another aspect of the present invention is a pyrazine derivative represented by the following general formula (g-4).

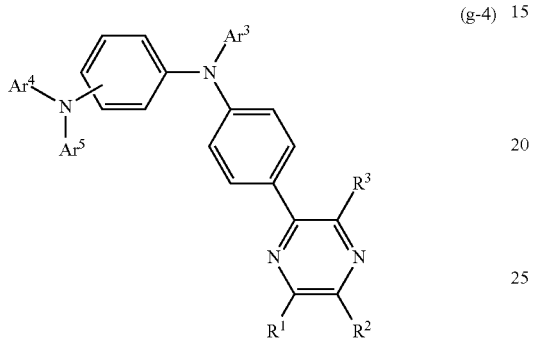

(g-4)

In the above formula (g-4), each or $R^1$, $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Further, each of $Ar^3$, $Ar^4$, and $Ar^{y}$ may be same or different, and represents an aryl group having greater than or equal to 6 and less than or equal to 25 carbon atoms. It is to be noted that the aryl group may have a substituent or be unsubstituted.

Another aspect of the present invention is a pyrazine derivative represented by the following general formula (g-5).

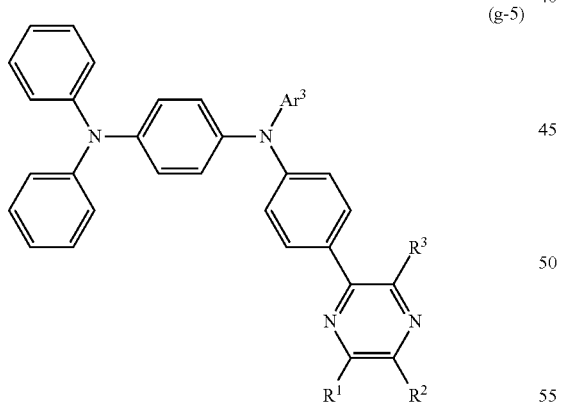

(g-5)

In the above general formula (g-5), each or $R^1$, $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Further, $Ar^3$ represents an aryl group having greater than or equal to 6 and less than or equal to 25 carbon atoms. It is to be noted that the aryl group may have a substituent or be unsubstituted.

Furthermore, in the above general formula (g-5), the $Ar^3$ is preferably any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group.

Another aspect of the present invention is a pyrazine derivative represented by the following general formula (g-6).

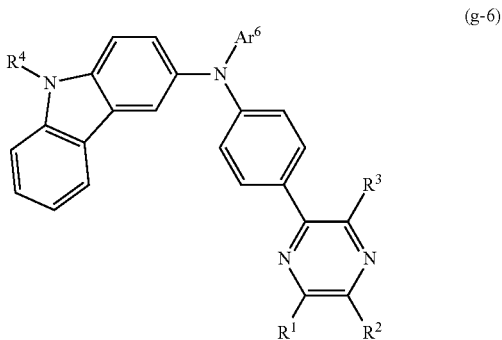

(g-6)

In the above general formula (g-6), each or $R^1$, $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $R^4$ represents an alkyl group having greater than or equal to 1 and less than or equal to 4 carbon atoms or an aryl group having greater than or equal to 6 and less than or equal to 25 carbon atoms. $Ar^6$ represents any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group. It is to be noted that the aryl group may have a substituent or be unsubstituted.

Another aspect of the present invention is a pyrazine derivative represented by the following general formula (g-7).

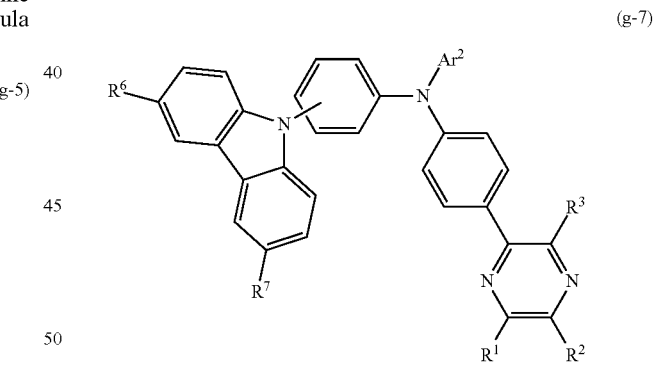

(g-7)

In the above general formula (g-7), each or $R^1$, $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $R^6$ and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $Ar^7$ represents an aryl group having greater than or equal to 6 and less than or equal to 25 carbon atoms. It is to be noted that the aryl group may have a substituent or be unsubstituted.

Another aspect of the present invention is a pyrazine derivative represented by the following general formula (g-8).

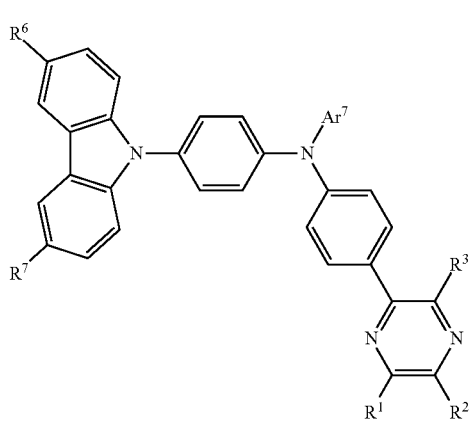

(g-8)

In the above general formula (g-8), each or $R^1$, $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $R^6$ and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $Ar^7$ represents an aryl group. It is to be noted that the aryl group may have a substituent or be unsubstituted.

Further, in the above general formula (g-8), $Ar^7$ is preferably any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group.

Another aspect of the present invention is a pyrazine derivative represented by the following general formula (g-9).

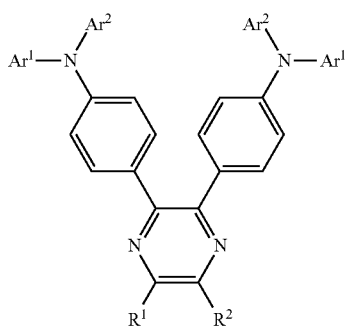

(g-9)

In the above general formula (g-9), each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $Ar^1$ and $Ar^2$ may be same or different, and represents any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group. It is to be noted that the aryl group may have a substituent or be unsubstituted.

Another aspect of the present invention is a pyrazine derivative represented by the following general formula (g-10).

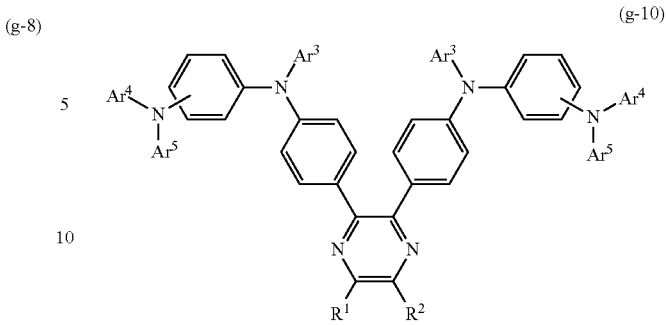

(g-10)

In the above general formula (g-10), each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $Ar^3$, $Ar^4$, and $Ar^5$ may be same or different, and represents an aryl group having greater than or equal to 6 and less than or equal to 25 carbon atoms. It is to be noted that the aryl group may have a substituent or be unsubstituted.

Another aspect of the present invention is a pyrazine derivative represented by the following general formula (g-11).

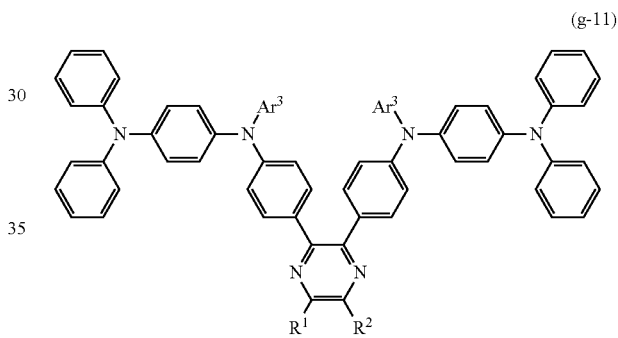

(g-11)

In the above general formula (g-11), each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $Ar^3$ represents an aryl group having greater than or equal to 6 and less than or equal to 25 carbon atoms. It is to be noted that the aryl group may have a substituent or be unsubstituted.

Further, in the above general formula (g-11), $Ar^3$ is preferably any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group.

Another aspect of the present invention is a pyrazine derivative represented by the general formula (g-12).

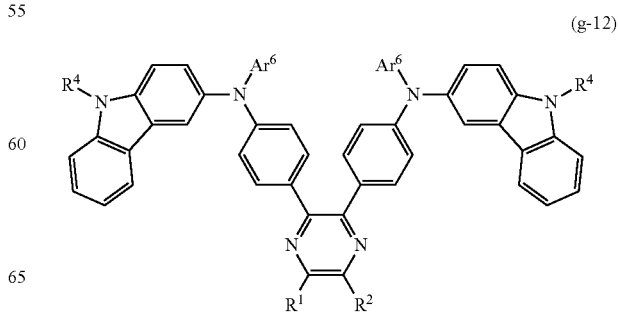

(g-12)

In the above general formula (g-12), each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $R^4$ represents an alkyl group having greater than or equal to 1 and less than or equal to 4 carbon atoms or an aryl group having greater than or equal to 6 and less than or equal to 25 carbon atoms. $Ar^6$ represents any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group. It is to be noted that the aryl group may have a substituent or be unsubstituted.

Another aspect of the present invention is a pyrazine derivative represented by the following general formula (g-13).

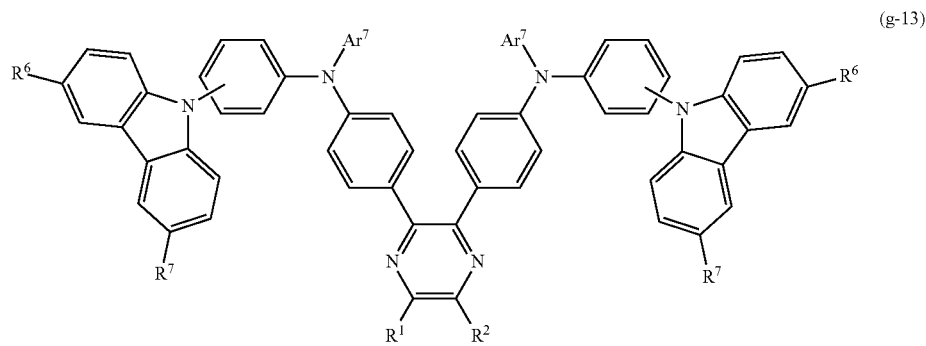

(g-13)

In the above general formula (g-13), each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $R^6$ and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $Ar^7$ represents an aryl group having greater than or equal to 6 and less than equal to 25 carbon atoms. It is to be noted that the aryl group may have a substituent or be unsubstituted.

Another aspect of the present invention is a pyrazine derivative represented by the following general formula (g-14).

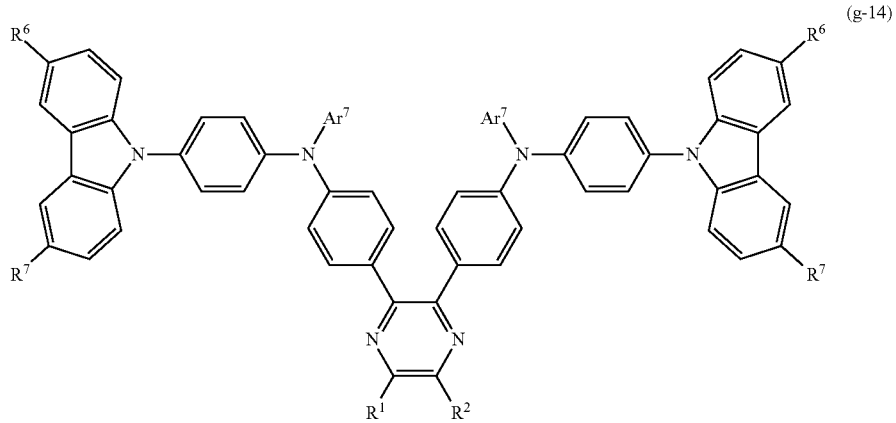

(g-14)

In the above general formula (g-14), each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $R^6$ and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $Ar^7$ represents an aryl group having greater than or equal to 6 and less than equal to 25 carbon atoms. It is to be noted that the aryl group may have a substituent or be unsubstituted.

Further, in the above general formula, $Ar^7$ is preferably any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group.

Another aspect of the present invention is a light emitting element that includes a layer containing a pyrazine derivative described in any one of the above general formulas (g-1) to (g-14) between a pair of electrodes.

Another aspect of the present invention is a light emitting element that includes a layer containing a pyrazine derivative described in any one of the above general formulas (g-1) to (g-14) and a light emitting compound between a pair of electrodes.

Another aspect of the present invention is a light emitting element that includes a layer containing a pyrazine derivative described in any one of the above general formulas (g-1) to (g-14) and a phosphorescent compound between a pair of electrodes. It is to be noted that the phosphorescent compound indicates a compound capable of discharging phosphorescence, in other words, a compound capable of converting light that is emitted in returning from a triplet excited state to a ground state into light emission.

Another aspect of the present invention is a display device that includes a light emitting element containing a pyrazine derivative described in any one of the above general formulas (g-1) to (g-14).

Another aspect of the present invention is a display device that includes a light emitting element containing a pyrazine derivative described in any one of the above general formulas (g-1) to (g-14) and a phosphorescent compound.

Another aspect of the present invention is an electronic device that includes a light emitting element containing a pyrazine derivative described in any one of the above general formulas (g-1) to (g-14).

Another aspect of the present invention is an electronic device that includes a light emitting element containing a pyrazine derivative described in any one of the above general formulas (g-1) to (g-14) and a phosphorescent compound.

A pyrazine derivative of the present invention is a pyrazine derivative having a bipolar property and superiority in both an electron transporting property and a hole transporting property.

A pyrazine derivative of the present invention is a pyrazine derivative that is stable to electrochemical oxidization or reduction.

A pyrazine derivative of the present invention is a light emitting compound having a bipolar property and superiority in both an electron transporting property and a hole transporting property.

By dispersing a phosphorescent compound in a layer made of a pyrazine derivative of the present invention, a light emitting element having extremely high light emitting efficiency can be obtained.

BRIEF DESCRIPTION OF DRAWINGS

FIGS. 3A and 3B are views each showing an example of a display device of the present invention.

DETAILED DESCRIPTION OF THE INVENTION

Embodiment Mode 1

Figure 1:
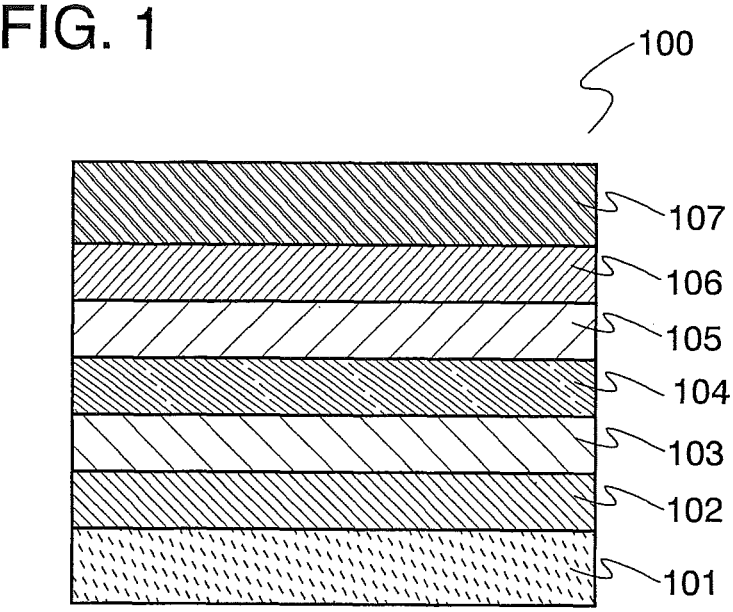
FIG. 1 is a view showing an example of a light emitting element of the present invention.

In this embodiment mode, a pyrazine derivative of the present invention will be explained.

A pyrazine derivative of the present invention is represented by the following general formula (g-1).

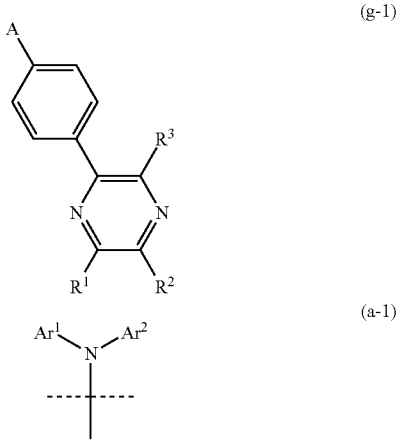

(g-1)

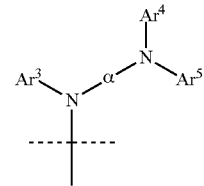

(a-2)

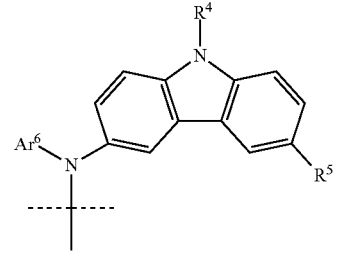

(a-3)

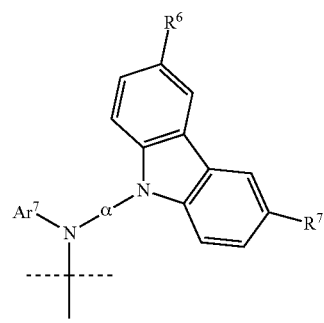

(a-4)

In the above general formula (g-1), each of $R^1$, $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Further, A in the formula represents a substitutent represented by any of a general formula (a-1), a general formula (a-2), a general formula (a-3), and a general formula (a-4). $R^4$ in the formula represents an alkyl group having greater than or equal to 1 and less than or equal to 4 carbon atoms or an aryl group having greater than or equal to 6 and less than or equal to 25 carbon atoms. Each of $R^5$, $R^6$, and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $Ar^1$ to $Ar^7$ may be same or different, and represents an aryl group having greater than or equal to 6 and less than or equal to 25 carbon atoms. Further, α represents an arylene group represents having greater than or equal to 6 and less than or equal to 25 carbon atoms. It is to be noted that the aryl group in the formula may have a substituent or be unsubstituted. In a similar manner, the arylene group may have a substituent or be unsubstituted.

Further, in the above general formula (g-1), as a specific example of the alkyl group having greater than or equal to 1 and less than or equal to 4 carbon atoms, a methyl group, an ethyl group, an i-propyl group, an n-propyl group, an n-butyl group, a t-butyl group, an i-butyl group, an s-butyl group, or the like can be given. As a specific example of the aryl group having greater than or equal to 6 and less than or equal to 25 carbon atoms, a phenyl group, an o-tolyl group, a m-tolyl group, a p-tolyl group, a napthly group, a 2-naphthyl group, a 4-biphenyl group, a 3-biphenyl group, a 2-biphenyl group, a 9,9-methylfluorene-2-yl group, a spiro-9,9'-bifluorene-2-yl group, or the like can be given. As a specific example of the arylene group having greater than or equal to 6 and less than or equal to 25 carbon atoms, an o-phenylene group, a m-phenylene group, a p-phenylene group, a 1,5-naphthylene group, a 1,4-naphthylene group, a 9,9-dimethylfluorene-2,7-diyl group, a 4,4-biphenylene group, a spiro-9,9'-bifluorene-2,7-diyl group, or the like can be given.

Furthermore, in the above general formula (g-1), when A in the formula is the substituent represented by the general formula (a-1), and $Ar^1$ and $Ar^2$ are any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group, synthesis becomes easy, which is preferable in the present invention. In other words, the present invention is preferably a pyrazine derivative represented by the following general formula (g-3).

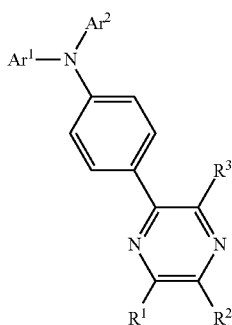

(g-3)

In the above general formula (g-3), each of $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. It is to be noted that the aryl group may have a substituent or be unsubstituted.

Further, in the above general formula (g-1), when A in the formula is the substituent represented by the general formula (a-4), and α is a phenylene group, much higher triplet excitation energy can be obtained, and chemical stability can be obtained, which is preferable in the present invention. In other words, the present invention is preferably a pyrazine derivative represented by the following general formula (g-4).

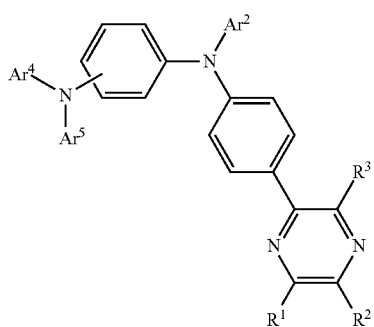

(g-4)

In the above general formula (g-4), each of $R^1$, $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $Ar^3$, $Ar^4$, and $Ar^5$ may be same or, different, and represents an aryl group having greater than or equal to 6 and less than or equal to 25 carbon atoms. It is to be noted that the aryl group may have a substituent or be unsubstituted.

Further, in the above general formula (g-1), when A in the formula is the substituent represented by the general formula (a-2), $Ar^4$ and $Ar^5$ are a phenyl group, and α is a 1,4-phenylene group, much higher triplet excitation energy can be obtained, and synthesis becomes easy, which is preferable in the present invention. In other words, the present invention is preferably a pyrazine derivative represented by the following formula (g-5).

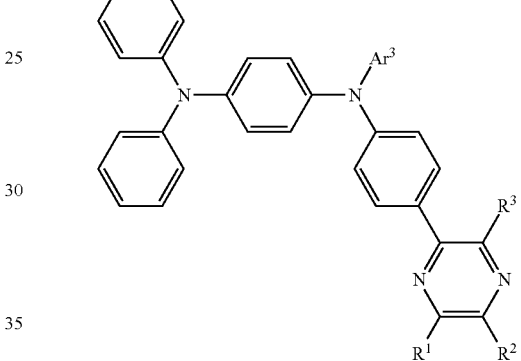

(g-5)

In the above general formula (g-5), each of $R^1$, $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $Ar^3$ represents an aryl group having greater than or equal to 6 and less than or equal to 25 carbon atoms. It is to be noted that the aryl group may have a substituent or be unsubstituted.

Further, in the above general formula (g-5), when $Ar^3$ in the formula is any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group, synthesis becomes easy, which is preferable in the present invention.

Furthermore, in the above general formula (g-1), when A in the formula is the substituent represented by the general formula (a-3), and $Ar^6$ is any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group, synthesis becomes easy, which is preferable in the present invention. In other words, the present invention is preferably a pyrazine derivative represented by the following general formula (g-6).

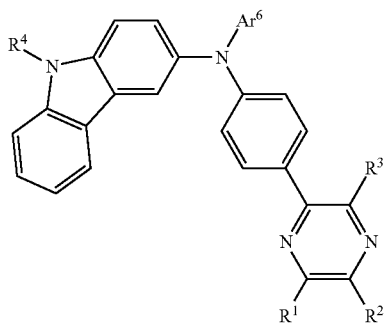
(g-6)

In the above general formula (g-6), each of $R^1$, $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $R^4$ represents an alkyl group having greater than or equal to 1 and less than or equal to 4 carbon atoms or an aryl group having greater than or equal to 6 and less than or equal to 25 carbon atoms. It is to be noted that the aryl group may have a substituent or be unsubstituted.

Further, in the above general formula (g-1), when A in the formula is the substituent represented by the general formula (a-4), and α is a phenylene group, much higher triplet excitation energy can be obtained, and chemical stability can be obtained, which is preferable in the present invention. In other words, the present invention is preferably a pyrazine derivative represented by the following general formula (g-7).

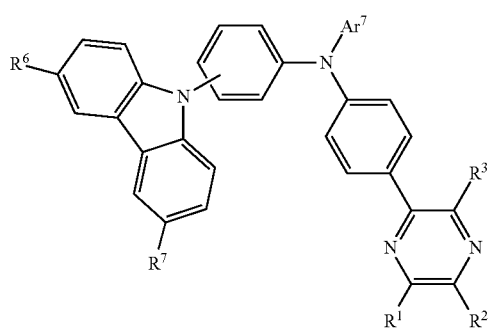
(g-7)

In the above general formula (g-7), each of $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $R^6$ and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $Ar^7$ represents an aryl group having greater than or equal to 6 and less than or equal to 25 carbon atoms. It is to be noted that the aryl group may have a substituent or be unsubstituted.

Further, in the above general formula (g-1), when A in the formula is the substituent represented by the general formula (a-4), and α is a 1,4-phenylene group, much higher triplet excitation energy can be obtained, and chemical stability can be obtained, which is preferable in the present invention. In other words, the present invention is preferably a pyrazine derivative represented by the following general formula (g-8).

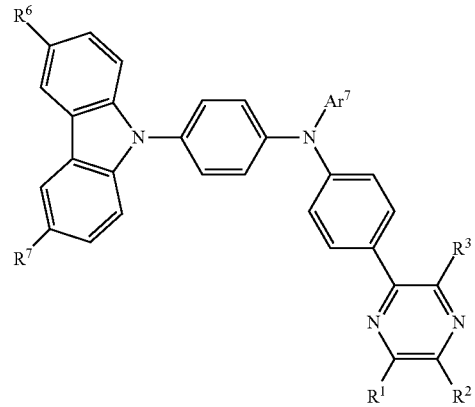
(g-8)

In the above general formula (g-8), each of $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $R^6$ and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $Ar^7$ represents an aryl group. It is to be noted that the aryl group may have a substituent or be unsubstituted.

Further, in the above general formula (g-8), when $Ar^7$ in the formula is any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group, synthesis becomes easy, which is preferable in the present invention.

In addition, a pyrazine derivative of the present invention is represented by the following general formula (g-2).

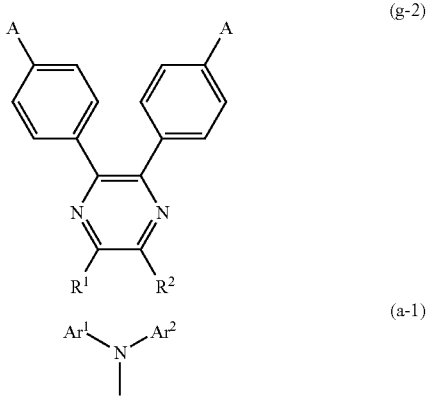
(g-2)

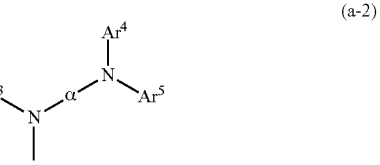
(a-1)

(a-2)

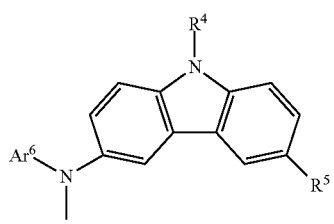

(a-3)

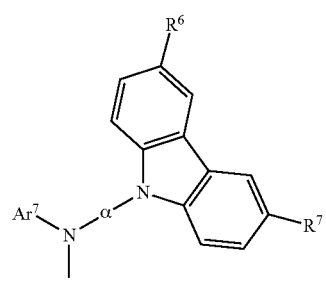

(a-4)

In the above general formula (g-2), each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. It is to be noted that the aryl group in the formula may have a substituent or be unsubstituted. Further, A in the formula represents a substituent represented by any of a general formula (a-1), a general formula (a-2), a general formula (a-3), and a general formula (a-4). $R^4$ in the formula represents an alkyl group having greater than or equal to 1 and less than or equal to 4 carbon atoms or an aryl group having greater than or equal to 6 and less than or equal to 25 carbon atoms. Each of $R^5$, $R^6$, and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. It is to be noted that the aryl group may have a substituent or be unsubstituted. Each of $Ar^1$ to $Ar^7$ in the formula may be same or different, and represents an aryl group having greater than or equal to 6 and less than or equal to 25 carbon atoms. Further, α represents an arylene group having greater than or equal to 6 and less than or equal to 25 carbon atoms. It is to be noted that the arylene group may have a substituent or be unsubstituted.

Further, in the above general formula (g-2), as a specific example of the alkyl group having greater than or equal to 1 and less than or equal to 4 carbon atoms, a methyl group, an ethyl group, an i-propyl group, an n-propyl group, an n-butyl group, a t-butyl group, an i-butyl group, an s-butyl group, or the like can be given. As a specific example of the aryl group having greater than or equal to 6 and less than or equal to 25 carbon atoms, a phenyl group, an o-tolyl group, a m-tolyl group, a p-tolyl group, a napthly group, a 2-naphthyl group, a 4-biphenyl group, a 3-biphenyl group, a 2-biphenyl group, a 9,9-methylfluorene-2-yl group, a spiro-9,9'-bifluorene-2-yl group, or the like can be given. As a specific example of the arylene group having greater than or equal to 6 and less than or equal to 25 carbon atoms, an o-phenylene group, a m-phenylene group, a p-phenylene group, a 1,5-naphthylene group, a 1,4-naphthylene group, a 9,9-dimethylfluorene-2,7-diyl group, a 4,4-biphenylene group, a spiro-9,9'-bifluorene-2,7-diyl group, or the like can be given.

Furthermore, in the above general formula (g-2), when A in the formula is the substituent represented by the general formula (a-1), and $Ar^1$ and $Ar^2$ are any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group, synthesis becomes easy, which is preferable in the present invention. In other words, the present invention is preferably a pyrazine derivative represented by the following general formula (g-9).

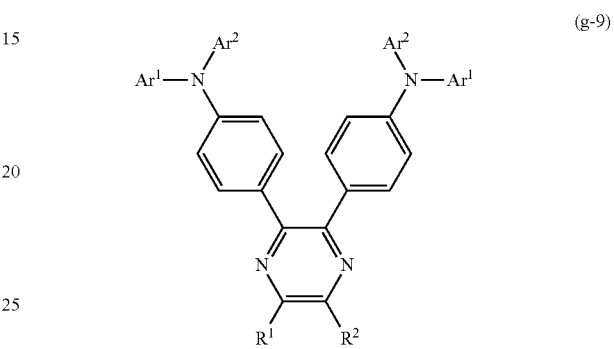

(g-9)

In the above general formula (g-9), each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. It is to be noted that the aryl group may have a substituent or be unsubstituted.

Further, in the above general formula (g-2), when A in the formula is the substituent represented by the general formula (a-2), and α is a phenylene group, much higher triplet excitation energy can be obtained, and chemical stability can be obtained, which is preferable in the present invention. In other words, the present invention is preferably a pyrazine derivative represented by the following general formula (g-10).

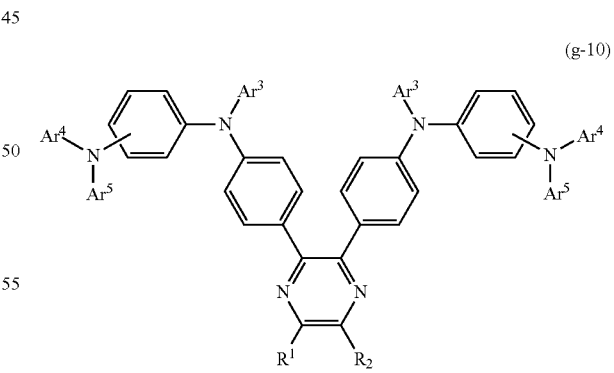

(g-10)

In the above general formula (g-10), each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $Ar^3$, $Ar^4$, and $Ar^5$ may be same or different, and represents an aryl group having greater than or equal to 6 and less than equal to 25 carbon atoms. It is to be noted that the aryl group may have a substituent or be unsubstituted.

Further, in the above general formula (g-2), when A in the formula is the substituent represented by the general formula (a-2), $Ar^4$ and $Ar^5$ are a phenyl group, and α is a 1,4-phenylene group, much higher triplet excitation energy can be obtained, and synthesis becomes easy, which is preferable in the present invention. In other words, the present invention is preferably a pyrazie derivative represented by the following general formula (g-11).

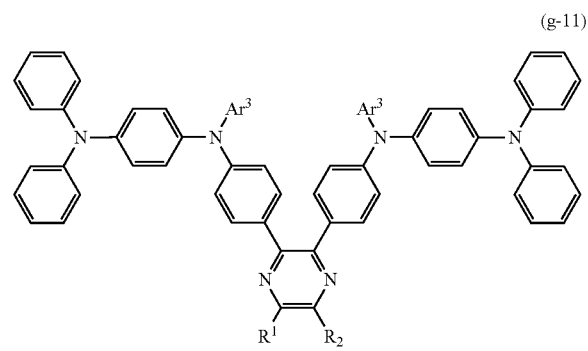

(g-11)

In the above general formula (g-11), each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $Ar^3$ represents an aryl group having greater than or equal to 6 and less than or equal to 25 carbon atoms. It is to be noted that the aryl group may have a substituent or be unsubstituted.

Further, in the above general formula (g-11), when $Ar^3$ in the formula is any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group, synthesis becomes easy, which is preferable in the present invention.

Furthermore, in the above general formula (g-2), when A in the formula is the substituent represented by the general formula (a-3), $Ar^6$ is any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group, synthesis becomes easy, which is preferable in the present invention. In other words, the present invention is preferably a pyrazine derivative represented by the following general formula (g-12).

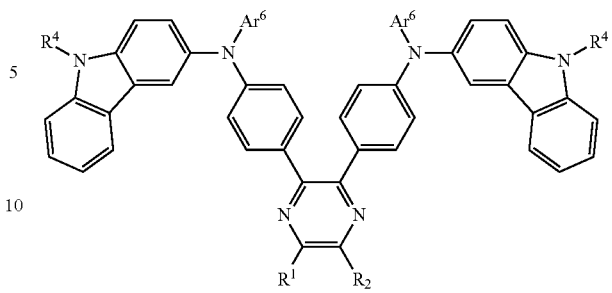

(g-12)

In the above general formula (g-12), each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $R^4$ represents an alkyl group having greater than or equal to 1 and less than or equal to 4 carbon atoms or an aryl group having greater than or equal to 6 and less than or equal to 25 carbon atoms. It is to be noted that the aryl group may have a substituent or be unsubstituted.

Further, in the above general formula (g-2), when A in the formula is the substituent represented by the general formula (a-4), and α is a phenylene group, much higher triplet excitation energy can be obtained, and chemical stability can be obtained, which is preferably in the present invention. In other words, the present invention is preferably a pyrazine derivative represented by the following general formula (g-13).

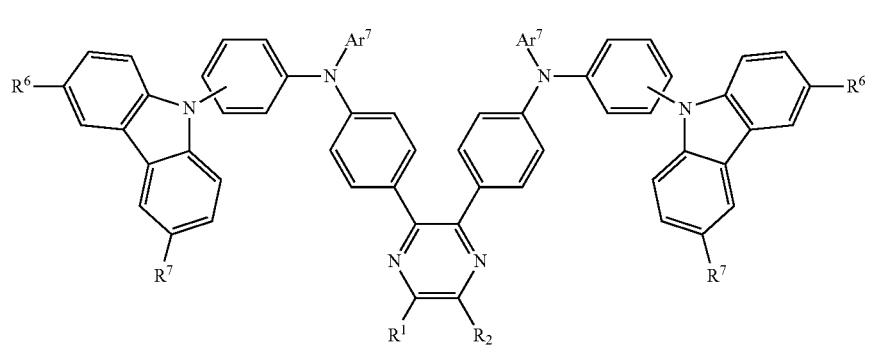

(g-13)

In the above general formula (g-13), each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $R^6$ and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $Ar^7$ represents an aryl group having greater than or equal to 6 and less than or equal to 25 carbon atoms. It is to be noted that the aryl group may have a substituent or be unsubstituted.

Further, in the above general formula (g-2), when A in the formula is the substituent represented by the general formula (a-4), and α is a 1,4-phenylene group, much higher triplet excitation energy can be obtained, and chemical stability can be obtained, which is preferably in the present invention. In other words, the present invention is a pyrazine derivative represented by the following general formula (g-14).

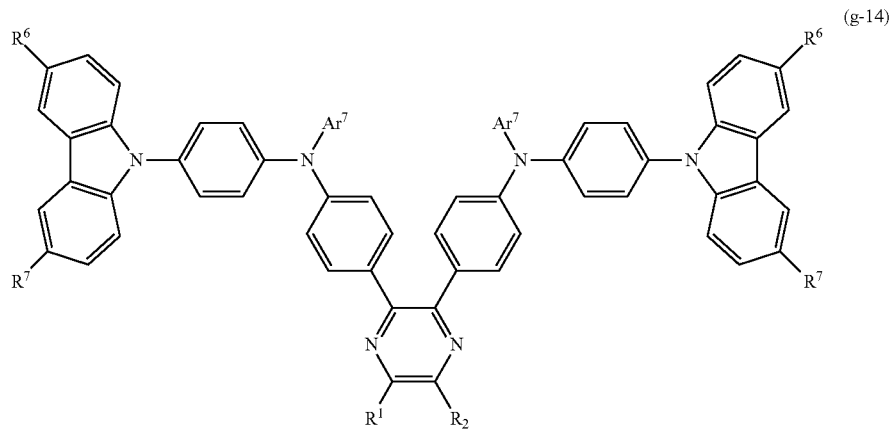

(g-14)

In the above general formula (g-14), each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. Each of $R^6$ and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. $Ar^7$ represents an aryl group. It is to be noted that the aryl group may have a substituent or be unsubstituted.

Further, in the above general formula (g-14), when $Ar^1$ in the formula is any of a phenyl group, a 1-naphthyl group, a 2-naphthyl group, a 2-biphenyl group, a 3-biphenyl group, a 4-biphenyl group, a 9,9-dimethylfluorene-2-yl group, and a spiro-9,9'-bifluorene-2-yl group, synthesis becomes easy, which is preferable in the present invention.

As a specific example of a pyrazine derivative of the present invention, pyrazine derivatives represented by structural formulas (s-1) to (s-115) can be given. It is to be noted that a pyrazine derivative of the present invention is not limited to the structural formulas below, and a different structure from a structure represented by the following formulas can be employed.

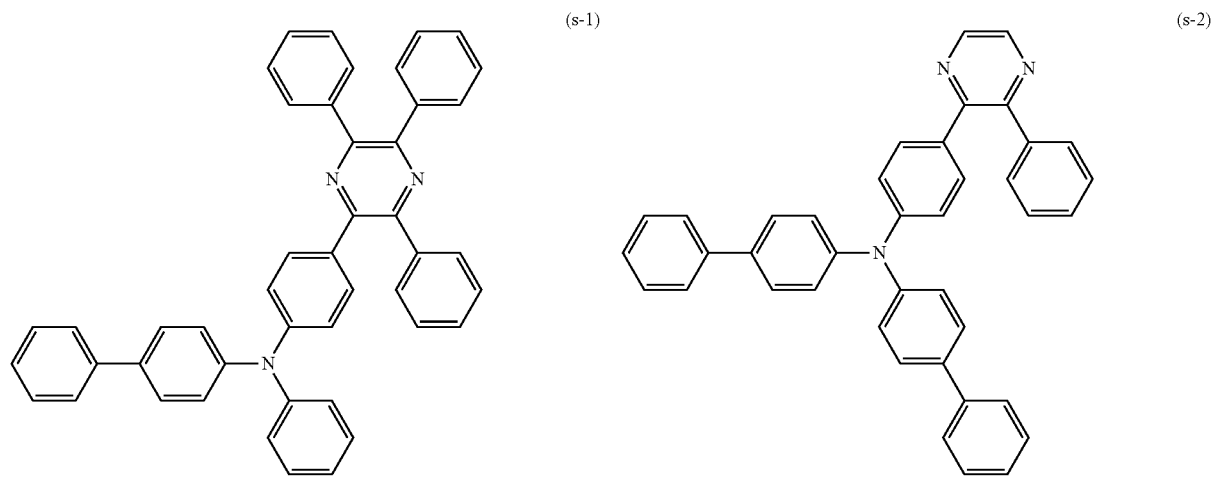

-continued
(s-3)
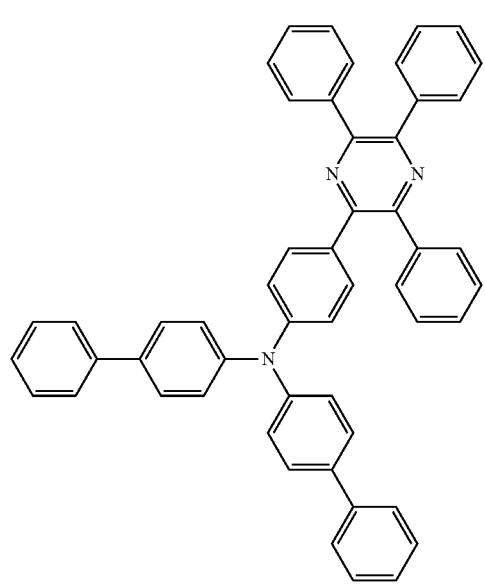
(s-4)
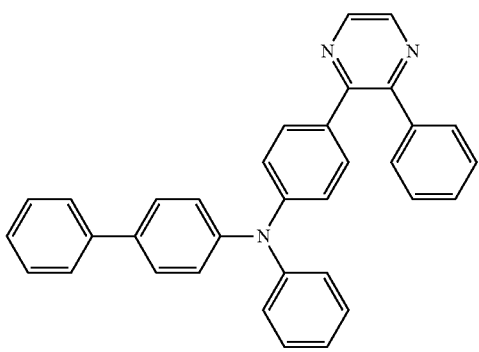
(s-5)
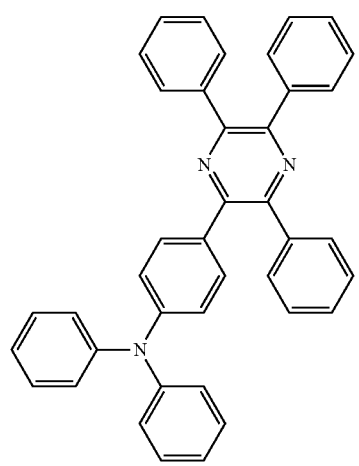
(s-6)
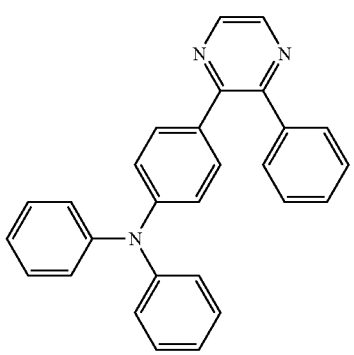
(s-7)
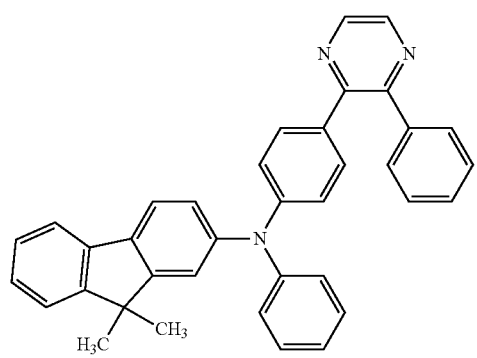
(s-8)
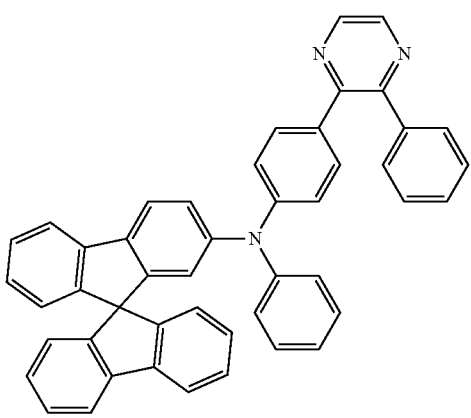

-continued
(s-9)
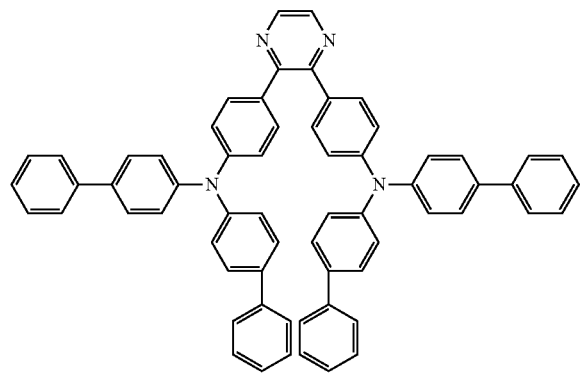
(s-10)
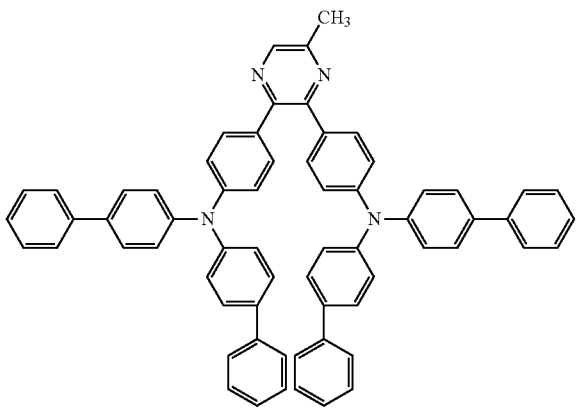
(s-11)
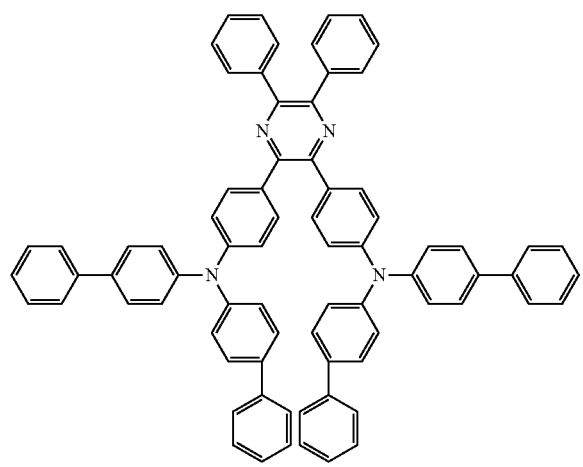
(s-12)
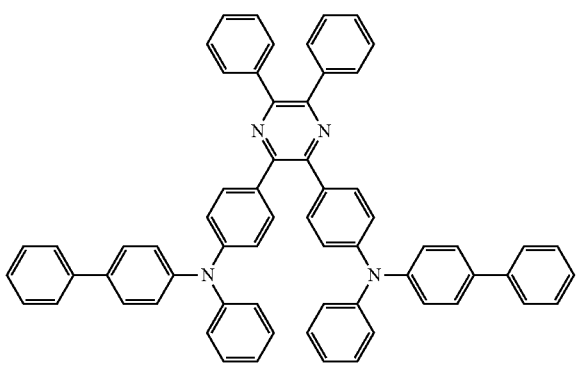
(s-13)
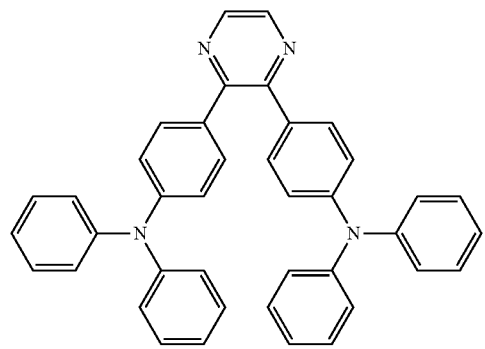
(s-14)
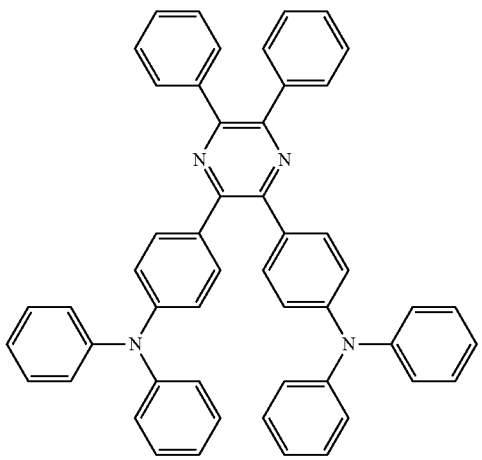

-continued
(s-15)
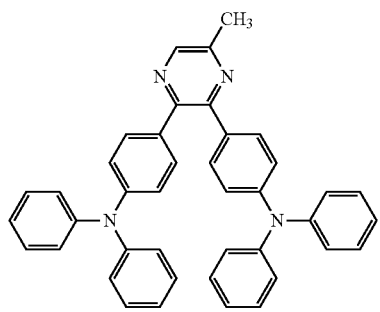
(s-16)
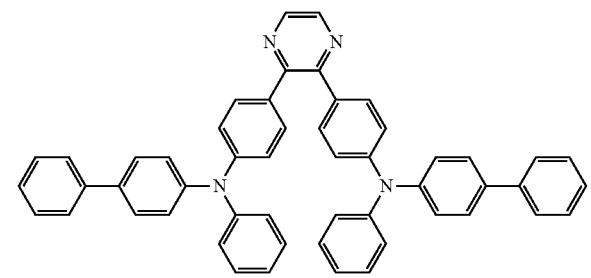
(s-17)
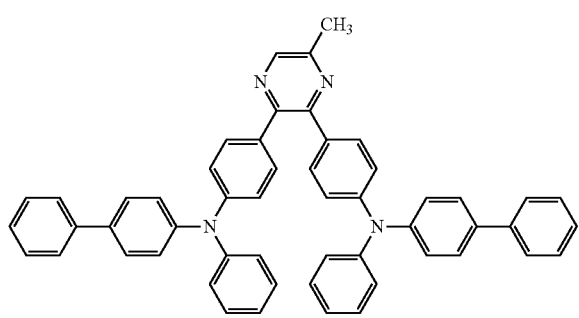
(s-18)
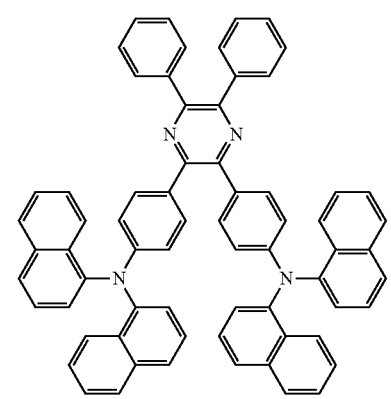
(s-19)
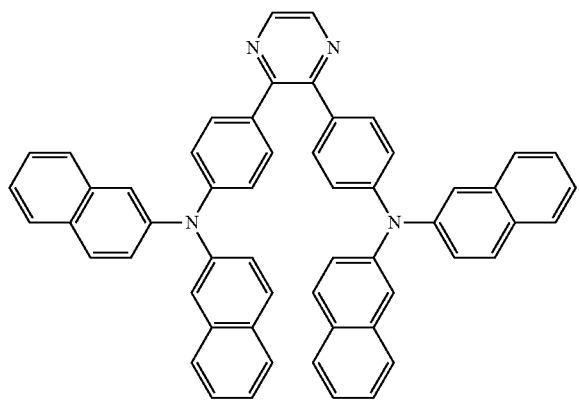
(s-20)
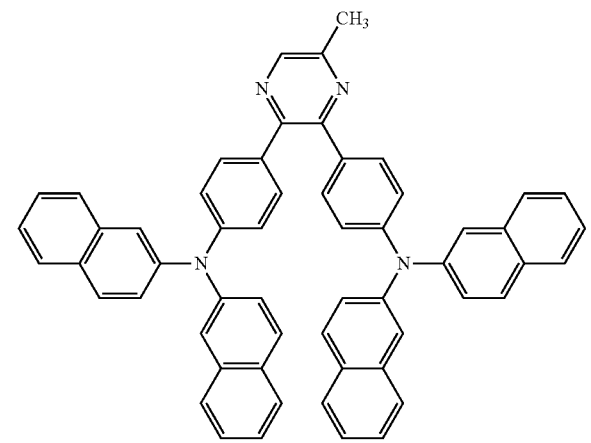
(s-21)
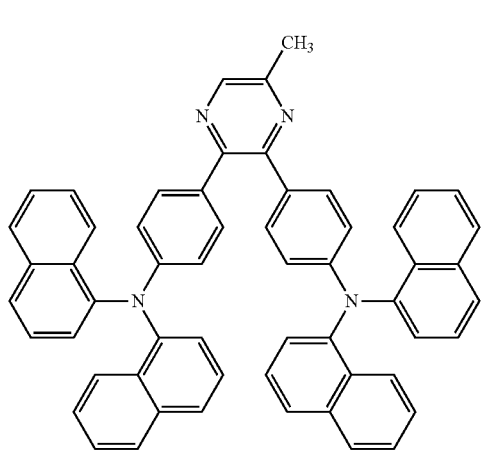
(s-22)
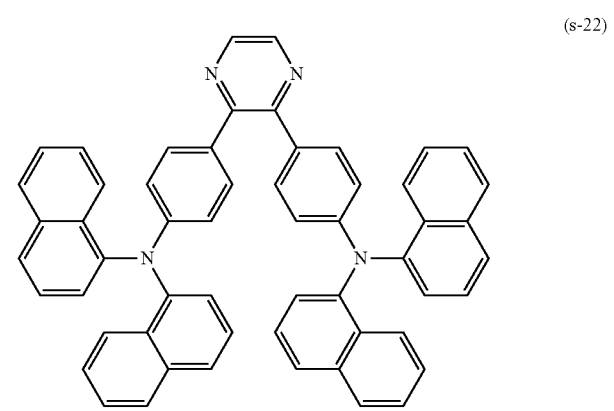

-continued
(s-23)
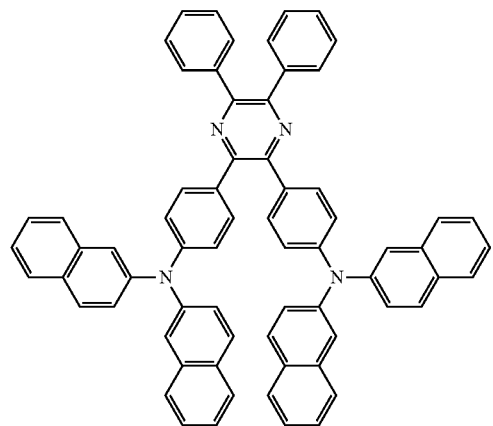
(s-24)
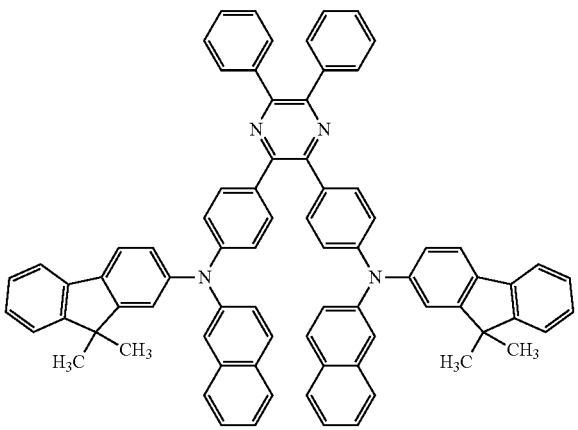
(s-25)
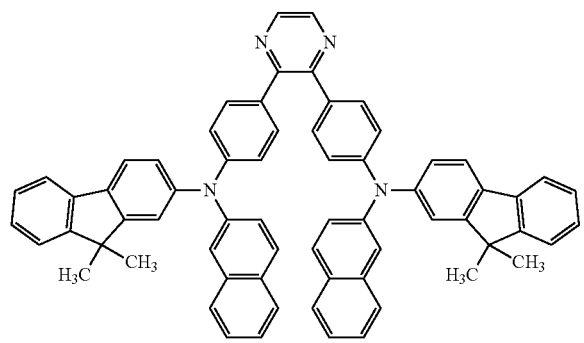
(s-26)
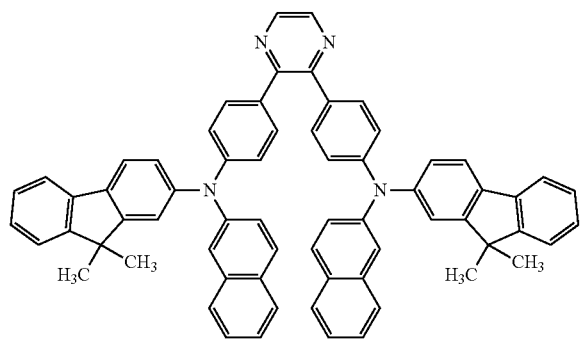
(s-27)
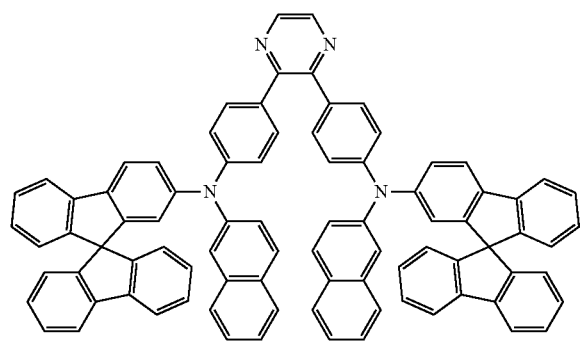
(s-28)
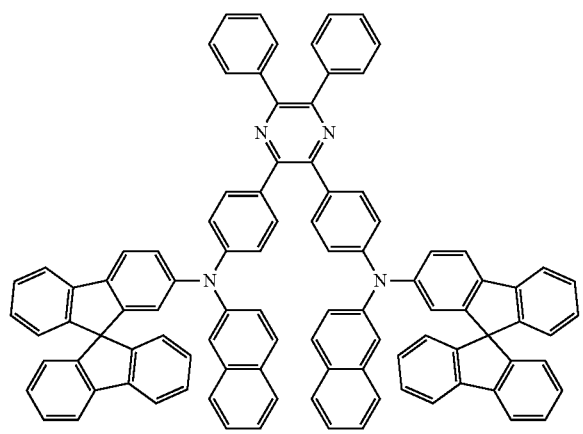
(s-29)
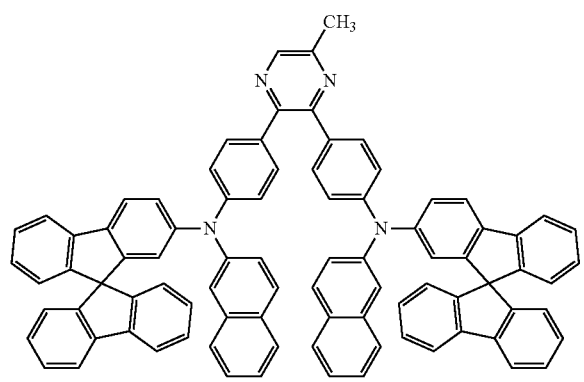
(s-30)
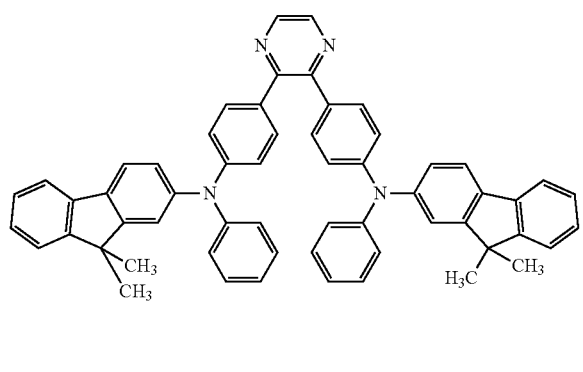

-continued
(s-31)
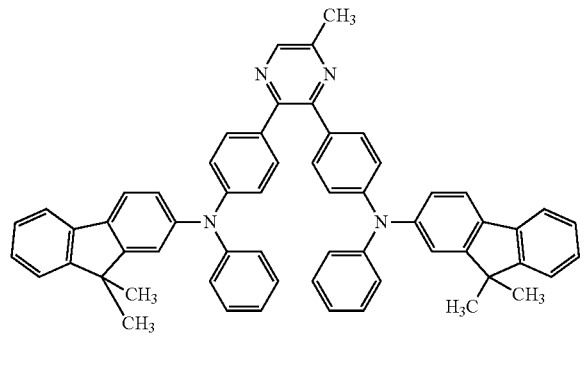
(s-32)
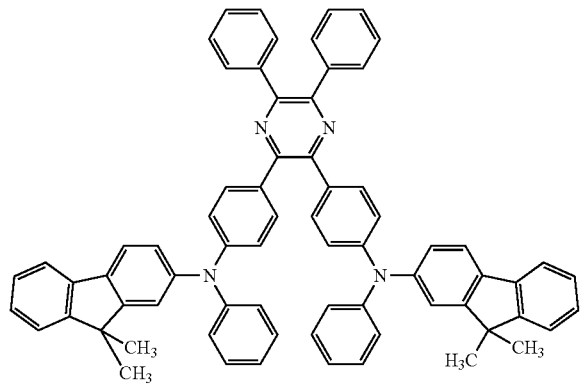
(s-33)
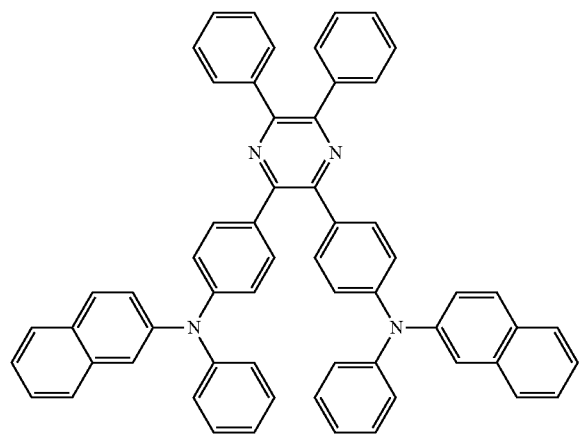
(s-34)
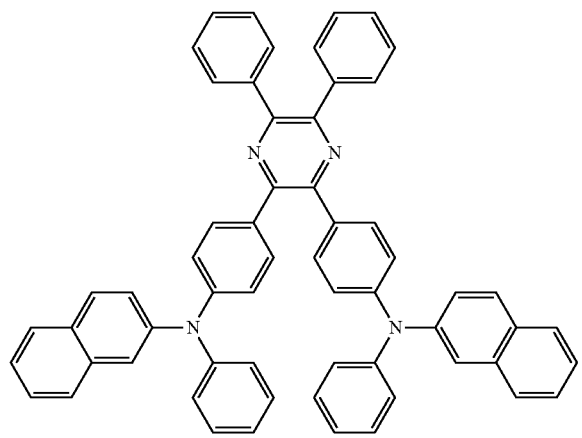
(s-35)
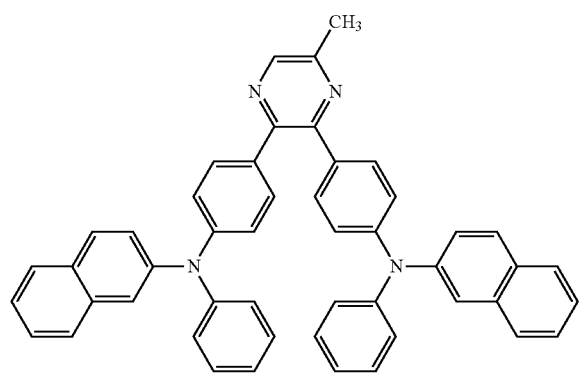
(s-36)
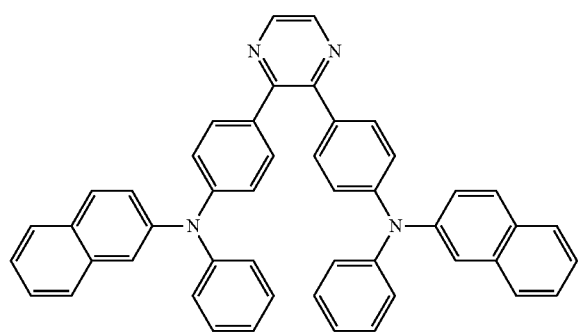

-continued
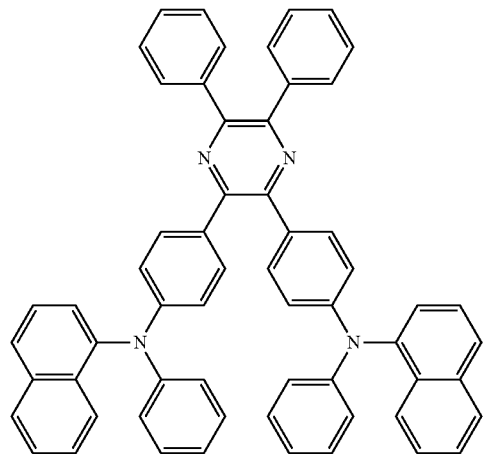
(s-37)
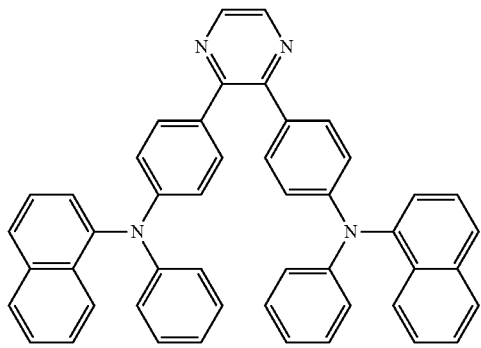
(s-38)
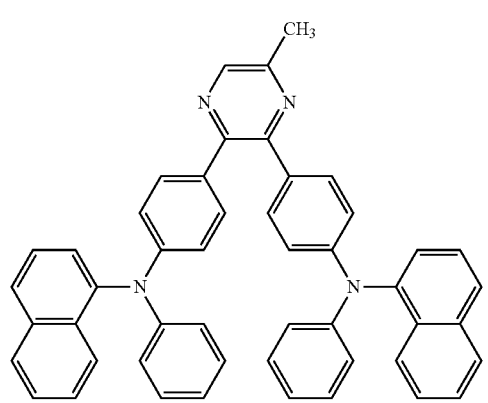
(s-39)
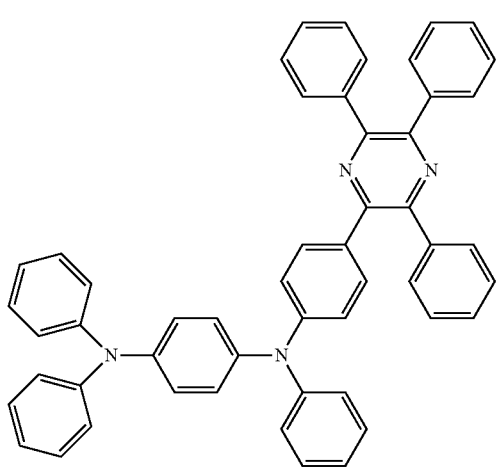
(s-40)
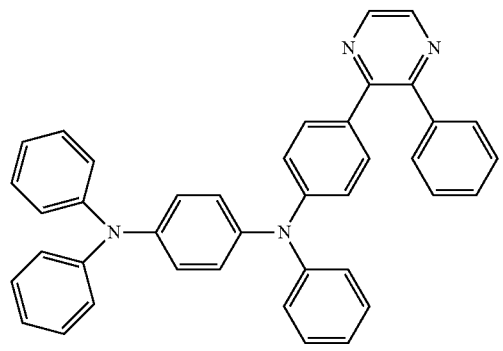
(s-41)
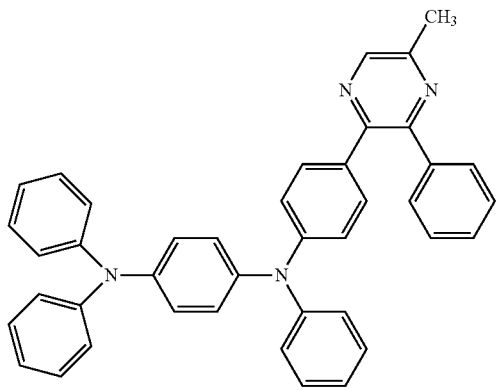
(s-42)

-continued
(s-43)
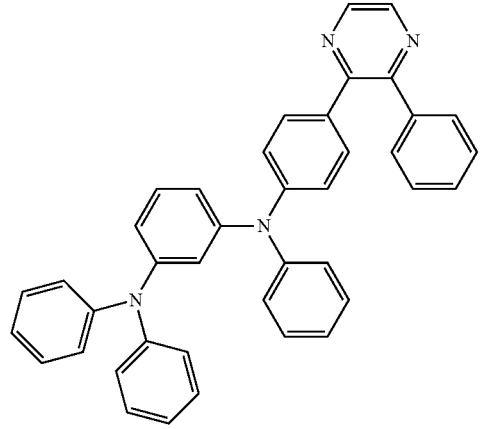
(s-44)
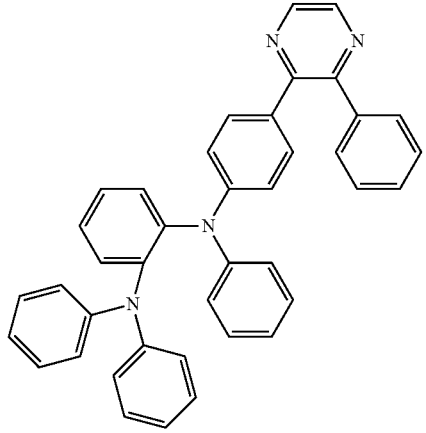
(s-45)
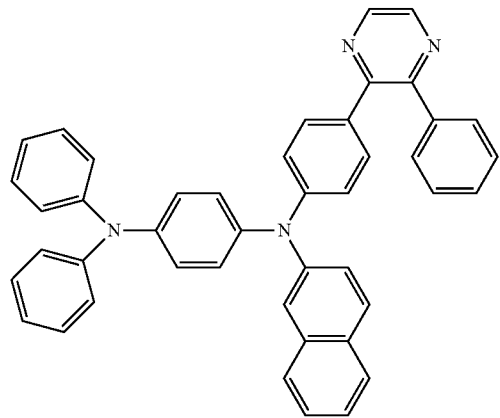
(s-46)
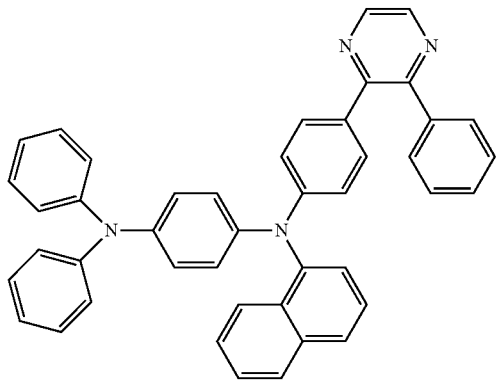
(s-47)
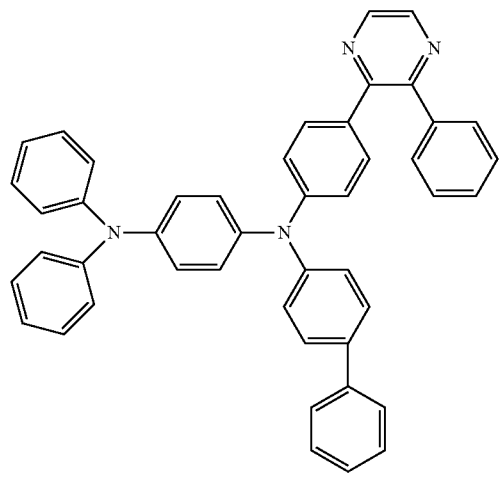
(s-48)
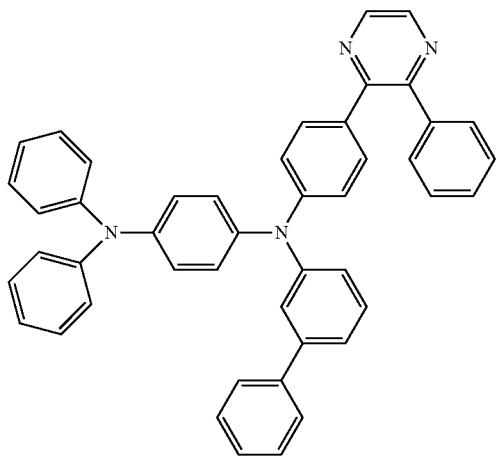

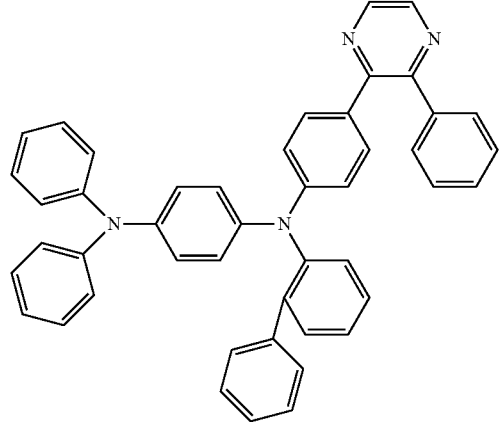 (s-49)
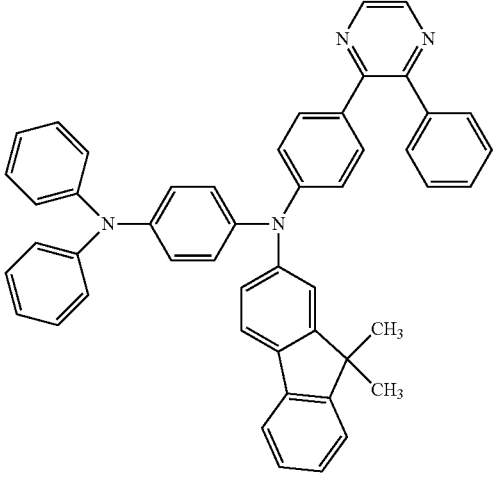 (s-50)
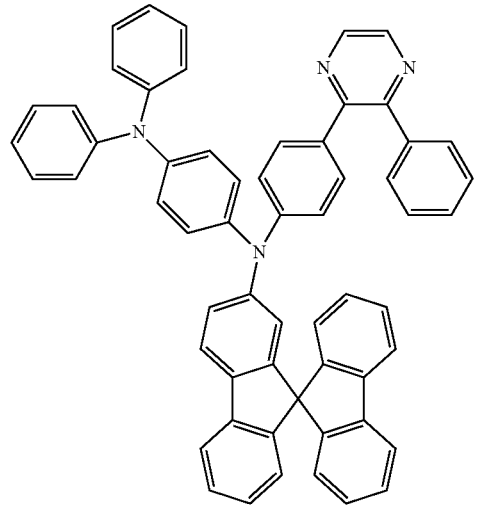 (s-51)
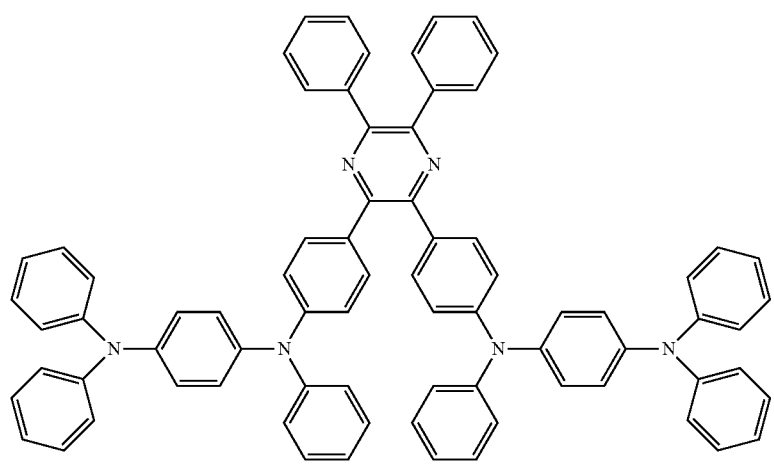 (s-52)

-continued
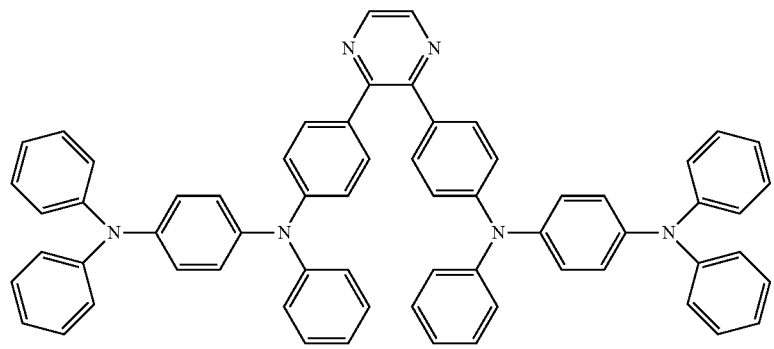
(s-53)
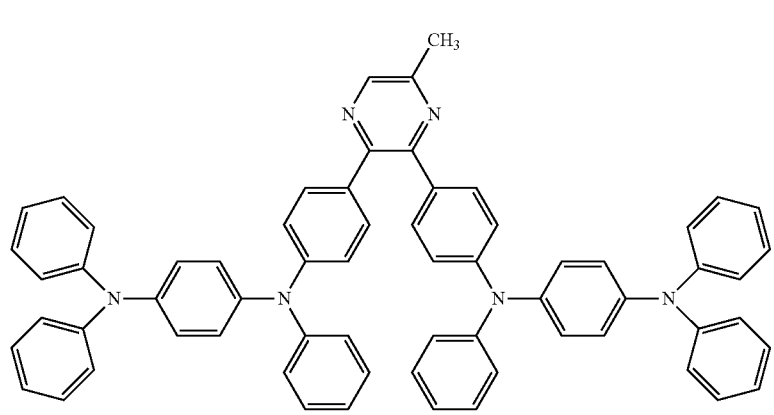
(s-54)
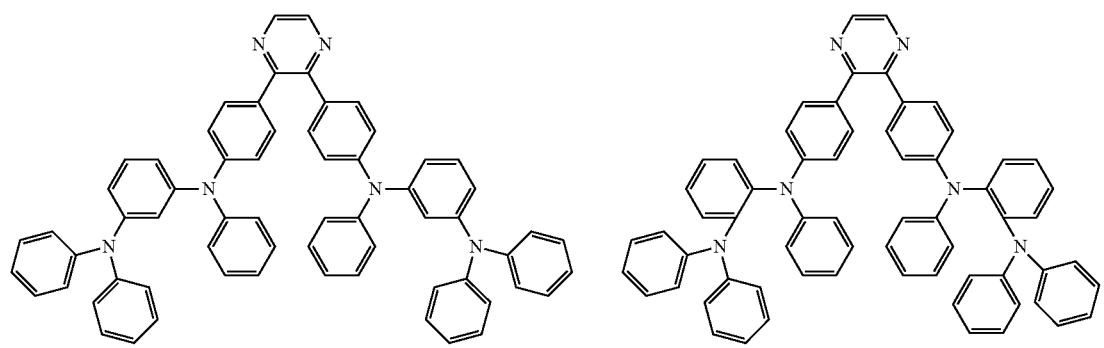
(s-55) (s-56)
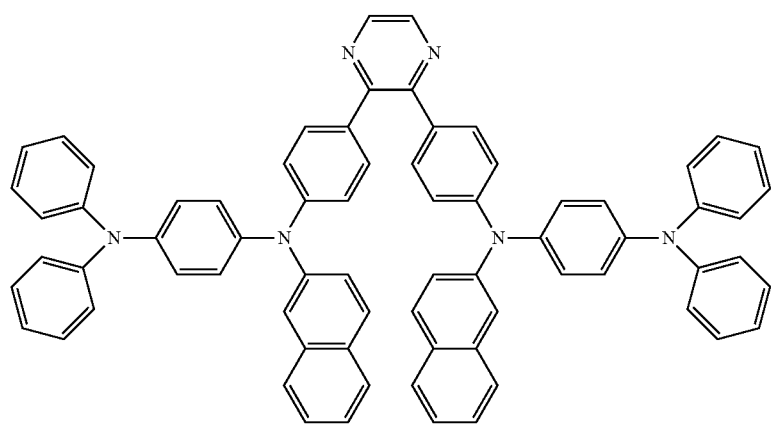
(s-57)

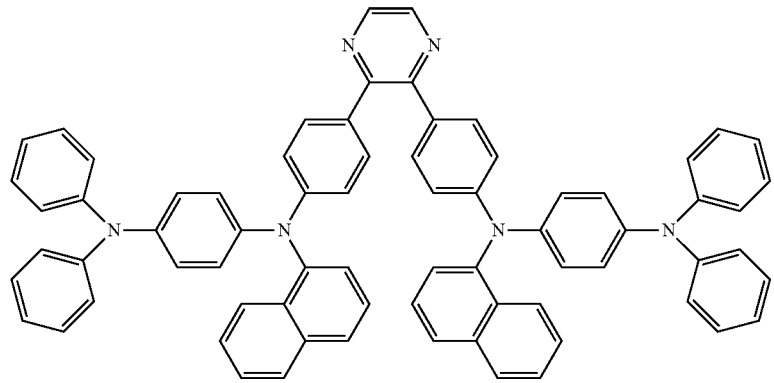
(s-58)
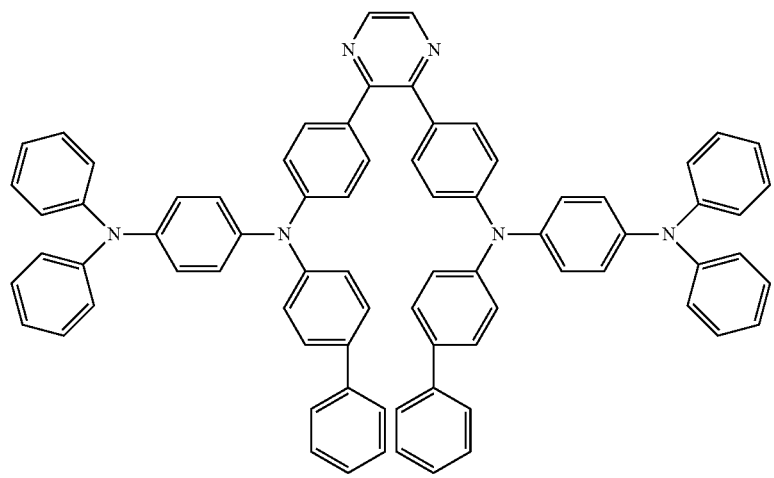
(s-59)
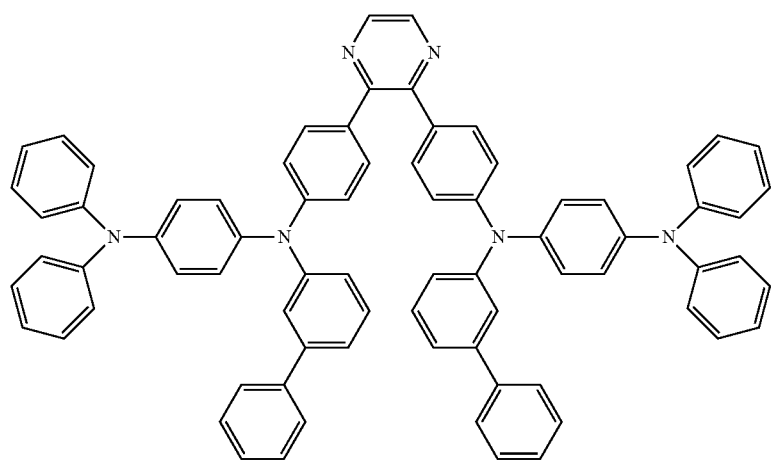
(s-60)

-continued
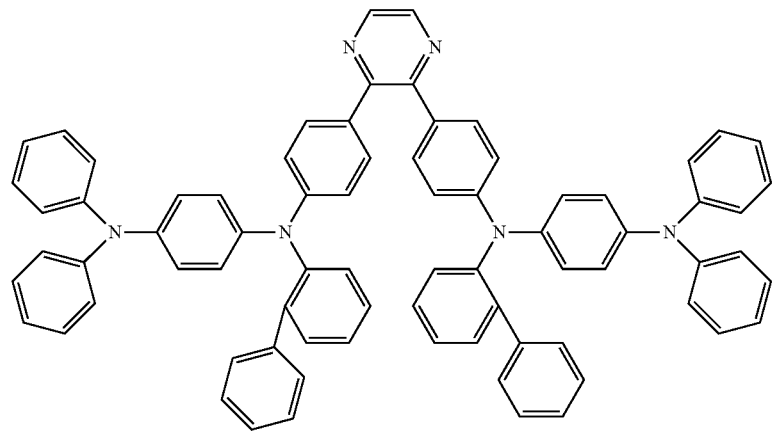
(s-61)
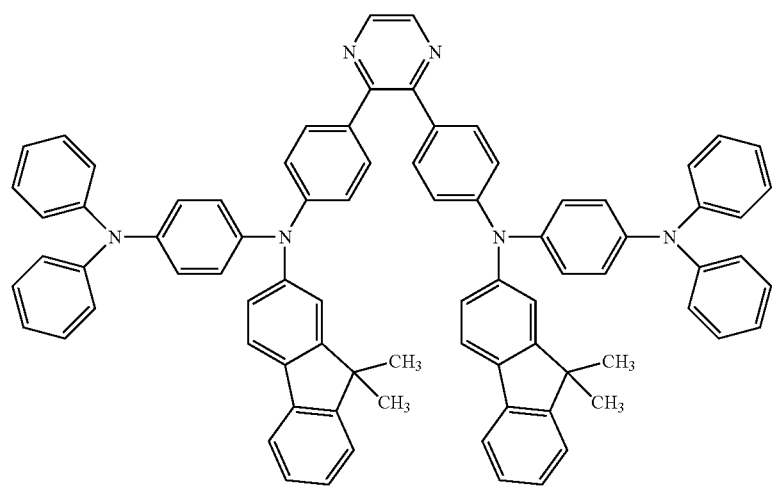
(s-62)
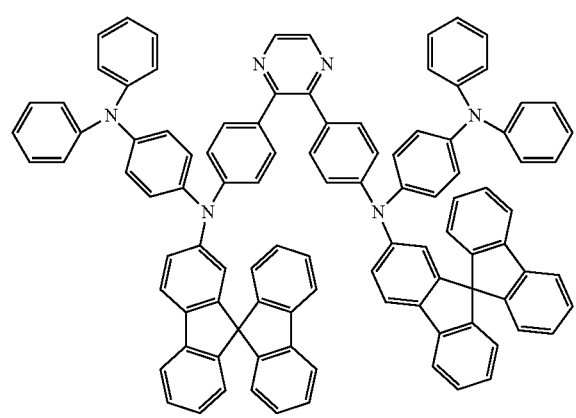
(s-63)
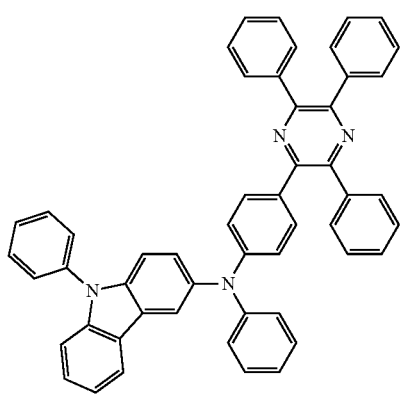
(s-64)

-continued
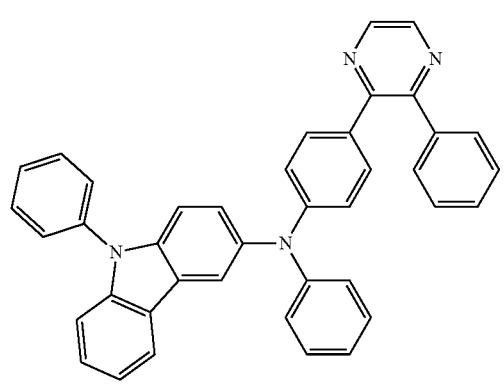
(s-65)
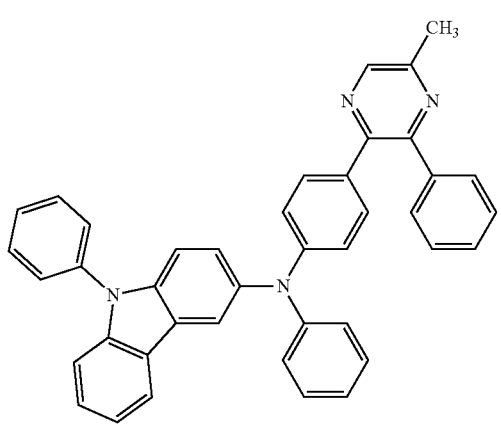
(s-66)
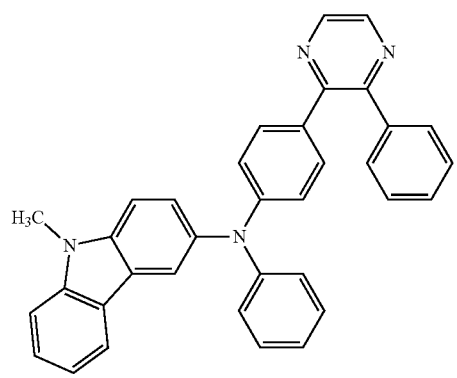
(s-67)
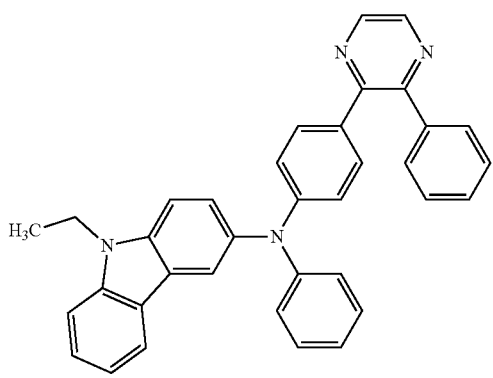
(s-68)
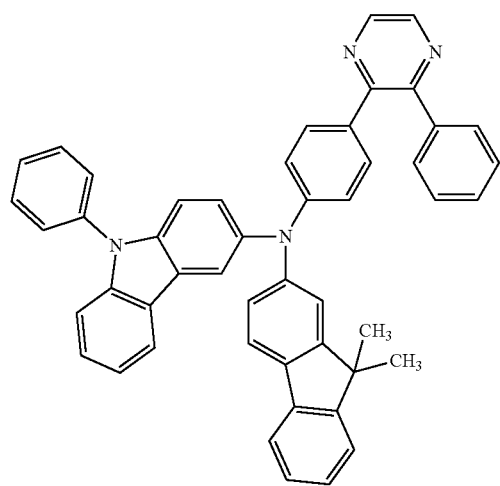
(s-69)
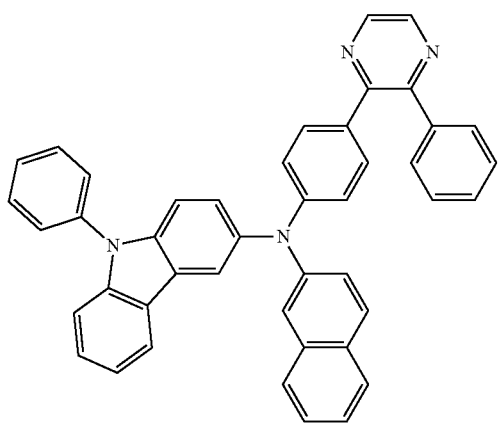
(s-70)

-continued
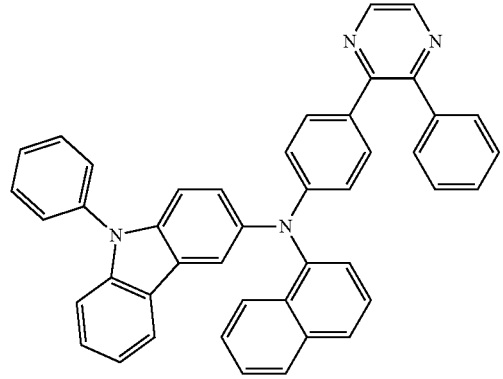
(s-71)
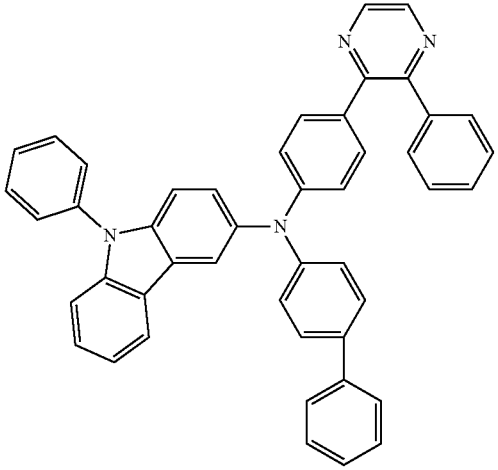
(s-72)
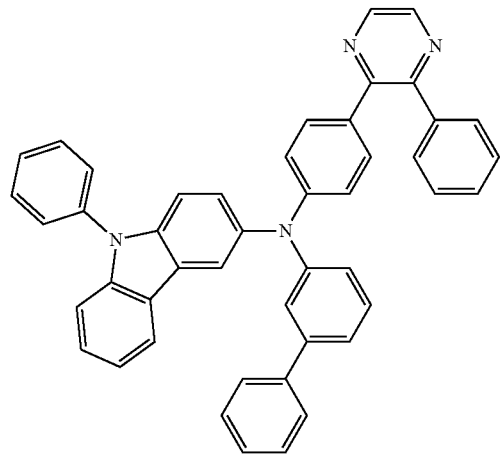
(s-73)
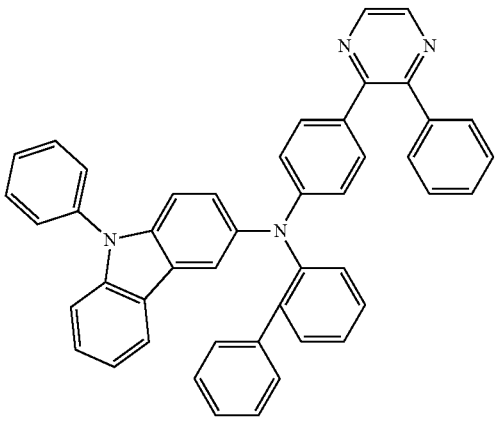
(s-74)
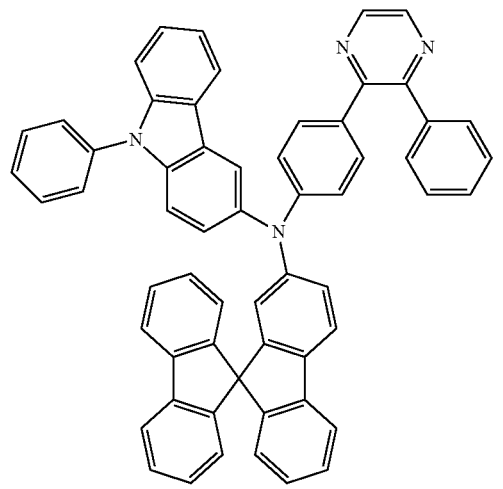
(s-75)

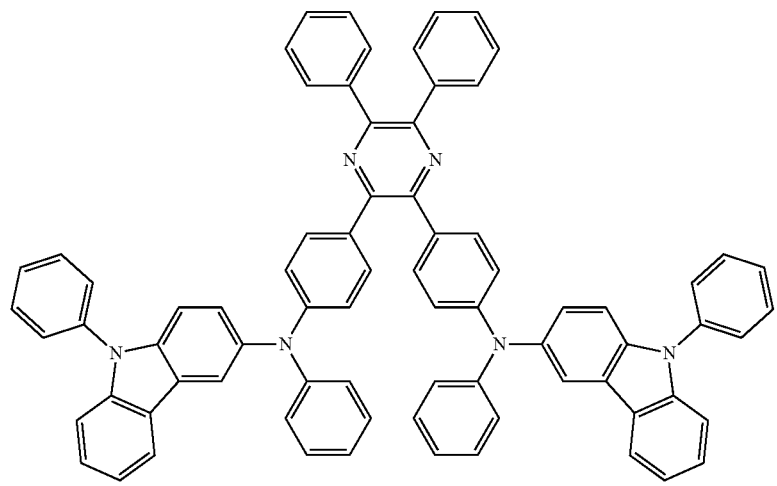
(s-76)
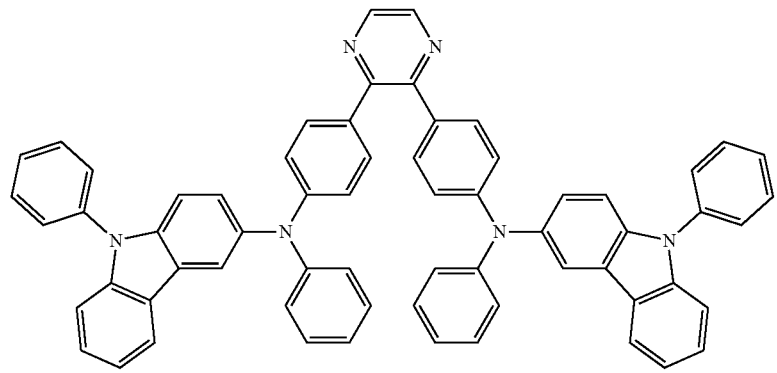
(s-77)
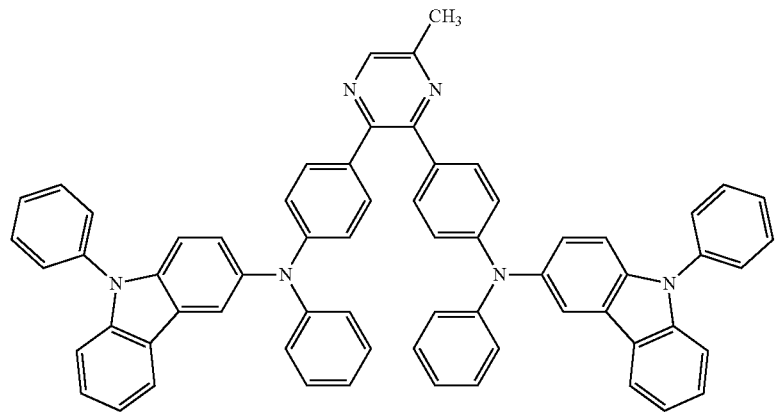
(s-78)
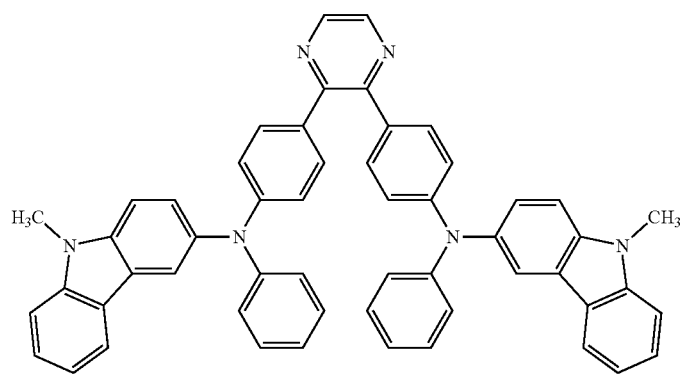
(s-79)

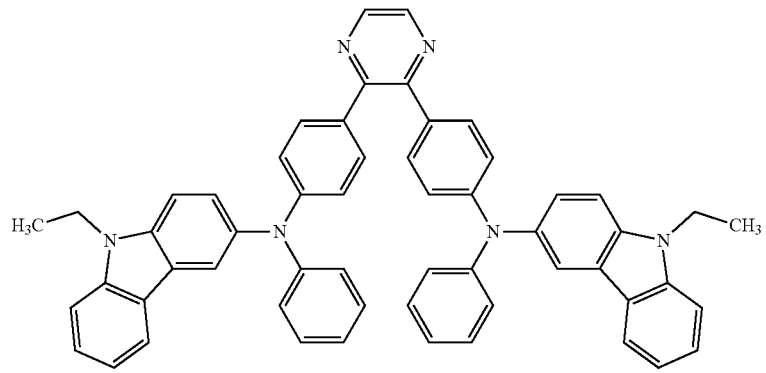
(s-80)
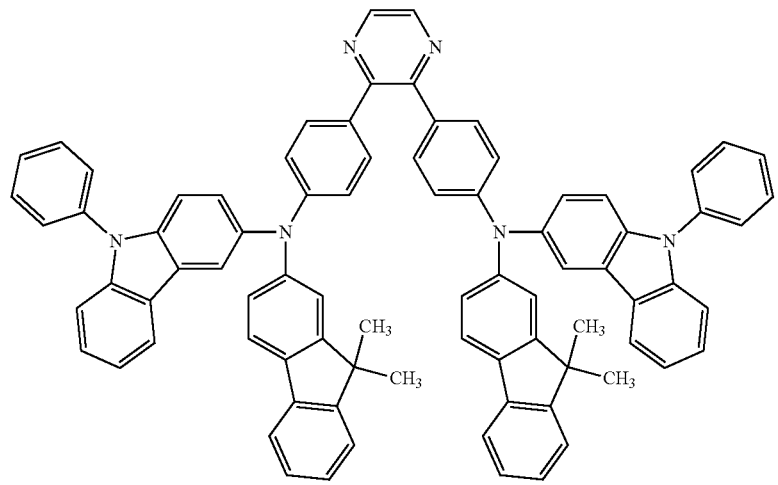
(s-81)
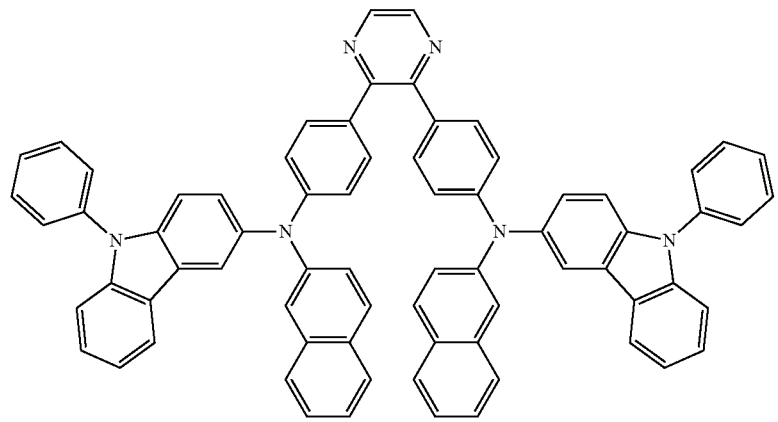
(s-82)
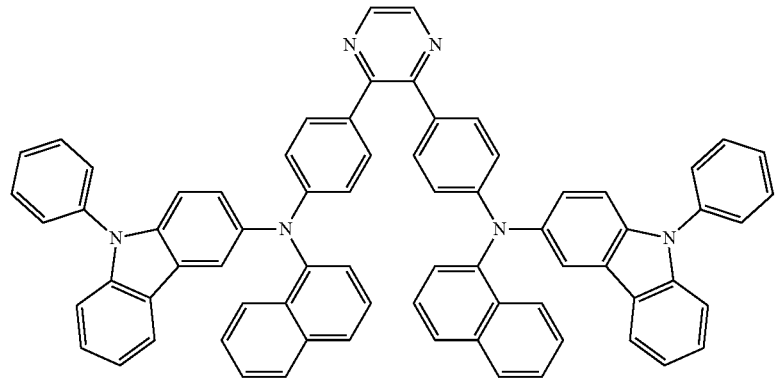
(s-83)

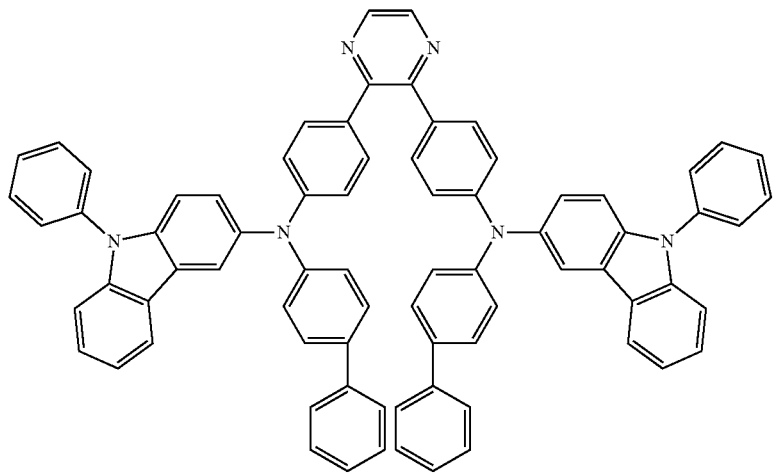
(s-84)
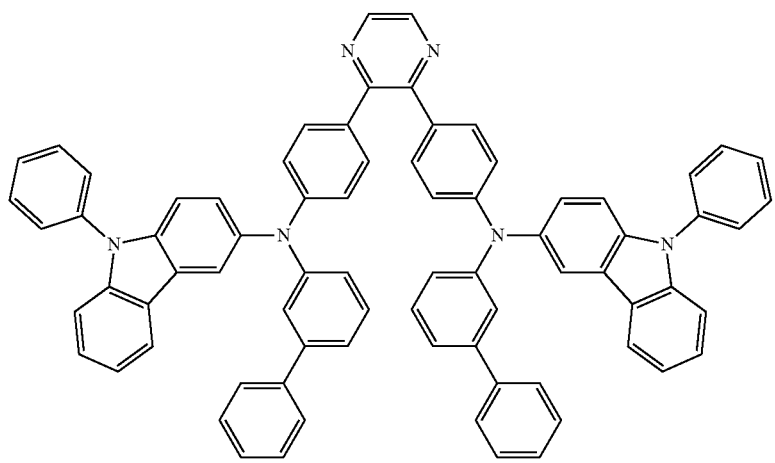
(s-85)
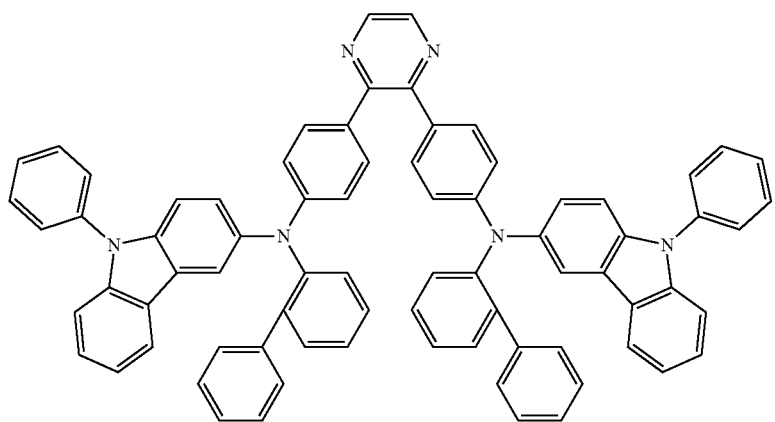
(s-86)

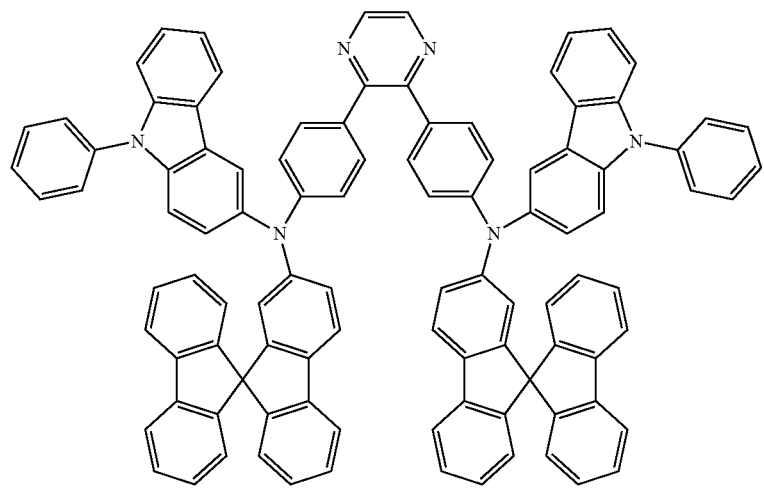
(s-87)
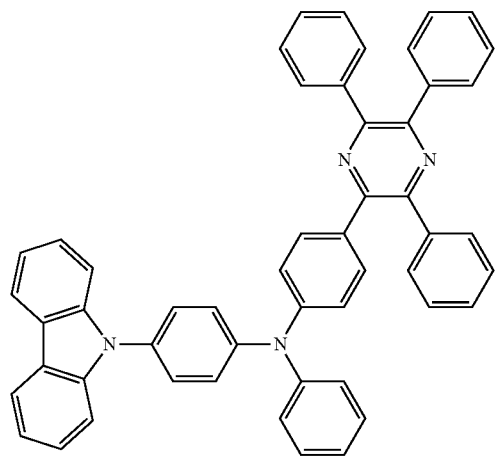
(s-88)
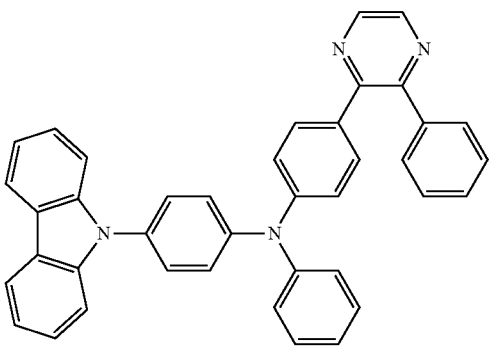
(s-89)
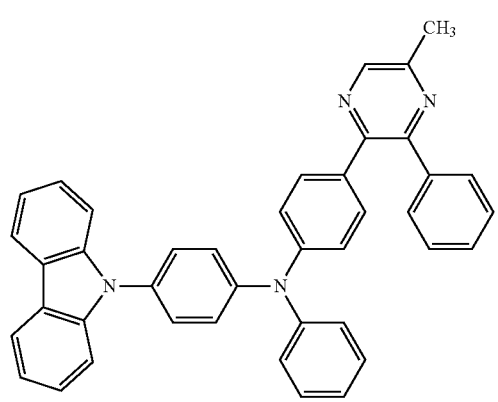
(s-90)
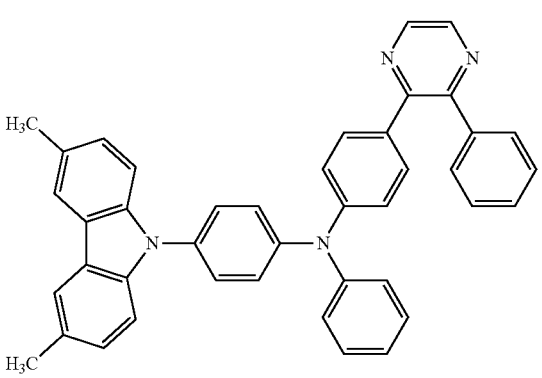
(s-91)

-continued
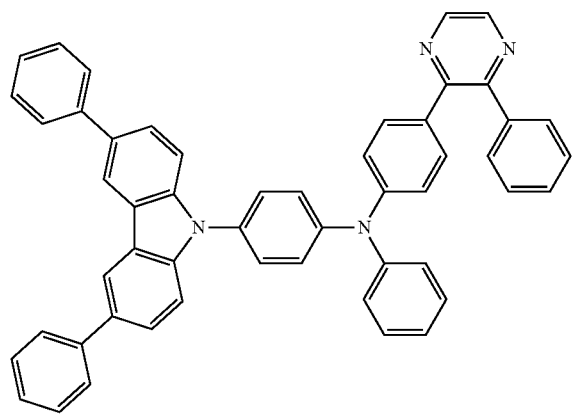
(s-92)
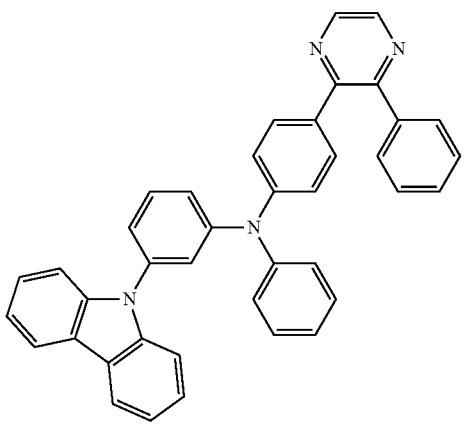
(s-93)
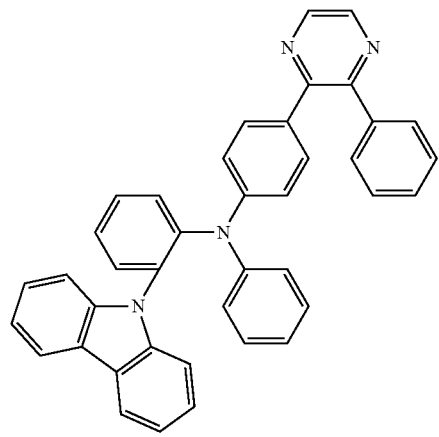
(s-94)
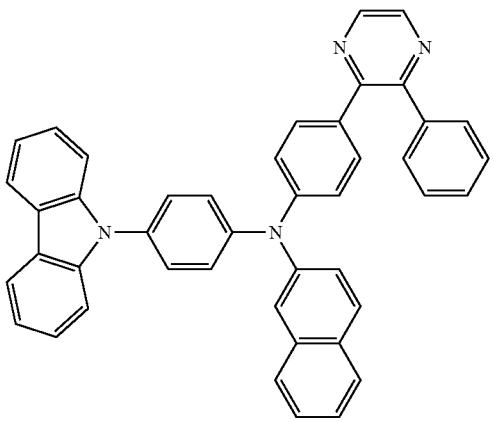
(s-95)
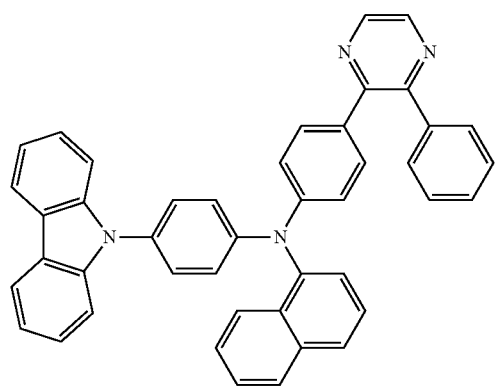
(s-96)
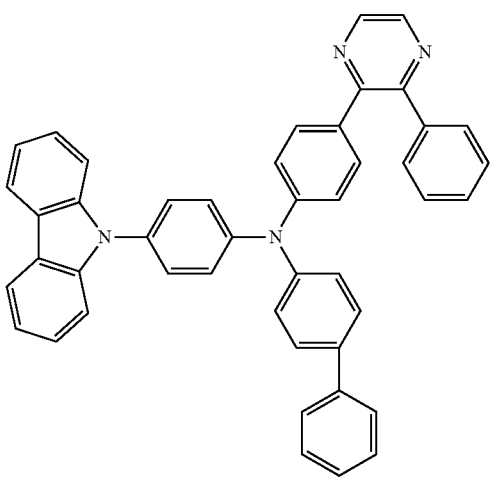
(s-97)

-continued
(s-98)
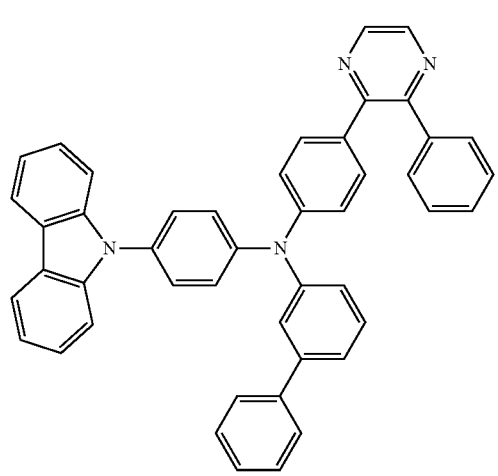
(s-99)
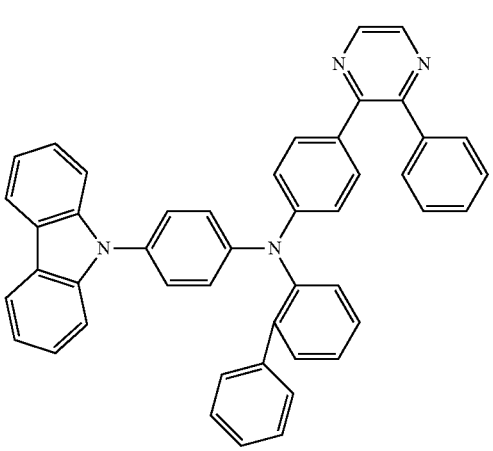
(s-100)
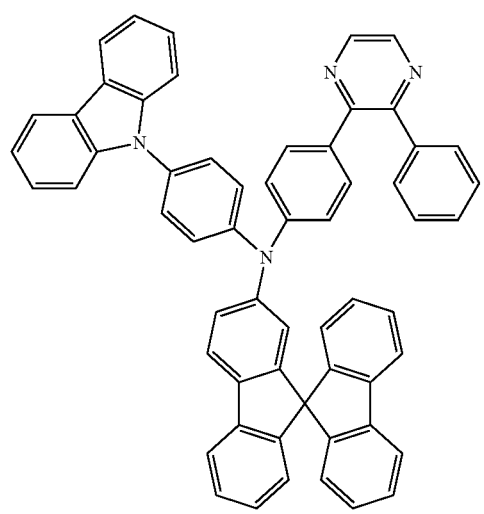
(s-101)
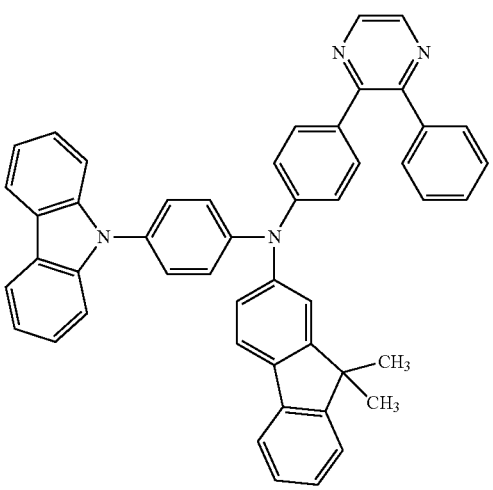
(s-102)
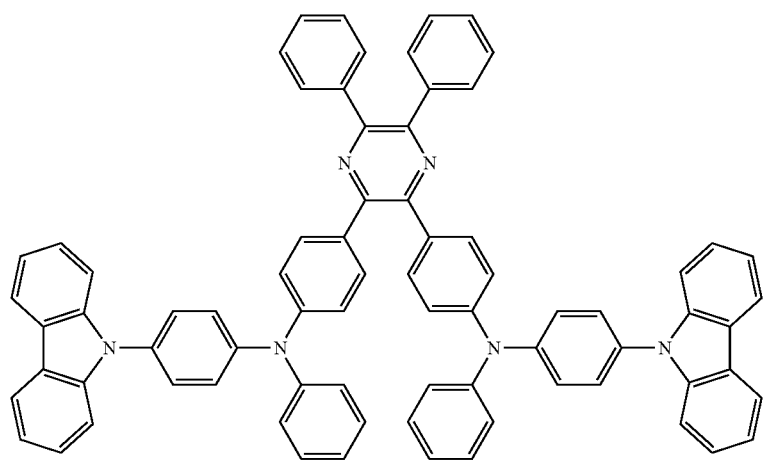

-continued
(s-103)
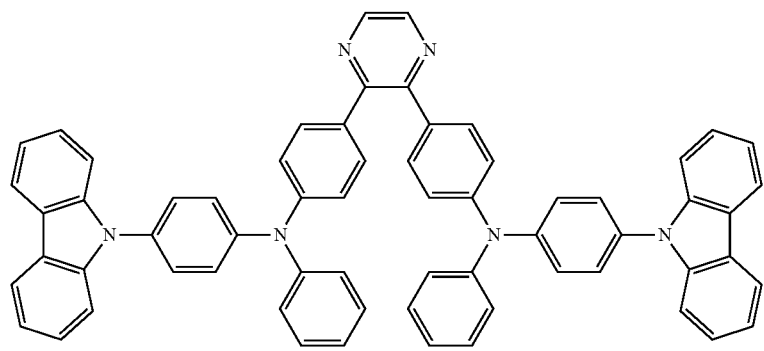
(s-104)
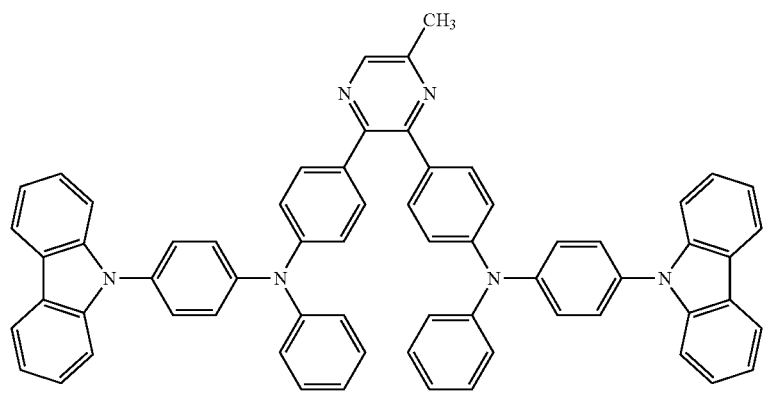
(s-105)
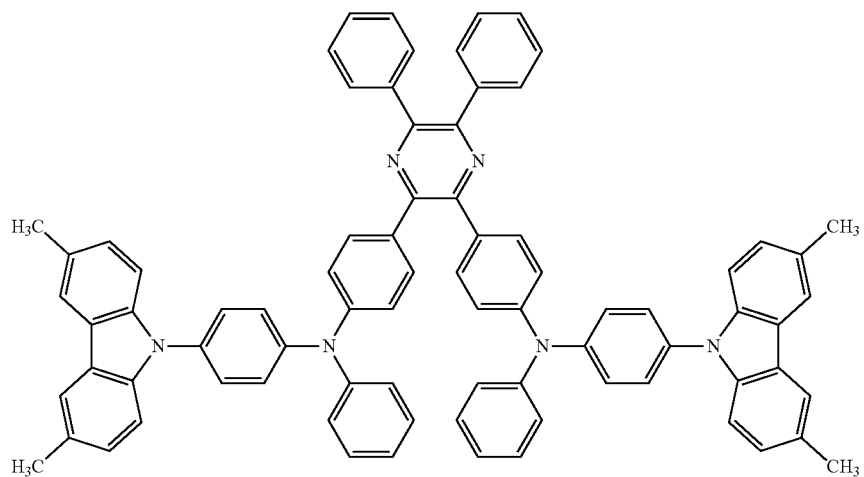
(s-106)
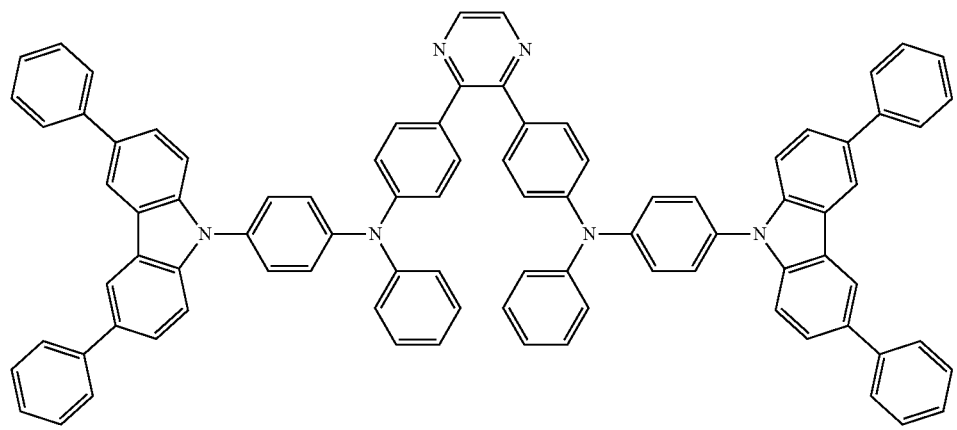

(s-107)
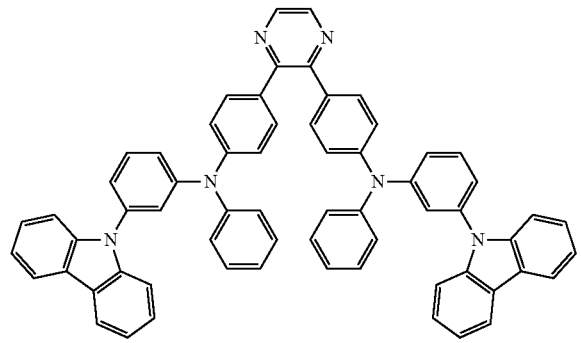
(s-108)
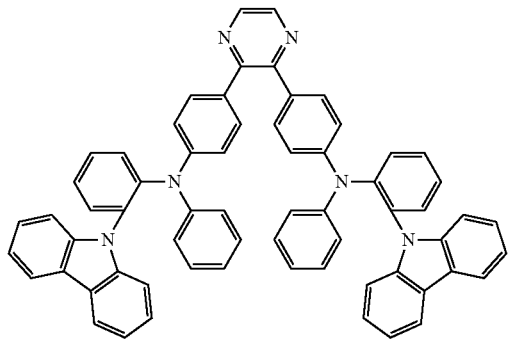
(s-109)
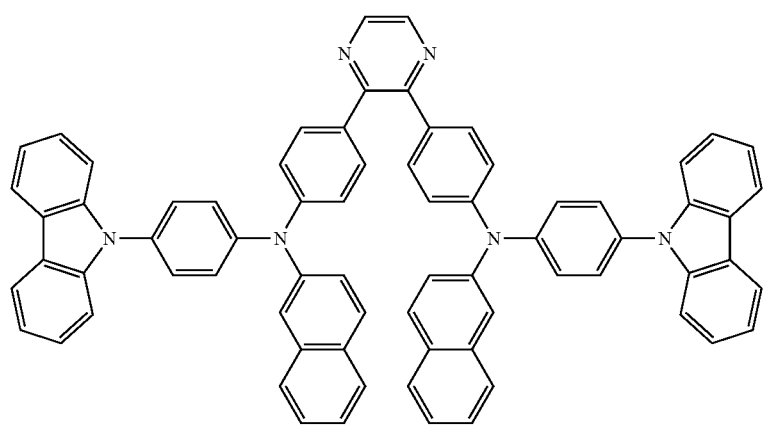
(s-110)
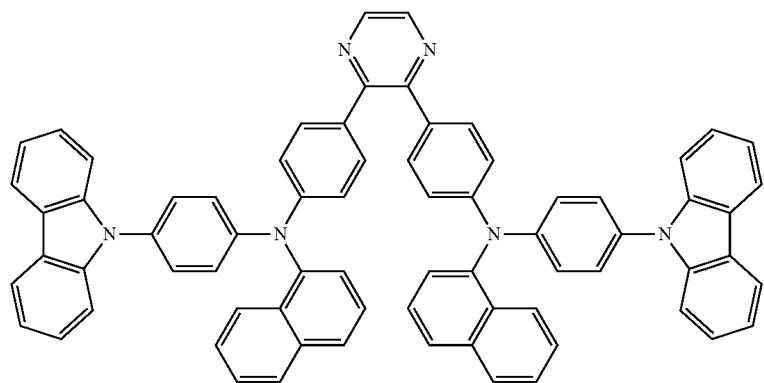
(s-111)
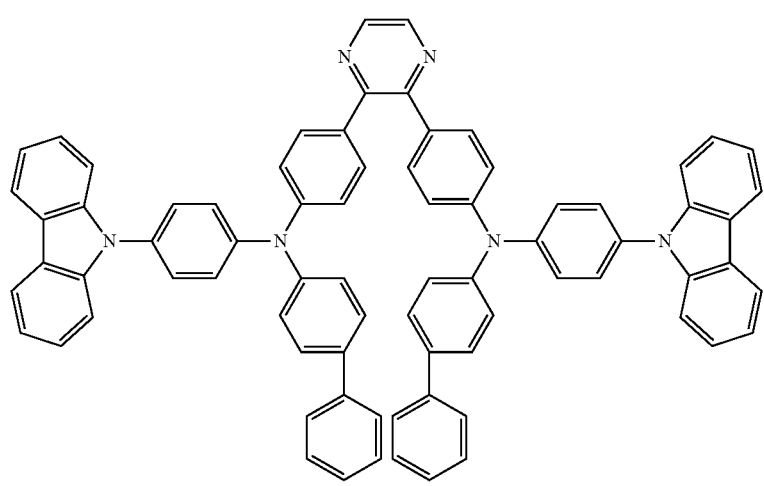

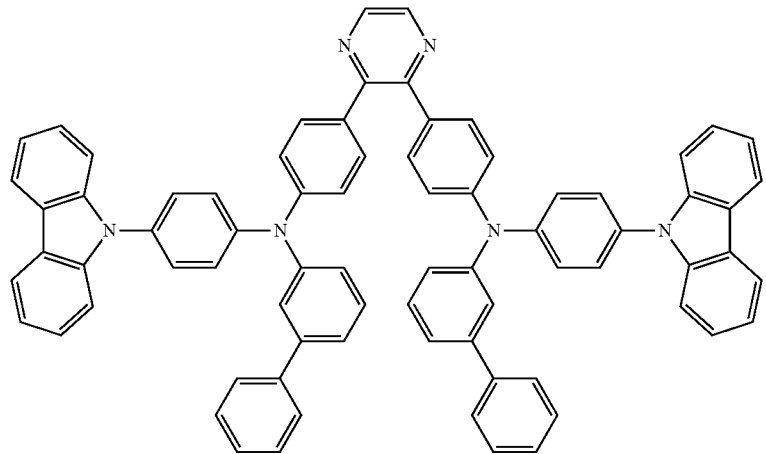
(s-112)
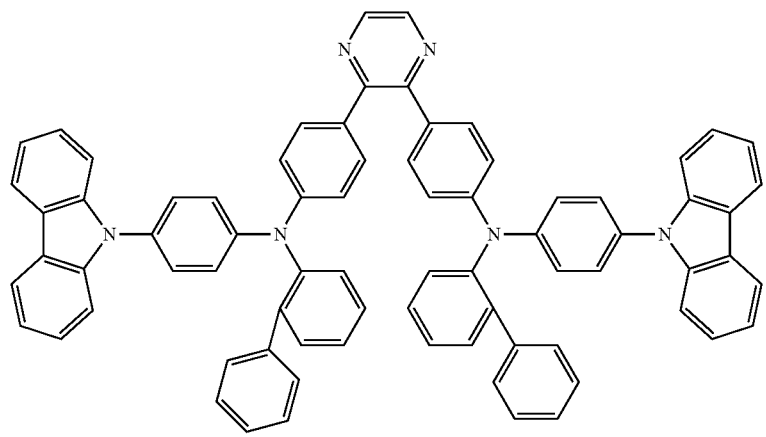
(s-113)
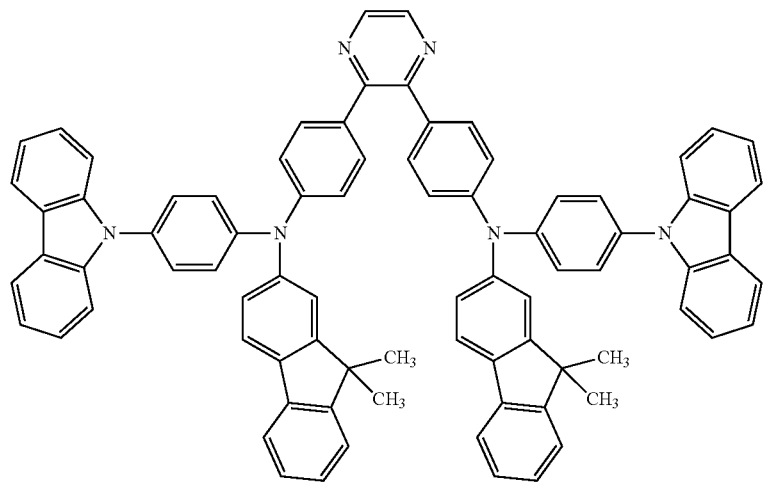
(s-114)

(s-115)
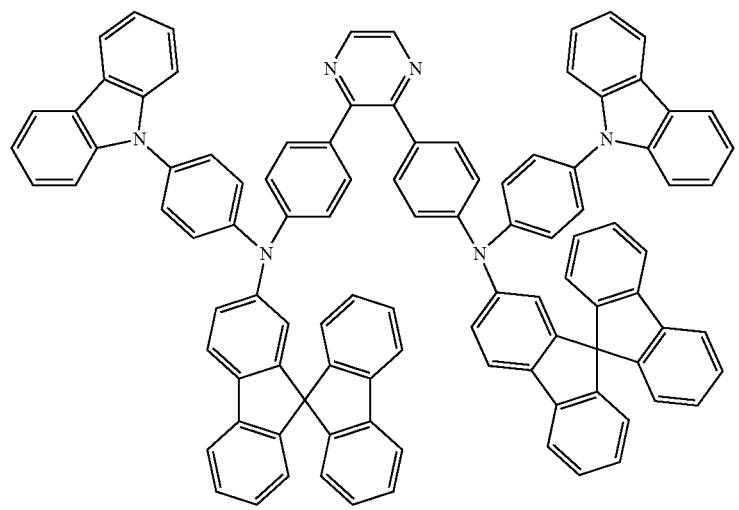
Various reactions can be applied to a synthesis method of a pyrazine derivative of the present invention. For example, a pyrazine derivative can be formed by performing a synthetic reaction shown in the following synthesis scheme (c-1), synthesis scheme (c-2), synthesis scheme (c-3), and synthesis scheme (c-4).
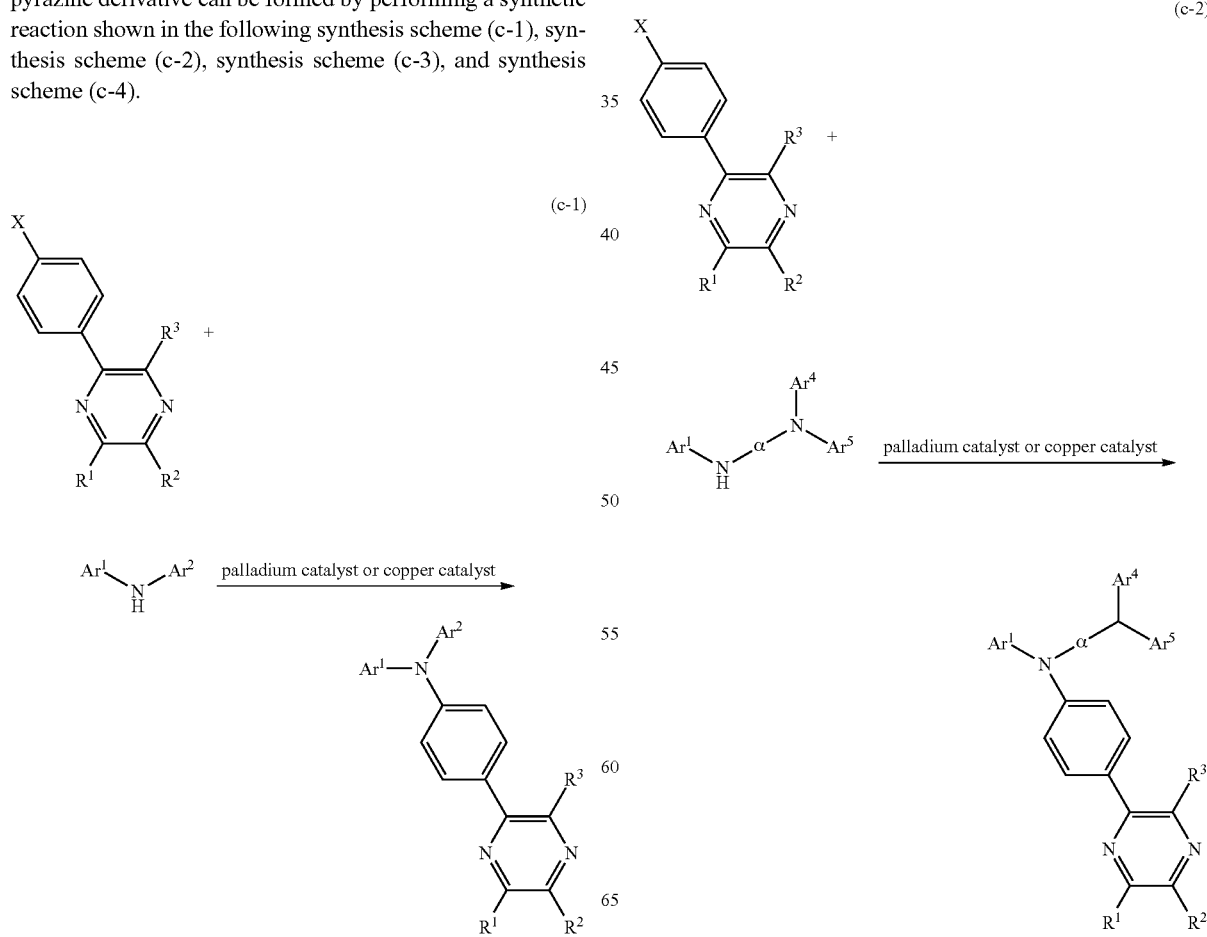

-continued

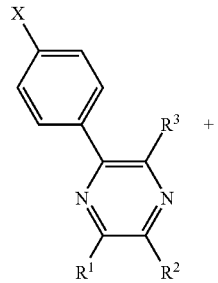

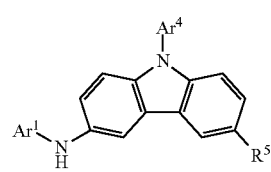 palladium catalyst or copper catalyst ⟶  (c-3)

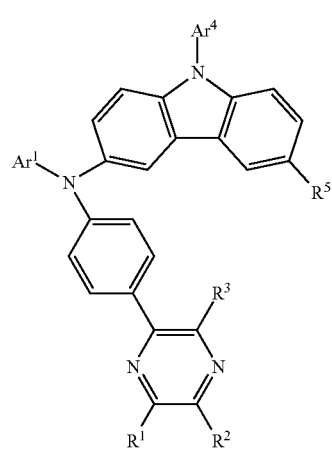

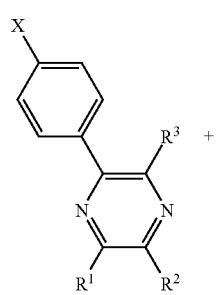

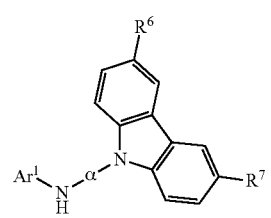 palladium catalyst or copper catalyst ⟶  (c-4)

-continued

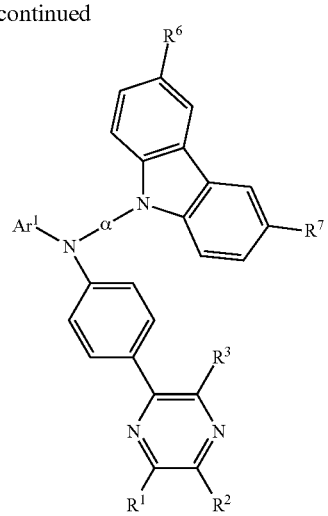

In the above synthesis schemes (c-1) to (c-4), x in the formula represents a halogen atom. Each of $R^1$, $R^2$, and $R^3$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. It is to be noted that the aryl group may have a substituent or be unsubstituted. $R^4$ represents an alkyl group having greater than or equal to 1 and less than or equal to 4 carbon atoms or an aryl group having greater than or equal to 6 and less than or equal to 25 carbon atoms. Each of $R^5$, $R^6$, and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. It is to be noted that the aryl group may have a substituent or be unsubstituted. Each of $Ar^1$ to $Ar^7$ may be same or different, and represents an aryl group having greater than or equal to 6 and less than or equal to 25 carbon atoms. Further, α represents an arylene group having greater than or equal to 6 and less than or equal to 25 carbon atoms. It is to be noted that the arylene group may have a substituent or be unsubstituted.

In the above synthesis scheme (c-1), coupling reaction of a 1 equivalent secondary amine compound is performed with respect to a pyrazine derivative halide by using a palladium catalyst or monovalent copper in the presence of a base, whereby a pyrazine derivative of the present invention can be synthesized. As the base, an inorganic base such as potassium carbonate or sodium carbonate, an organic base such as metal alkoxide, or the like can be used. As the palladium catalyst, palladium acetate, palladium chloride (II), bis(dibenzylideneacetone)palladium(0), or the like can be used.

In the synthesis scheme (c-2), the synthesis scheme (c-3), and the synthesis scheme (c-4), a pyrazine derivative of the present invention can be synthesized by the similar manner to the synthesis scheme (c-1) as explained above. In other words, in each of the synthesis schemes (c-2) to (c-4), coupling reaction of a 1 equivalent secondary amine compound is performed with respect to a pyrazine derivative halide by using a palladium catalyst or monovalent copper in the presence of a base, whereby a pyrazine derivative of the present invention can be synthesized. As the base, an inorganic base such as potassium carbonate or sodium carbonate, an organic base such as a metal alkoxide, or the like can be used. As the palladium catalyst, palladium acetate, palladium chloride (II), bis(dibenzylideneacetone)palladium(0), or the like can be used.

Further, a pyrazine derivative of the present invention can be manufactured, for example, by performing synthetic reaction shown in the following synthesis scheme (d-1), synthesis scheme (d-2), synthesis scheme (d-3), and synthesis scheme (d-4).

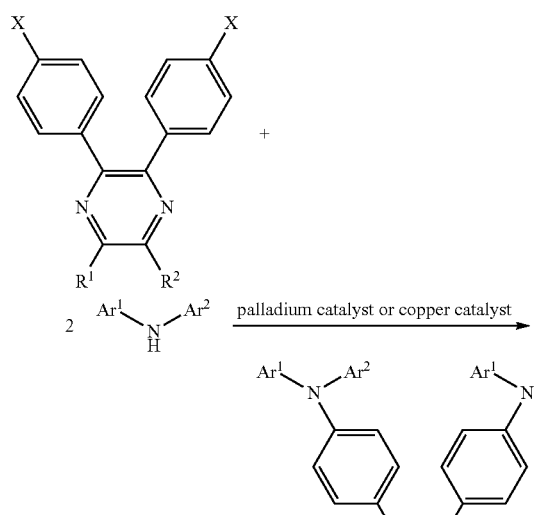

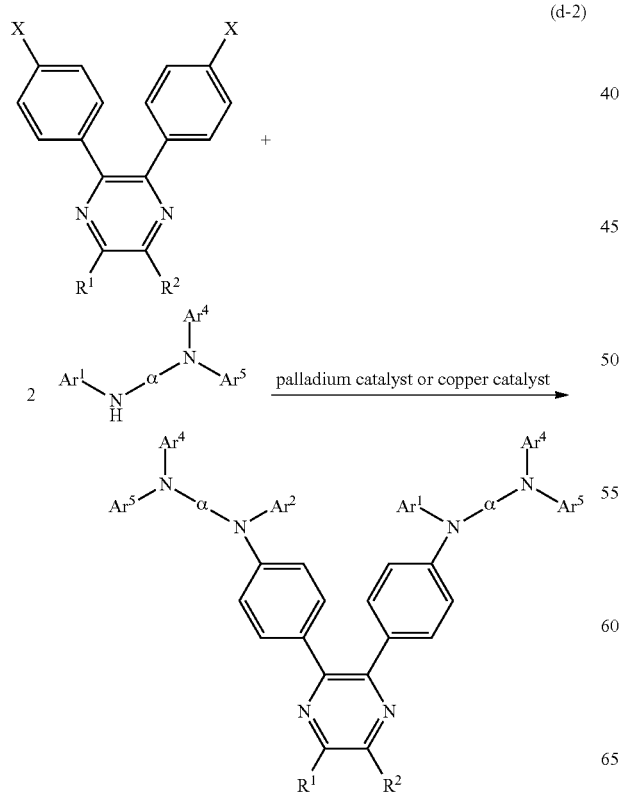

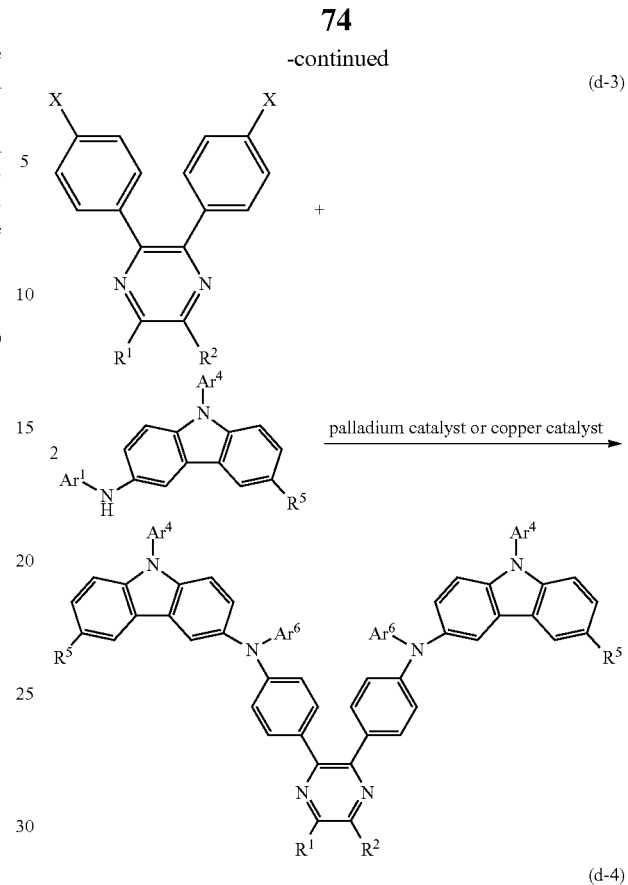

In the above synthesis scheme (d-1), synthesis scheme (d-2), synthesis scheme (d-3), and synthesis scheme (d-4), x in the formula represents a halogen atom. Each of $R^1$ and $R^2$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. It is to be noted that the aryl group may have a substituent or be unsubstituted. $R^4$ represents an alkyl group having greater than or equal to 1 and less than or equal to 4 carbon atoms or an aryl group having greater than or equal to 6 and less than or equal to 25 carbon atoms. Each of $R^5$, $R^6$, and $R^7$ may be same or different, and represents any of a hydrogen atom, an alkyl group having greater than or equal to 1 and less than or equal to 4 carbon atoms, and an aryl group having greater than or equal to 6 and less than or equal to 25 carbon atoms. It is to be noted that the aryl group may have a substituent or be unsubstituted. Each of $Ar^1$ to $Ar^7$ may be same or different, and represents an aryl group having greater than or equal to 6 and less than or equal to 25 carbon atoms. Further, α represents an arylene group having greater than or equal to 6 and less than or equal to 25 carbon atoms.

In the above synthesis scheme (d-1), coupling reaction of a 2 equivalent secondary amine compound is performed with respect to a pyrazine derivative halide by using a palladium catalyst or monovalent copper in the presence of a base, whereby a pyrazine derivative of the present invention can be synthesized. As the base, an inorganic base such as potassium carbonate or sodium carbonate, an organic base such as a metal alkoxide, or the like can be used. As the palladium catalyst, palladium acetate, palladium chloride (II), bis(dibenzylideneacetone)palladium(0), or the like can be used.

In the synthesis schemes (d-2) to (d-4), a pyrazine derivative of the present invention can be synthesized by the similar manner to the synthesis scheme as explained above. In other words, in each of the synthesis schemes (d-2) to (d-4), coupling reaction of a 2 equivalent secondary amine compound is performed with respect to a pyrazine derivative halide by using a palladium catalyst or monovalent copper in the presence of a base, whereby a pyrazine derivative of the present invention can be synthesized. As the base, an inorganic base such as potassium carbonate or sodium carbonate, an organic base such as a metal alkoxide, or the like can be used. As the palladium catalyst, palladium acetate, palladium chloride (II), bis(dibenzylideneacetone)palladium(0), or the like can be used.

It is to be noted that a synthesis method of a pyrazine derivative of the present invention is not limited to the above method, and a pyrazine derivative may be synthesized by another synthesis method.

The pyrazine derivative of the present invention, which is synthesized as the above, is a pyrazine derivative having a bipolar property and superiority in an electron transporting property and a hole transporting property.

Further, a pyrazine derivative of the present invention is a pyrazine derivative that is stable to electrochemical oxidization or reduction.

Embodiment Mode 2

In this embodiment mode, one mode of a light emitting element using a pyrazine derivative of the present invention will be explained with reference to FIG. 1.

A structure of a light emitting element in this embodiment mode has a light emitting layer between a pair of electrodes (an anode and a cathode). A light emitting element of the present invention is provided with a layer between each electrode and the light emitting layer, which is made from a substance having a high hole injecting property or electron injecting property or a substance having a high hole transporting property or electron transporting property. By employing such a structure, a light emitting region is formed in a portion separated from the electrode in the light emitting element of the present invention.

In a light emitting element 100 shown in FIG. 1, a light emitting layer 104 is provided between a first electrode 101 and a second electrode 107. In this embodiment mode, a pyrazine derivative and a phosphorescent compound of the present invention are contained in the light emitting layer 104.

The light emitting element 100 of the present invention has a structure in which a hole injecting layer 102 and a hole transporting layer 103 are sequentially stacked between the first electrode 101 and the light emitting layer 104. In addition, the light emitting element 100 of the present invention has a structure in which an electron transporting layer 105 and an electron injecting layer 106 are sequentially stacked between the light emitting layer 104 and the second electrode 107. It is to be noted that the element structure is not limited to this, and a known structure may be appropriately selected depending on the purpose.

In the light emitting element 100 of the present invention, one of the first electrode 101 and the second electrode 107 becomes an anode, and the other becomes a cathode. The anode indicates an electrode for injecting holes into the light emitting layer, and the cathode indicates an electrode for injecting electrons into the light emitting layer. In this embodiment mode, the first electrode 101 is an anode, and the second electrode 107 is a cathode. Hereinafter, the light emitting element 100 of the present invention will be specifically explained.

As the first electrode 101 (anode), a metal, an alloy, a conductive compound, or a mixture thereof, each of which has a high work function (specifically, 4.0 eV or more), or the like is preferably used. Specifically, a transparent conductive film made from a conductive material having a light transmitting property may be used. For example, indium tin oxide (ITO), indium silicon tin oxide to which silicon oxide is added (ITSO), indium zinc oxide (IZO), or the like can be used. In addition, a metal material such as gold (Au), platinum (Pt), nickel (Ni), tungsten (W), chromium (Cr), zinc (Zn), tin (Sn), indium (In), molybdenum (Mo), iron (Fe), cobalt (Co), copper (Cu), or palladium (Pd) may be used. Further, a nitride of a metal material (such as titanium nitride (TiN)) may be used. The first electrode 101 may be formed of a single layer or a stacked layer of two or more layers of these materials with the use of a sputtering method, an evaporation method, or the like. Moreover, the first electrode 101 may be formed by applying a sol-gel method.

As the hole injecting layer 102, molybdenum oxide (MoOx), vanadium oxide (VOx), ruthenium oxide (RuOx), tungsten oxide (WOx), manganese oxide (MnOx), or the like can be used. In addition, it is possible to use a phthalocyanine-based compound such as phthalocyanine ($H_2Pc$) or copper phthalocyanine (CuPc), a high molecule such as poly(ethylene dioxythiophene)/poly(styrenesulfonic acid) (PEDOT/PSS), or the like.

Alternatively, as the hole injecting layer 102, a composite material including an organic compound and an inorganic compound may be used. As for the inorganic compound included in the composite material, a substance having an electron-accepting property to the organic compound may be used, and specifically, oxide of a transition metal is preferably used. For example, a metal oxide such as titanium oxide ($TiO_x$), vanadium oxide ($VO_x$), molybdenum oxide ($MoO_x$), tungsten oxide ($WO_x$), rhenium oxide ($ReO_x$), ruthenium oxide ($RuO_x$), chromium oxide ($CrO_x$), zirconium oxide ($ZrO_x$), hafnium oxide ($HfO_x$), tantalum oxide ($TaO_x$), silver oxide ($AgO_x$), or manganese oxide ($MnO_x$) can be used. As for the organic compound, a material excellent in a hole transporting property is preferably used. Specifically, an aromatic amine-based organic compound or a carbazole-based organic compound can be used. Alternatively, aromatic hydrocarbon-based organic compound may be used. The composite material including an organic compound and an inorganic compound having an electron-accepting property to the organic compound as the above has superiority in a hole injecting property and a hole transporting property, because carrier density is increased by supplying and accepting electrons between the organic compound and the inorganic compound. Further, by using such a composite material including an organic compound and an inorganic compound having an electron-accepting property to the organic compound as the hole injecting layer 102, ohmic contact between the first electrode 101 and the hole injecting layer 102 becomes possible. As a result, a material for forming the first electrode 101 can be selected regardless of high and low of the work function.

By providing the hole injecting layer 102 to be in contact with the first electrode 101 as the present invention, a hole injecting barrier can be reduced. As a result, a driving voltage of the light emitting element 100 can be reduced.

As the hole transporting layer 103, a substance having a high hole transporting property can be used. Specifically, an aromatic amine-based (that is, one having a bond of benzene ring-nitrogen) compound is preferably used. For example, the following substance can be used: 4,4'-bis[N-(3-methylphenyl)-N-phenylamino]biphenyl, derivatives thereof such as 4,4'-bis[N-(1-naphthyl)-N-phenylamino]biphenyl (hereinafter referred to as NPB), or a star burst aromatic amine compound such as 4,4',4''-tris(N,N-diphenyl-amino)triphenylamine, or 4,4',4''-tris[N-(3-methylphenyl)-N-phenylamino]triphenylamine. The substances described here are a substance mainly having the hole mobility of $10^{-6}$ cm$^2$/Vs or more. However, the present invention is not limited to this, and another substance may be used as long as it has a higher hole transporting property than an electron transporting property. It is to be noted that the hole transporting layer 103 may be formed of a single layer, a mixed layer, or a stacked layer of two or more layers of these materials.

As the light emitting layer 104, a layer containing a pyrazine derivative that is represented by any of the above general formulas (g-1) to (g-14) and a light emitting compound of the present invention is used. Specifically, a light emitting compound is dispersed in a layer made from a pyrazine derivative of the present invention. That is, the pyrazine derivative of the present invention is to be a host material, and the light emitting compound is to be a guest material. By employing such a structure, light emission from the light emitting compound that is the guest material can be obtained, and a light emission color due to the light emitting compound can be obtained. Further, the pyrazine derivative of the present invention serves as a light emitting substance; therefore, a light emission color in which a light emission color due to the light emitting compound and a light emission color due to the pyrazine derivative of the present invention are mixed can be obtained.

As the light emitting compound contained in the light emitting layer 104, a fluorescent compound and a phosphorescent compound can be used. Specifically, a fluorescent compound such as 4-(dicyanomethylene)-2-methyl-6-(p-dimethylaminostyryl)-4H-pyran (abbreviated to DCM1), 4-(dicyanomethylene)-2-methyl-6-(julolidine-4-yl-vinyl)-4H-pyran (abbreviated to DCM2), N,N'-dimethylquinacridone (abbreviated to DMQd), 9,10-diphenylanthracene (abbreviated to DPA), 5,12-diphenyltetracene (abbreviated to DPT), coumarin 6, perylene, or rubrene can be used.

As the phosphorescent compound, a metal complex mainly containing a transition metal such as iridium (Ir) or platinum (Pt), or the like can be used, such as bis(2-phenylbenzothiazolato-N,C$^{2'}$)iridium(III)acetylacetonate (abbreviated to Ir(bt)$_2$(acac)), tris(2-phenylquinolinato-N,C$^{2'}$)iridium(III) (abbreviated to Ir(pa)$_3$), bis(2-phenylquinolinato-N,C$^{2'}$)iridium(III)acetylacetonate (abbreviated to Tr(pq)$_2$(acac)), bis[2-(2'-benzo[4,5-α]thienyl)pyridinato-N,C$^{3'}$]iridium(III) acetylacetonate (abbreviated to Ir(btp)$_2$(acac)), bis(1-phenylisoquinolinato-N,C$^{2'}$)iridium(III)acetylacetonate (abbreviated to Ir(piq)$_2$(acac)), (acetylacetonato)bis[2,3-bis (4-fluorophenyl)quinoxalinato]iridium(III) (abbreviated to Ir(Fdpq)$_2$(acac)), or 2,3,7,8,12,13,17,18-octaetyl-21H,23H-porphyrinplatinum(II) (abbreviated to PtOEP).

As the electron transporting layer 105, a substance having a high electron transporting property can be used. For example, it is possible to use a metal complex having a quinoline skeleton or a benzoquinoline skeleton or the like, such as tris(8-quinolinolato)aluminum (abbreviated to Alq$_3$), tris(4-methyl-8-quinolinolato)aluminum (abbreviated to Almq$_3$), bis(10-hydroxybenzo[h]-quinolinato)beryllium (abbreviated to BeBq$_2$), or bis(2-methyl-8-quinolinolato)-4-phenylphenolato-aluminum (abbreviated to BAlq). Alternatively, a metal complex having an oxazole-based or a thiazole-based ligand, such as bis[2-(2-hydroxyphenyl)-benzoxazolato]zinc (abbreviated to Zn(BOX)$_2$) or bis[2-(2-hydroxyphenyl)-benzothiazolato]zinc (abbreviated to Zn(BTZ)$_2$) can be used. Further, other than the metal complexes, 2-(4-biphenylyl)-5-(4-tert-butylphenyl)-1,3,4-oxadiazole (abbreviated to PBD), 1,3-bis [5-(p-tert-buthylphenyl)-1,3,4-oxadiazol-2-yl]benzene (abbreviated to OXD-7), 3-(4-tert-butylphenyl)-4-phenyl-5-(4-biphenylyl)-1,2,4-triazole (abbreviated to TAZ), 3-(4-tert-butylphenyl)-4-(4-ethylphenyl)-5-(4-biphenylyl)-1,2,4-triazole (abbreviated to p-EtTAZ), bathophenanthroline (abbreviated to BPhen), bathocuproin (abbreviated to BCP), or the like may be used. The substances described here are a substance mainly having the electron mobility of $10^{-6}$ cm$^2$/Vs or more. However, the present invention is not limited to this, and another substance may be used as long as it has a higher electron transporting property than a hole transporting property. It is to be noted that the electron transporting layer 105 may be formed of a single layer, a mixed layer, a stacked layer of two or more layers of these materials.

As the electron injecting layer 106, a compound of an alkali metal or an alkaline earth metal, such as lithium fluoride (LiF), cesium fluoride (CsF), or calcium fluoride (CaF$_2$) can be used. In addition, a layer made from a substance having an electron transporting property may be used, in which an alkali metal, an alkaline earth metal, an alkali metal compound, or an alkaline earth metal compound is contained. For example, Alq$_3$ containing lithium oxide (LiO$_x$), magnesium nitride (MgO$_x$), magnesium (Mg), or lithium (Li) can be used. By providing the electron injecting layer 106 to be in contact with the second electrode 107 as the present invention, an electron injecting barrier can be reduced. As a result, a driving voltage of the light emitting element 100 can be reduced.

As the second electrode 107 (cathode), a metal, an alloy, an electric conductive compound, a mixture thereof, each of which has a low work function (specifically, work function of 3.8 eV or lower), or the like, can be used. As a specific example, an element belonging to Group 1 or Group 2 in the periodic table, that is, an alkali metal such as lithium (Li) or cesium (Cs), an alkaline earth metal such as magnesium (Mg), calcium (Ca), or strontium (Sr), an alloy containing any of these (such as MgAg or AlLi), a rare earth metal such as europium (Eu) or ytterbium (Yb), an alloy containing any of these, or the like may be used. By providing the electron injecting layer 106 to be in contact with the second electrode 107 between the second electrode 107 and the light emitting layer 104, various conductive materials such as Al, Ag, ITO, or ITSO can be used as the second electrode 107 regardless of high and low of the work function.

The hole injecting layer 102, the hole transporting layer 103, the light emitting layer 104, the electron transporting layer 105, and the electron injecting layer 106 may be formed by an evaporation method. In addition, an inkjet method, a spin coating method, or the like may be used. Further, each electrode and each layer may be formed by different formation methods.

In the light emitting element 100 of the present invention having the above structure, a current flows due to a potential difference that is generated between the first electrode 101 and the second electrode 107, and holes and electrons are recombined in the light emitting layer 104, whereby light is emitted.

Light emission of the light emitting element 100 of the present invention can be extracted from one or both of the first electrode 101 side and the second electrode 107 side by selecting the material of the first electrode 101 and the second electrode 107. For example, the first electrode 101 has a light transmitting property, and the second electrode 107 has a light shielding property (a reflecting property), whereby light can be extracted from the first electrode 101 side. Alternatively, the first electrode 101 has a light shielding property (a reflective property), and the second electrode 107 has a light transmitting property, whereby light can be extracted from the second electrode 107 side. Alternatively, the first electrode 101 and the second electrode 107 have a light transmitting property, whereby light can be extracted from both electrodes side.

The light emitting element of this embodiment mode is not limited to the above structure as long as the light emitting element has a structure in which at least the light emitting layer 104 is provided between the first electrode 101 and the second electrode 107. Accordingly, the structure of the light emitting element may be appropriately changed depending on the purpose.

Although the first electrode 101 is set to be an anode in this embodiment mode, the present invention is not limited thereto, and the first electrode 101 may be set to be a cathode. In a case where the first electrode is set to be a cathode, an electron injecting layer in contact with the cathode, an electron transporting layer, a light emitting layer, a hole transporting layer, a hole injecting layer, and the second layer 107 that is to be an anode may be sequentially stacked. Also, in this case, a structure of the light emitting element can be appropriately changed depending on the purpose as long as the light emitting element has a structure in which the light emitting layer is provided between the first electrode 101 and the second electrode 107.

In the light emitting element 100 of the present invention, a pyrazine derivative of the present invention, which has a bipolar property, is used as a host material. As a result, light emission from a light emitting compound that is a guest material can be efficiently obtained. In particular, light emission in a case of using a phosphorescent compound as the guest material can be efficiently obtained.

Embodiment Mode 3

In this embodiment, a light emitting element that has a different structure from the structure shown in Embodiment Mode 2 will be explained. It is to be noted that the structure except for the light emitting layer is the same as that of Embodiment Mode 2; therefore, explanation thereof is omitted.

Figure 2:
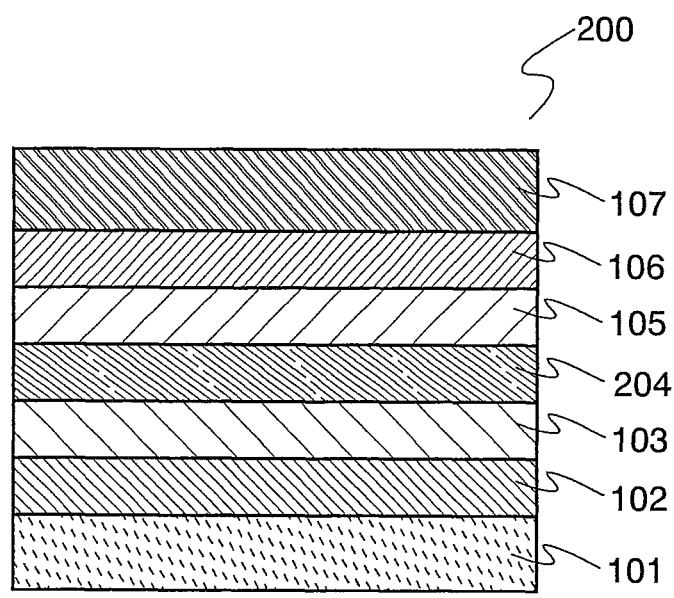
FIG. 2 is a view showing an example of a light emitting element of the present invention.

In a light emitting element 200 of the present invention shown in FIG. 2, a light emitting layer 204 is provided between a first electrode 101 and a second electrode 107, which is similar to the light emitting element shown in Embodiment Mode 1. It is to be noted that an element structure is not limited to that shown in FIG. 2. The element structure may be appropriately selected from the known structure depending on the purpose as long as the structure has at least a pair of electrodes (the first electrode 101 and the second electrode 107) and a light emitting layer provided between the pair of the electrodes.

In the light emitting element 200 of this embodiment mode, a layer containing only a pyrazine derivative of the present invention, which is represented by any of the above general formulas (g-1) to (g-14), is used as the light emitting layer 204. A pyrazine derivative of the present invention, in which blue to green light emission colors can be obtained, can be favorably used in the light emitting element as a light emitting compound.

Further, a pyrazine derivative of the present invention may be used as a guest material and dispersed into a host material. As the host material to which the pyrzine derivative of the present invention is dispersed, one having larger energy gap than that of the pyrazine derivative of the present invention may be used. Specifically, 9,10-di(2-naphthyl)anthracene (abbreviated to DNA), 2-tert-butyl-9,10-di(2-naphthyl)anthracene (abbreviated to t-BuDNA), or the like can be used.

As described above, the pyrazine derivative of the present invention has a bipolar property and serves as the light emitting compound. Accordingly, the pyrazine derivative of the present invention can be used as a material of the light emitting layer 204 without containing another light emitting compound.

Since the pyrazine derivative of the present invention has a bipolar property, a light emitting region is rarely located at an interface of a stacked film. Accordingly, a light emitting element, which has change of a light emission spectrum due to mutual action such as exciplex and a favorable characteristic of small decrease of light emitting efficiency, can be obtained.

Embodiment Mode 4

In this embodiment mode, one example of a display device of the present invention and a manufacturing method thereof will be explained with reference to FIGS. 3A and 3B and FIG. 4. In this embodiment mode, an example of an active matrix display device in which a pixel portion 370 and a driver circuit portion 380 are formed over a same substrate will be explained.

First, a base insulating film 301 is formed over a substrate 300. When light is extracted from the substrate 300 side as a display surface, a glass substrate or a quartz substrate each of which has a light transmitting property may be used as the substrate 300. In addition, a light-transmitting plastic substrate that has resistance to a processing temperature may be used. When light is extracted from an opposite surface to the substrate 300 side as a display surface, a silicon substrate, a metal substrate, or a stainless substrate over which an insulating film is formed may be used in addition to the above substrate. At least a substrate that can resist heat generated during a process may be used. In this embodiment mode, a glass substrate is used for the substrate 300. A reflective index of the glass substrate is approximately 1.55.

The base insulating film 301 is formed using an insulating film such as a silicon oxide film, a silicon nitride film, or a silicon oxynitride film by a sputtering method, an LPCVD method, a plasma CVD method, or the like to have a single layer or a multi-layer of two or more layers. Further, the base insulating film is not necessary to be formed unless unevenness of the substrate and diffusion of an impurity from the substrate become a problem.

Next, a semiconductor layer is formed over the base insulating film 301. After an amorphous semiconductor film is formed by a sputtering method, an LPCVD method, a plasma CVD method, or the like, the semiconductor film is crystallized by a laser crystallization method, a thermal crystallization method, a thermal crystallization method using a catalytic element such as nickel to obtain a crystalline semiconductor film. In a case where a thermal crystallization method using a catalytic element such as nickel is used, the catalytic element is preferably removed by gettering after the crystallization. Thereafter, the crystalline semiconductor film is formed into a desired shape by a photolithography method.

Subsequently, a gate insulating film 302 covering the semiconductor layer is formed. As for the gate insulating film 302, an insulating film containing silicon is formed with the use of a plasma CVD method or a sputtering method. Alternatively, the gate insulating film 302 may be formed by performing surface nitriding treatment using plasma by a microwave after an insulating film containing silicon that has a single-layer structure or a stacked-layer structure is formed.

Then, a gate electrode is formed over the gate insulating film 302. The gate electrode may be formed using a conductive material of a refractory metal such as tungsten (W), chromium (Cr), tantalum (Ta), tantalum nitride (TaN), or molybdenum (Mo), or a conductive material of an alloy or a compound containing the refractory metal as its main component, or the like by a sputtering method, an evaporation method, or the like. The gate electrode may have a single-layer structure or a multi-layer of two or more layers of these conductive materials.

Then, an impurity is added to each semiconductor layer in transistors 310, 330, and 340 that are formed in the pixel portion 370 and the driver circuit portion 380, in order to form an impurity region having n-type or p-type conductivity. The impurity that is added may be appropriately selected in accordance with each transistor.

Next, first interlayer insulating films 303a, 303b, and 303c are formed. As the first interlayer insulating films 303a, 303b, and 303c, an inorganic insulating film such as a silicon oxide film, a silicon nitride film, or a silicon oxynitride film, an organic resin film, or a film containing siloxane can be used, and these insulating films may be formed to have a single layer or a multi-layer of two or more layers. It is to be noted that siloxane is a material having a skeleton structure of a bond of silicon (Si) and oxygen (O). As a substituent, an organic group containing at least hydrogen (for example, an alkyl group having greater than or equal to 1 and less than or equal to 4 carbon atoms or aromatic hydrocarbon) can be used. In addition, a fluoro group may be used as the substituent. Further, as the substituent, an organic group containing at least hydrogen and a fluoro group may be used. When an inorganic insulating film is formed, a sputtering method, an LPCVD method, a plasma CVD method, or the like may be used. When an organic resin film or a film containing siloxane is formed, a coating method may be used. Although the first interlayer insulating films 303a, 303b, and 303c have a three stacked-layer structure here, the interlayer insulating film may have a single layer or a multi-layer.

Subsequently, the first interlayer insulating films 303a, 303b, and 303c are selectively etched to form a contact hole that reaches the semiconductor layer. Then, a source electrode and a drain electrode that reach a semiconductor layer through the contact hole are formed. After a metal film is stacked by a sputtering method, the source electrode and the drain electrode are formed by selective etching of the metal stacked film by a photolithography method.

Through the above steps, the transistor 310 connected to a light emitting element, a capacitor 311, a capacitor 311, and the transistor 330 and the transistor 340 that are arranged in the driver circuit portion are formed. In this embodiment mode, in order to reduce an off-current, the transistor 310 connected to the light emitting element has a multi-gate structure (a structure that has a semiconductor layer including two or more channel formation regions connected in series and two or more gate electrodes applying an electric field to each channel formation region). It is to be noted that the present invention is not limited to this, and a single-gate structure such as the transistor 330 and the transistor 340 may be employed. Although the transistor 330 and the transistor 340 that are arranged in the driver circuit portion have the single-gate structure, the present invention is not limited to this, and a multi-gate structure may be employed.

Further, each of the transistor 310, the transistor 330, and the transistor 340 has a structure having a low concentration impurity region (LDD region) that is overlapped with the gate electrode through the gate insulating film 302. It is to be noted that the present invention is not limited to this, and a structure without an LDD region may be employed.

In the pixel portion 370, a transistor 320 serving as a switching element is provided as shown in FIG. 3B. The transistor 320 has a structure having a low concentration impurity region (LDD region) that is not overlapped with the gate electrode through the gate insulating film 302. It is to be noted that the present invention is not limited to this, and a structure without an LDD region may be employed.

In the driver circuit portion 380, the transistor 330 is set to be an n-channel, the transistor 340 is set to be a p-channel, and the transistor 330 and the transistor 340 are complementary connected, whereby a CMOS circuit can be formed. By employing such a structure, various types of a circuit can be achieved.

Next, a second interlayer insulating film 304 is formed over the first interlayer insulating films 303a, 303b, and 303c. As the second interlayer insulating film 304, an inorganic insulating film such as a silicon oxide film, a silicon nitride film, or a silicon oxynitride film can be formed. Alternatively, an organic resin film such as acryl or polyimide, or a film containing siloxane may be used. Then, these insulating films may be formed of a single layer or a multi-layer of two or more layers. It is to be noted that siloxane is a material having a skeleton structure of a bond of silicon (Si) and oxygen (O). As a substituent, an organic group containing at least hydrogen (for example, an alkyl group having greater than or equal to 1 and less than or equal to 4 carbon atoms or aromatic hydrocarbon) can be used. In addition, a fluoro group may be used as the substituent. Further, as the substituent, an organic group containing at least hydrogen and a fluoro group may be used. When an inorganic insulating film is formed, a sputtering method, an LPCVD method, a plasma CVD method, or the like may be used. When an organic resin film or a film containing siloxane is formed, a coating method may be used. Although the second interlayer insulating film 304 has a single layer here, it may have a multi-layer. When an organic resin film, a film containing siloxane, or the like is used as the second interlayer insulating film 304, the second interlayer insulating film 304 preferably has a stacked-layer structure including an inorganic insulating film of a silicon oxide film, a silicon nitride film, and the like.

Subsequently, a light emitting element 350 is formed. First, a first electrode 351 (an anode or a cathode of an organic light emitting element) is formed. The first electrode 351 is electrically connected to the first transistor 310 through the second interlayer insulating film 304. It is to be noted that the first electrode 351 may be formed in the similar manner to Embodiment Mode 2 and Embodiment Mode 3, and explanation thereof is omitted.

Then, a partition layer 305 covering an edge portion of the first electrode 351 is formed. As for the partition layer 305, an insulating film such as acryl, siloxane, resist, silicon oxide, or polyimide is formed by a coating method, and the obtained insulating film may be formed into a desired shape by a photolithography method.

Then, a layer 352, and a second electrode 353 (a cathode or an anode of the light emitting element) are sequentially formed. It is to be noted that the layer 352 includes a layer containing a pyrazine derivative of the present invention represented by any of the general formulas (g-1) to (g-14), which is explained in Embodiment Mode 2 or Embodiment Mode 3. The layer 352 includes at least a light emitting layer. In addition, a hole injecting layer, a hole transporting layer, an electron transporting layer, an electron injecting layer, or the like may be included. The layer 352 and the second electrode 353 may be formed in a similar manner to Embodiment Mode 2 and Embodiment Mode 3, and explanation thereof is omitted.

Through the above steps, the light emitting element 350 including the first electrode 351, the layer 352, and the second electrode 353 is formed. The light emitting element 350 is separated from another adjacent light emitting element by the partition layer 305.

Next, a sealing substrate 360 is sealed with a sealant 306 to seal the light emitting element 350. In other words, a periphery of a display region is surrounded by the sealant 306, and a display device is sealed with a pair of the substrates 300 and 360. Although the sealant 306 is provided over the driver circuit portion 380 in this embodiment, the sealant 306 may be provided to surround at least the periphery of the display device. A space 307 surrounded by the sealant 306 may be filled with filler or a dried inert gas.

Finally, an FPC 393 is attached to a terminal electrode 391 with an anisotropic conductive layer 392 to constitute a terminal portion 390. In the terminal electrode 391, an electrode is preferably provided in an uppermost layer, which is obtained by the same step as that of a wiring electrically connecting the transistor 310 and the first electrode 351 to each other.

Figure 4:
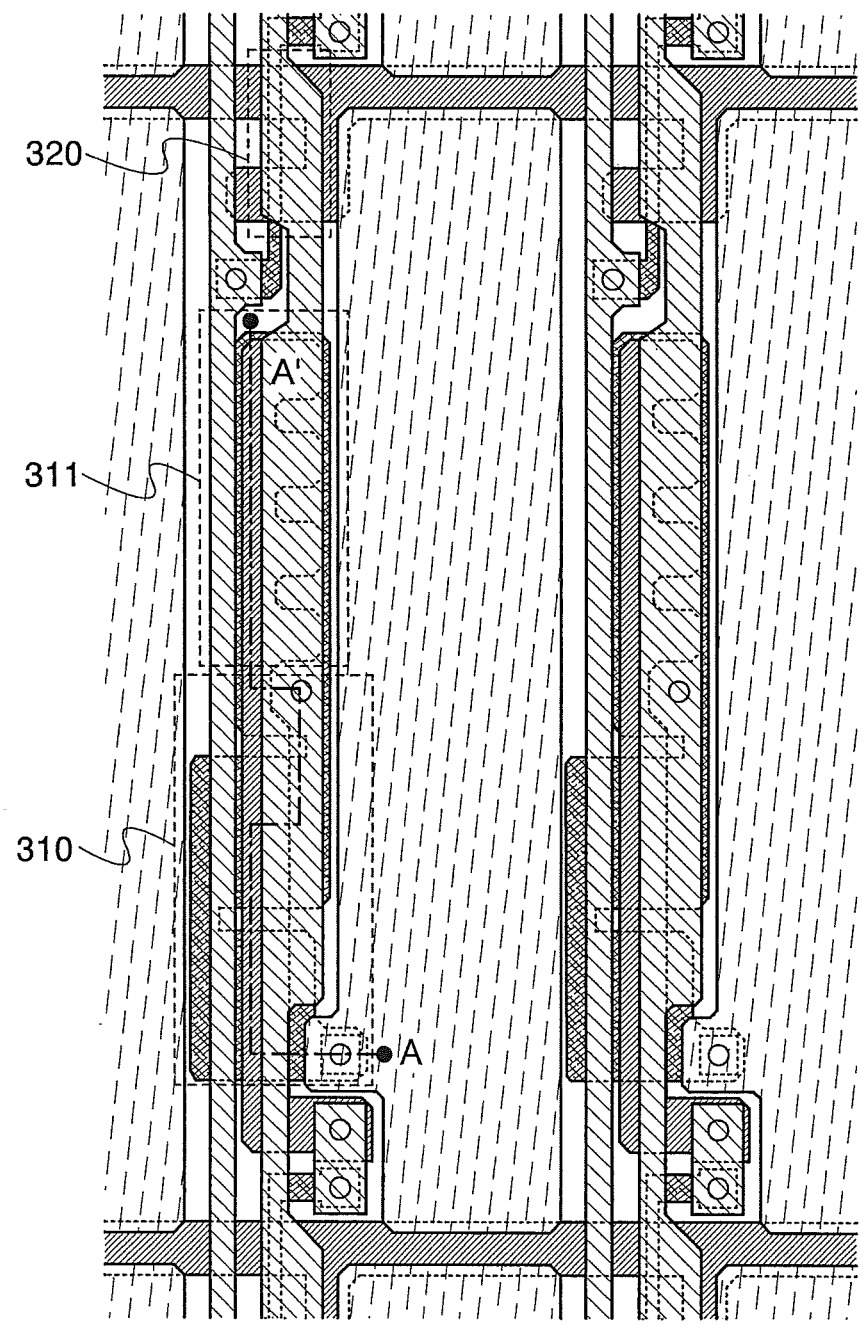
FIG. 4 is a top view showing an example of a pixel portion in a display device of the present invention.

FIG. 4 shows a top view of the pixel portion. A cross-section of a portion shown by a dashed line A-A' in FIG. 4 corresponds to a cross-sectional view of the pixel portion 370 in FIG. 3A. Although the partition layer 305 covering an edge portion of the first electrode 351 of the light emitting element, the layer 352, the second electrode 353, the sealing substrate 360, and the like are not shown in FIG. 4, they are actually provided. FIGS. 3A and 3B and FIG. 4 are views showing one example of a display device of the present invention, and a wiring or the like is appropriately changed depending on a layout.

In a display device of the present invention, a light emission display surface of the display device may be one surface or both surfaces. When the first electrode 351 and the second electrode 353 are formed of a transparent conductive film, light from the light emitting element 350 is extracted to both surface sides through the substrate 300 and the sealing substrate 360. In this case, a transparent material is preferably used for the sealing substrate 360 and the filler.

When the second electrode 353 is formed of a metal film, and the first electrode 351 is formed of a transparent conductive film, light from the light emitting element 350 is extracted to one surface side through only the substrate 300. That is, a bottom emission structure is made. In this case, a transparent material is not necessary to be used for the sealing substrate 360 and the filler.

When the first electrode 351 is formed of a metal film, and the second electrode 353 is fog led of a transparent conductive film, light from the light emitting element 350 is extracted to one surface side through only the sealing substrate 360. That is, a top emission structure is made. In this case, a transparent material is not necessary to be used for the substrate 300.

For the first electrode 351 and the second electrode 353, a material is needed to be selected in consideration of the work function. However, both the first electrode 351 and the second electrode 353 may be an anode or a cathode depending on a pixel structure. When polarity of the transistor 310 is a p-channel, the first electrode 351 is an anode, and the second electrode 353 is a cathode. Alternatively, when polarity of the transistor 310 is an n-channel, the first electrode 351 is a cathode, and the second electrode 353 is an anode.

Figure 5:
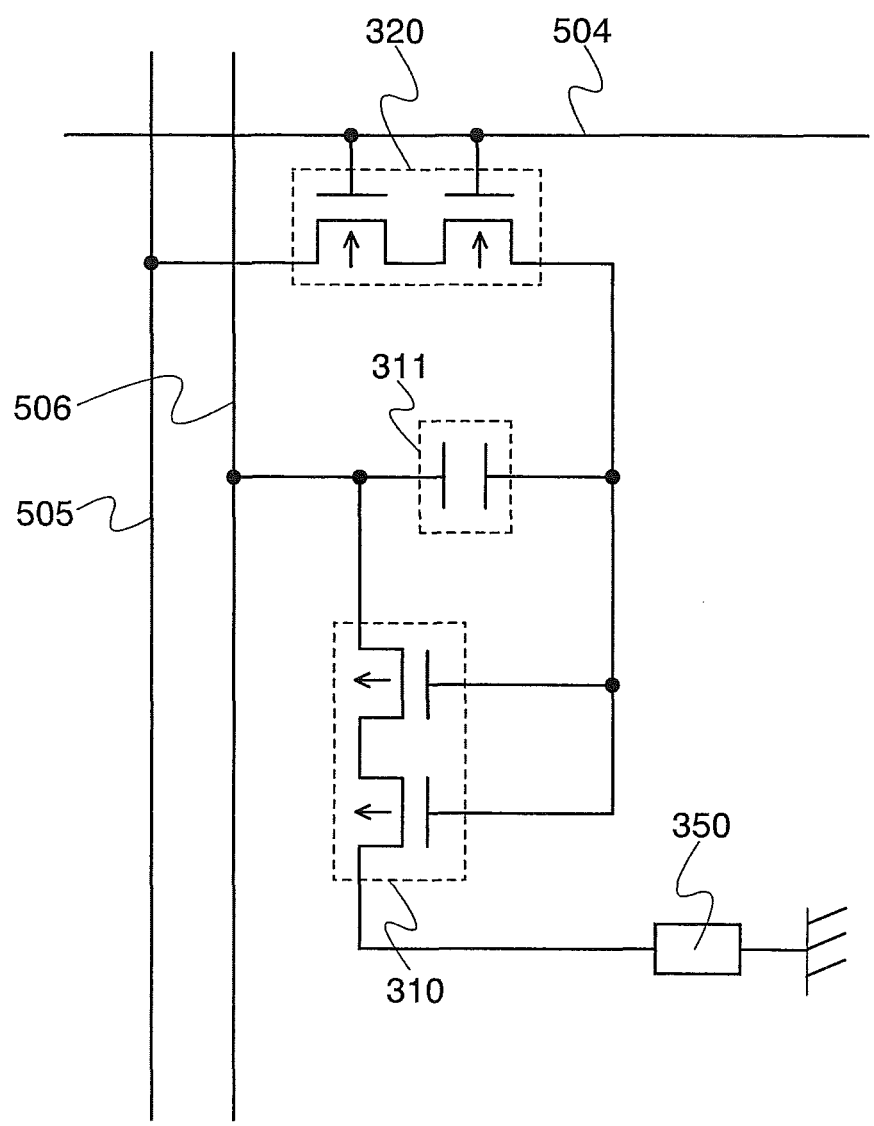
FIG. 5 is a circuit diagram showing an example of a pixel portion in a display device of the present invention.

A connection relation of the transistors 310 and 320, the capacitor 311, and the like is shown in a circuit diagram of FIG. 5. A gate electrode of the transistor 320 is connected to a gate line 504, and one of a source region and a drain region of the transistor 320 is connected to a source line 505. The other of a source region and a drain region of the transistor 310 is connected to a current supply line 506.

When the light emitting element 350 is a diode type element, and the transistor 310 connected to the light emitting element 350 in series as this embodiment is a p-channel transistor, the first electrode 351 of the light emitting element 350 serves as an anode. On the other hand, when the transistor 310 is an n-channel transistor, the first electrode 351 of the light emitting element 350 serves as a cathode.

In the pixel portion of the display device of the present invention, a plurality of light emitting elements driven by the circuit shown in FIG. 5 is arranged in matrix. A circuit for driving the light emitting element is not limited to the circuit shown in FIG. 5. For example, a circuit may have a structure in which an erasing transistor that is used for an erasing line and erasing operation for forcibly erasing an input signal is provided or the like.

By including a light emitting element containing a pyrazine derivative of the present invention as in this embodiment mode, a display device emitting light efficiently can be obtained.

Embodiment Mode 5

Figure 6A:
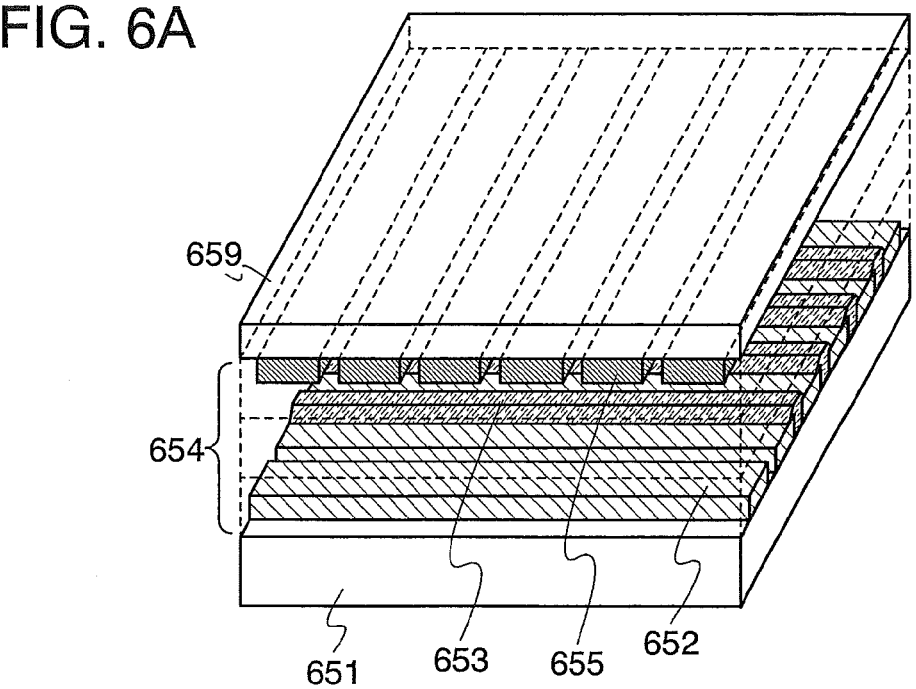
FIGS. 6A and 6B are views each showing an example of a display device of the present invention.
Figure 6B:
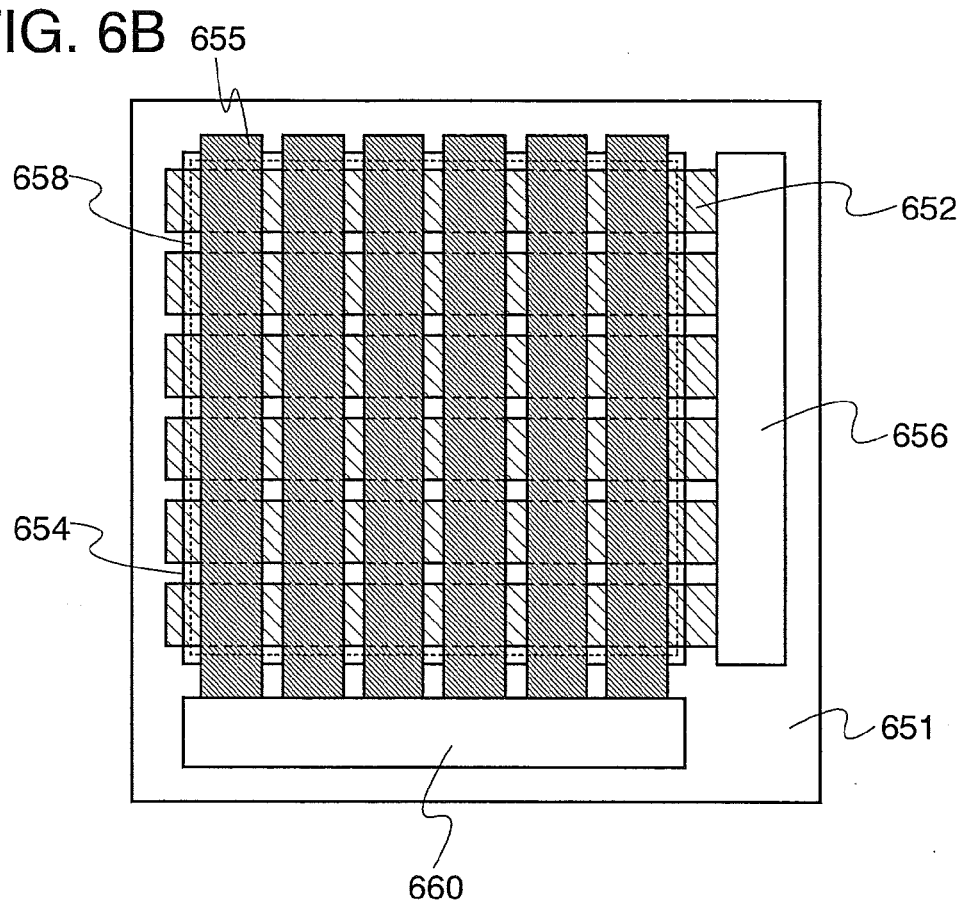

In this embodiment mode, an example of a passive display device will be explained with reference to FIGS. 6A and 6B. FIG. 6A and FIG. 6B respectively show a perspective view and a top view of a passive display device to which the present invention is applied. In particular, FIG. 6A is a perspective view of a portion surrounded by a dot line 658 of FIG. 6B. Corresponding portions in each of FIG. 6A and FIG. 6B are denoted by the same reference numerals. In FIG. 6A, a plurality of first electrodes 652 is arranged in parallel over a first substrate 651. Each edge portion of the first electrodes 652 is covered with a partition layer 653. In order to easily recognize a state where the first electrode over the first substrate 651 and the partition layer 653 are arranged, a partition layer that covers the first electrode 652 provided on the most front side is not shown in FIG. 6A. However, an edge portion of the first electrode 652 provided on the most front side is actually covered with the partition layer. A plurality of second electrodes 655 is provided in parallel above the first electrodes 652, so as to intersect with the plurality of the first electrodes 652. A layer 654 is provided between the first electrode 652 and the second electrode 655. It is to be noted that the layer 654 includes a layer containing a pyrazine derivative of the present invention, which is explained in Embodiment Mode 2 or Embodiment Mode 3. The layer 654 includes at least a light emitting layer. In addition, a hole injecting layer, a hole transporting layer, an electron transporting layer, an electron injecting layer, or the like may be included. A second substrate 659 is provided over the second electrode 655.

As shown in FIG. 6B, the first electrode 652 is connected to a first driver circuit 656, and the second electrode 655 is connected to a second driver circuit 660. A portion where the first electrode 652 and the second electrode 655 are intersected with each other forms a light emitting element of the present invention, which is formed by interposing the light emitting layer between the electrodes. Then, the light emitting element of the present invention, which is selected by a signal from the first driver circuit 656 and the second driver circuit 660, emits light. Light emission is extracted to outside through the first electrode 652, the second electrode 655, or the first electrode 652 and the second electrode 655. Light emission from the plurality of the light emitting elements is combined to reflect an image. In order to easily recognize each arrangement of the first electrode 652 and the second electrode 655, the partition layer 653 and the second substrate 659 are not shown in FIG. 6B. However, they are actually provided as shown in FIG. 6A.

Although materials for forming the first electrode 652 and the second electrode 655 are not particularly limited, a transparent conductive film is preferably used so that one of or both the electrodes can transmit visible light. Materials for the first substrate 651 and the second substrate 659 are not particularly limited, and each substrate may be formed using a material having flexibility with a resin such as plastic, in addition to a glass substrate or the like. A material of the partition layer 653 is not particularly limited, and either an inorganic insulating film or an organic insulating film may be used. Alternatively, both the inorganic insulating film and the organic insulating film may be used. In addition, the partition layer 653 may be formed using siloxane.

It is to be noted that the layers 654 may be independently provided for each light emitting element exhibiting light emission with different color. For example, by providing independently the layers 654 for each light emitting element emitting light with a red color, a green color, and a blue color, a display device capable of multi-color display can be obtained.

By including a light emitting layer containing a pyrazine derivative of the present invention as in this embodiment mode, a passive display device emitting light efficiently can be obtained.

Embodiment Mode 6

In this embodiment mode, a module using a panel that includes the display device of the present invention as shown in Embodiment Mode 4 will be explained with reference to FIGS. 7A and 7B.

Figure 7A:
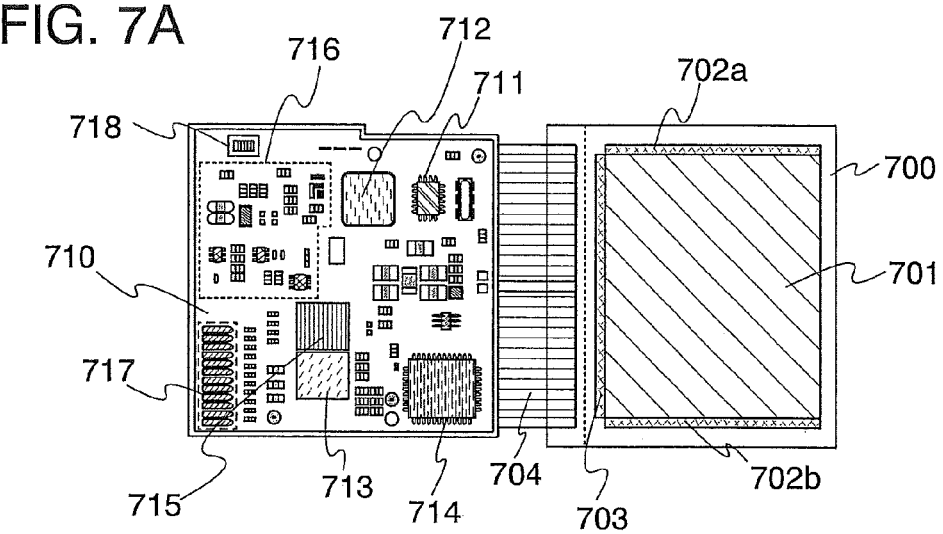
FIGS. 7A and 7B are views each showing an example of a panel provided with a display device of the present invention.

FIG. 7A shows a module of an information terminal. In a panel 700, a pixel portion 701 in which light emitting elements are provided in each pixel, a first scanning line driver circuit 702a and a second scanning line driver circuit 702b that select a pixel included in the pixel portion 701, and a signal line driver circuit 703 that supplies a video signal to a selected pixel are provided. The pixel portion 701 corresponds to the pixel portion or the like in FIGS. 3A and 3B and FIG. 4 explained in Embodiment 4.

A printed wiring board 710 is connected to the panel 700 through an FPC (flexible printed circuit) 704. A controller 711, a CPU (central processing unit) 712, a memory 713, a power supply circuit 714, an audio processing circuit 715, and a transmission-reception circuit 716 are mounted on the printed wiring board 710 in addition to an element such as a resistor, a buffer, or a capacitor element.

Various control signals are input and output through an interface (I/F) portion 717 provided over the printed wiring board 710. In addition, an antenna port 718 for transmitting and receiving signals to/from an antenna is provided over the printed wiring board 710.

Although the printed wiring board 710 is connected to the panel 700 through the FPC 704 in this embodiment mode, the present invention is not limited thereto. With the use of a COG (Chip on Glass) method, the controller 711, the audio processing circuit 715, the memory 713, the CPU 712, or the power supply circuit 714 may be directly mounted on the panel 700. Further, various elements such as the capacitor element and the buffer are provided over the printed wiring board 710, thereby preventing a noise in a power supply voltage or a signal and a dulled rise of a signal.

Figure 7B:
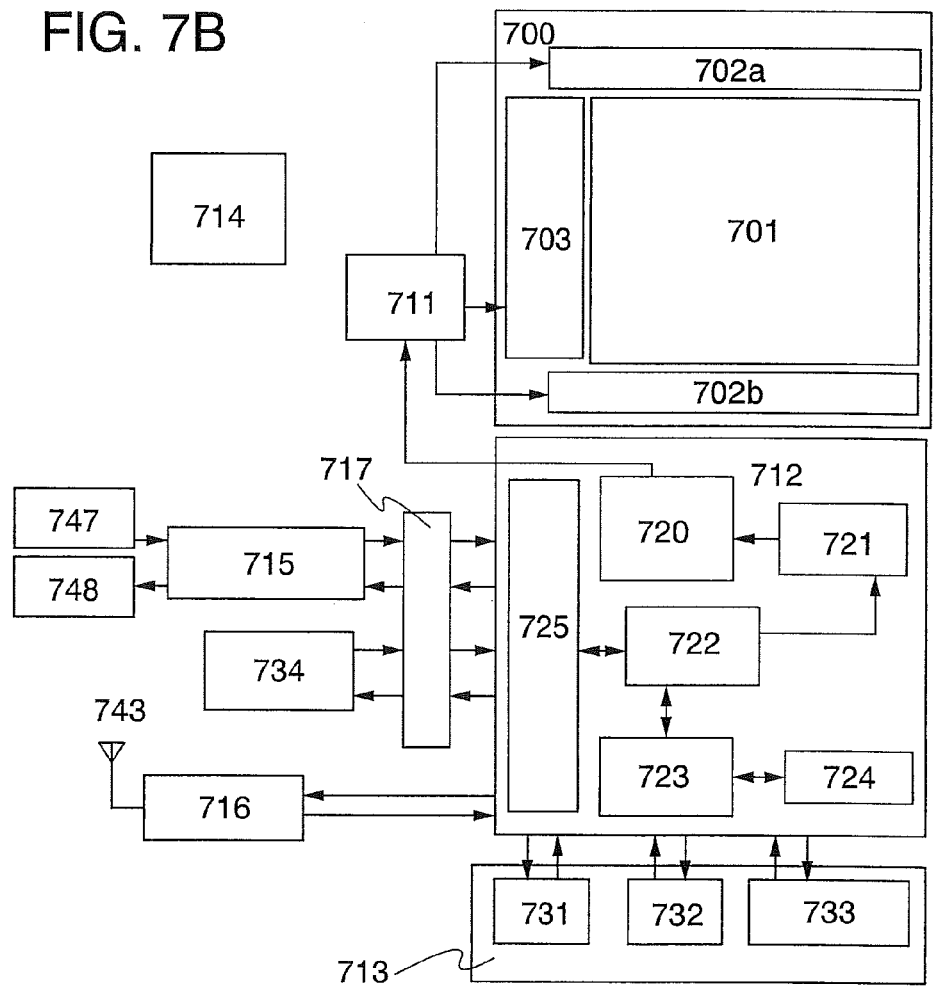

FIG. 7B shows a block diagram of the module shown in FIG. 7A. This module includes, as the CPU 712, a control signal generating circuit 720, a decoder 721, a register 722, an arithmetic circuit 723, a RAM 724, an interface 725 for the CPU, and the like. Various signals input to the CPU 712 through the interface 725 are input to the arithmetic circuit 723, the decoder 721, or the like after being once held in the register 722. The arithmetic circuit 723 operates based on the input signal and specifies an address to send various instructions. Meanwhile, a signal input to the decoder 721 is decoded and input to the control signal generating circuit 720. The control signal generating circuit 720 generates a signal including various instructions based on the input signal and sends it to the address specified by the arithmetic circuit 723, which is specifically the memory 713, the transmission-reception circuit 716, the audio processing circuit 715, the controller 711, or the like.

As the memory 713, a VRAM 731, a DRAM 732, a flash memory 733, or the like are provided. The VRAM 731 stores image data displayed on the panel 700, the DRAM 732 stores image data or audio data, and the flash memory 733 stores various programs.

The power supply circuit 714 generates a power supply voltage that is applied to the panel 700, the controller 711, the CPU 712, the audio processing circuit 715, the memory 713, and the transmission-reception circuit 716. A current source may be provided in the power supply circuit 714 depending on the specification of the panel.

The memory 713, the transmission-reception circuit 716, the audio processing circuit 715, and the controller 711 operate in accordance with respective received instructions. Hereinafter, the operation is briefly explained.

A signal input from an input unit 734 is transmitted to the CPU 712 mounted on the printed wiring board 710 through the interface (I/F) portion 717. The control signal generating circuit 720 converts the image data stored in the VRAM 731 into a predetermined format in accordance with the signal transmitted from the input unit 734 such as a pointing device or a keyboard, and then transmits it to the controller 711.

The controller 711 processes a signal including the image data that is transmitted from the CPU 712 in accordance with the specification of the panel and supplies it to the panel 700. The controller 711 generates and supplies a Hsync signal, a Vsync signal, a clock signal CLK, an alternating-current voltage (AC Cont), and a switching signal L/R to the panel 700 based on the power supply voltage input from the power supply circuit 714 or various signals input from the CPU 712.

In the transmission-reception circuit 716, a signal that is transmitted and received as an electric wave by an antenna 743 is processed. Specifically, a high frequency circuit such as an isolator, a band path filter, a VCO (Voltage Controlled Oscillator), an LPF (Low Pass Filter), a coupler, or a balan is included. Among the signals transmitted and received by the transmission-reception circuit 716, signals including audio data are transmitted to the audio processing circuit 715 in accordance with an instruction transmitted from the CPU 712.

The signal including the audio data transmitted in accordance with the instruction by the CPU 712 is demodulated into an audio signal in the audio processing circuit 715 and transmitted to a speaker 748. Further, the audio signal transmitted from a microphone 747 is modulated in the audio processing circuit 715 and transmitted to the transmission-reception circuit 716 in accordance with the instruction from the CPU 712.

The controller 711, the CPU 712, the power supply circuit 714, the audio processing circuit 715, and the memory 713 can be mounted as a package of the printed wiring board 710. This embodiment mode can be applied to any circuit other than a high frequency circuit such as an isolator, a band path filter, a VCO (Voltage Controlled Oscillator), an LPF (Low Pass Filter), a coupler, or a balan.

As described above, by including a light emitting element containing a pyrazine derivative of the present invention as a light emitting element for forming a panel, a module emitting light efficiently can be obtained.

Embodiment Mode 7

In this embodiment mode, an example in which a module including a display device of the present invention as shown in Embodiment Mode 5 and Embodiment Mode 6 is mounted on a portable small-sized telephone set (cellular phone) operating wirelessly will be explained with reference to FIGS. 7A and 7B and FIG. 8.

A display panel 800 is detachably incorporated in a housing 801 so as to be easily fixed to a printed wiring board 810. The housing 801 can be appropriately changed in shape and size in accordance with an electronic device into which the housing 801 is incorporated.

Figure 8:
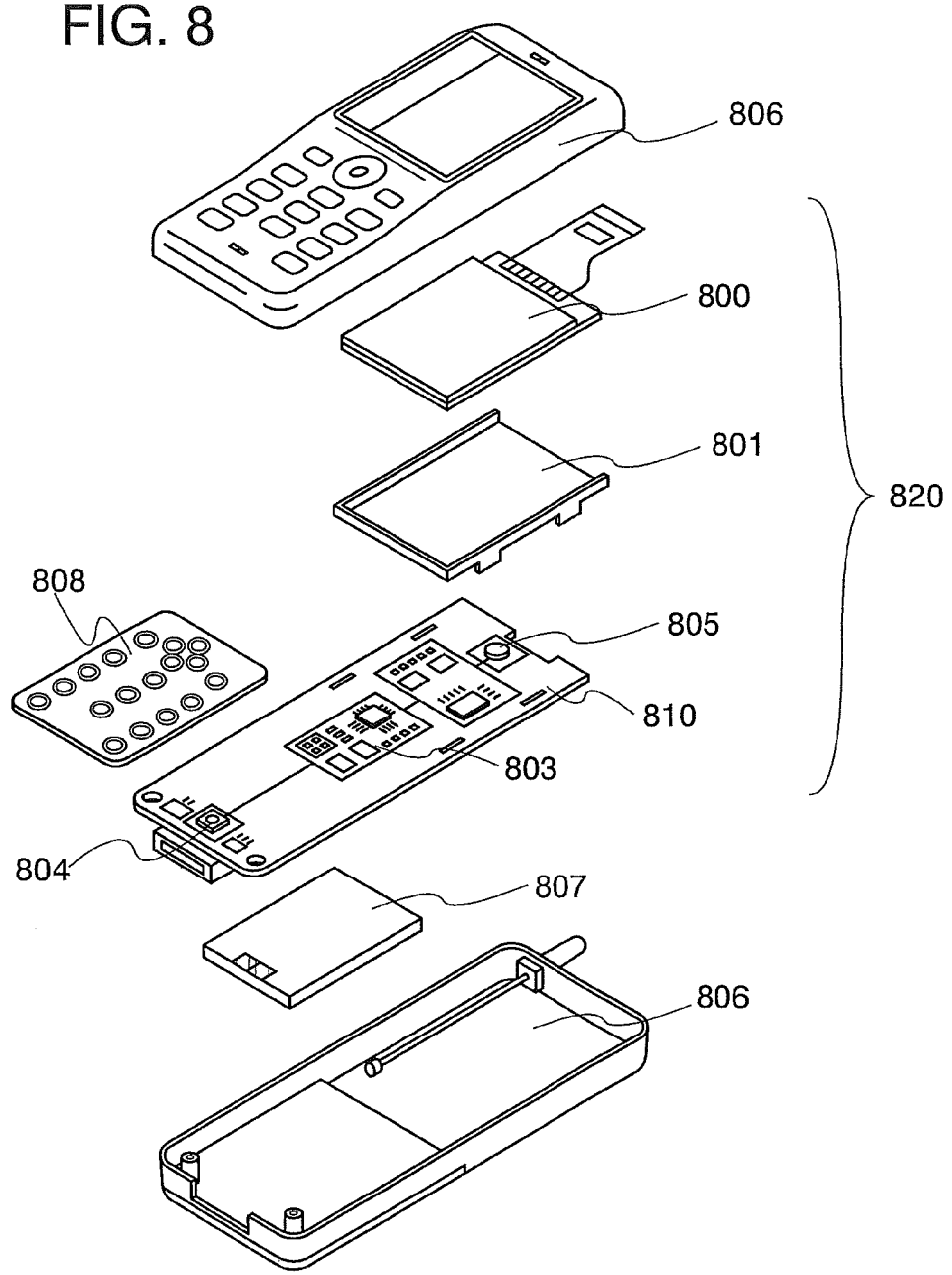
FIG. 8 is a view showing an example of an electronic device of the present invention.

In FIG. 8, the housing 801 to which the display panel 800 (corresponding to the panel 700 in FIGS. 7A and 7B) is fixed is fitted to the printed wiring board 810 (corresponding to the printed wiring board 710 in FIGS. 7A and 7B) and set up as a module. On the printed wiring board 810, a controller, a CPU, a memory, a power supply circuit, and other elements such as a resistor, a buffer, and a capacitor element are mounted. Moreover, an audio processing circuit including a microphone 804 and a speaker 805 and a signal processing circuit 803 such as a transmission-reception circuit are provided. The display panel 800 is connected to the printed wiring board 810 through an FPC as explained in FIGS. 7A and 7B.

Such a module 820, an input unit 808, and a battery 807 are stored in a chassis 806. A pixel portion of the display panel 800 is arranged so that it can be seen through a window formed in the chassis 806.

The chassis 806 shown in FIG. 8 shows an exterior shape of a telephone set as an example. However, the present invention is not limited thereto, and has various modes in accordance with functions and applications.

As described above, by including a light emitting element containing a pyrazine derivative of the present invention as a light emitting element for forming a display panel, a module of a small-sized telephone set (cellular phone) of which a display portion emits light efficiently or the like can be obtained.

Embodiment Mode 8

In this embodiment mode, various electronic devices will be explained. For example, electronic devices will be explained, such as a camera such as a video camera and a digital camera, a goggle type display (a head mounted display), a navigation system, an audio reproducing device (such as a car audio or an audio component), a personal computer, a game machine, a portable information terminal (such as a mobile computer, a cellular phone, a portable game machine, or an electronic book), and an image reproducing device provided with a recording medium (specifically, a device that reproduces a recording medium such as a Digital Versatile Disc (DVD) and has a display capable of displaying the reproduced image).

Figure 9A:
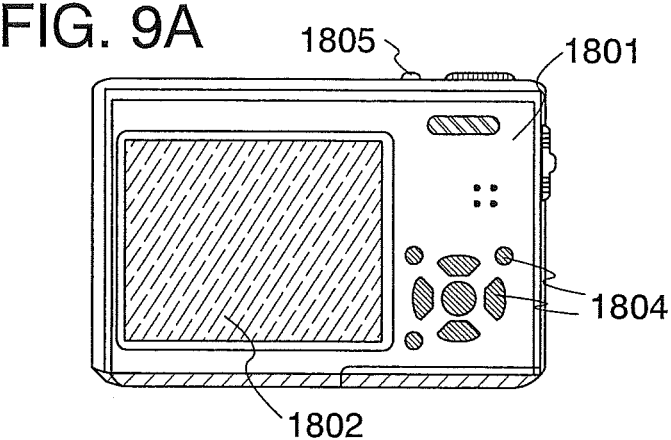
FIGS. 9A to 9D are views each showing an example of an electronic device of the present invention.

FIG. 9A shows a digital video camera, which includes a main body 1801, a display device 1802, an imaging portion, operating keys 1804, a shutter 1805, and the like. It is to be noted that FIG. 9A is a view of the display portion 1802 side, and the imaging portion is not shown. The display portion 1802 includes a light emitting element containing a pyrazine derivative of the present invention, whereby a favorable display can be performed.

Figure 9B:
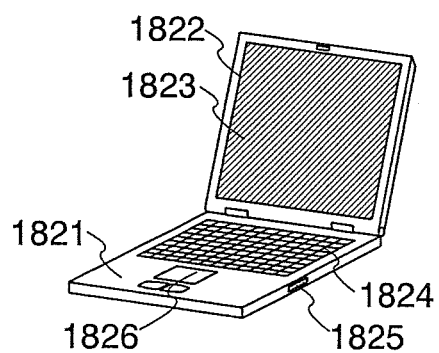

FIG. 9B shows a laptop personal computer, which includes a main body 1821, a chassis 1822, a display portion 1823, a keyboard 1824, an external connecting port 1825, a pointing mouse 1826, and the like. The display device 1823 includes a light emitting element containing a pyrazine derivative of the present invention, whereby a favorable display can be performed.

Figure 9C:
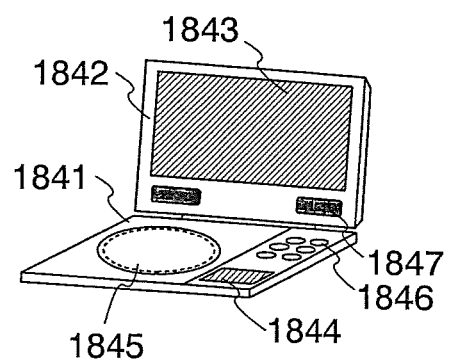

FIG. 9C shows a portable image reproducing device provided with a recording medium (specifically, a DVD reproducing device), which includes a main body 1841, a chassis 1842, a display portion A 1843, a display portion B 1844, a recording medium (DVD or the like) reading portion 1845, operating keys 1846, a speaker portion 1847, and the like. The display portion A 1843 mainly displays image information, and the display portion B 1844 mainly displays character information. It is to be noted that the image reproducing device provided with a recording medium includes a home game machine and the like. The display portion A 1843 and the display portion B 1844 includes a light emitting element containing a pyrazine derivative of the present invention, whereby favorable display can be performed.

Figure 9D:
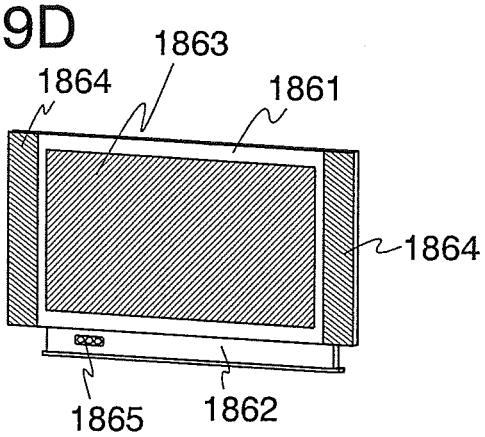

FIG. 9D shows a display device, which includes a chassis 1861, a supporting base 1862, a display portion 1863, a speaker 1864, a video input terminal 1865, and the like. It is to be noted that the display device includes all information display devices such as those for a computer, a television reception, an advertisement display, and the like. The display portion 1863 includes a light emitting element containing a pyrazine derivative of the present invention, whereby favorable display can be performed.

As described above, by including a light emitting element containing a pyrazine derivative of the present invention in a display portion or the like of various electronic devices, favorable display can be obtained.

Embodiment 1

Synthesis Example 1

As one example of a pyrazine derivative of the present invention, a synthesis method of a compound represented by a structural formula (s-9), that is, 2,3-bis{4-[N,N-di(biphenyl-4-yl)amino]phenyl}pyrazine (hereinafter, referred to as BBAPPr) will be explained.

Step 1: Synthesis method of 2,3-bis(4-bromophenyl)pyrazine (hereinafter, refereed to as PPr)

(1) Synthesis of 2,3-bis(4-bromophenyl)-5,6-dihydropyrazine 10 g (27 mmol) of 4,4'-dibromobenzyl was put into a 300 mL three neck flask, and 200 mL of chloroform was added thereto to be dissolved. Then, 3.0 mL (45 mmol) of etylendiamine was added thereto, and this mixture was heated and stirred for 5 hours at 80° C. to be reacted. After the reaction, the reaction solution was washed with water, and a solvent was removed to obtain 10 g of a light yellow solid of 2,3-bis(4-bromophenyl)-5,6-dihydropyrazine in the yield of 94% (Synthesis Scheme (e-1)).

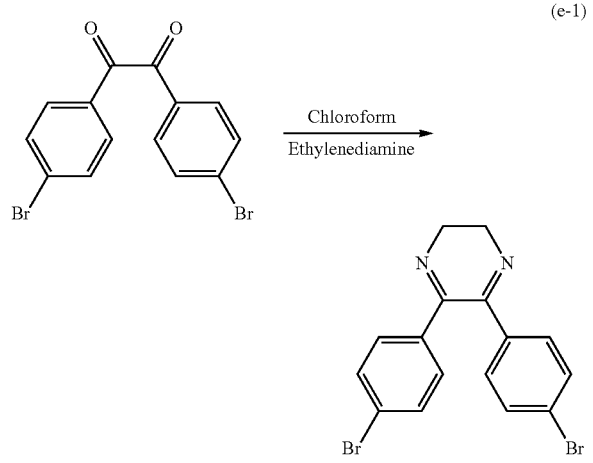

(2) Synthesis of PPr 10 g (27 mmol) of 2,3-bis(4-bromophenyl)-5,6-dihydropyrazine was put into a 500 mL three neck flask, and 100 mL of ethanol was added to be dissolved. Then, 8.8 g (54 mmol) of iron(III) chloride was added thereto, and this mixture was heated and stirred for 30 minutes at 60° C. to be reacted. After the reaction, 300 mL of water was added to the reaction mixture, a precipitated solid was dissolved in toluene. After this mixture was washed with saturated saline, the solid that was obtained by concentrating the solvent was purified by silica column chromatography. The purification by the silica column chromatography (hereinafter, also referred to as column purification) was performed as follows: first, toluene was used as a developing solvent; and a mixed solvent of toluene:ethyl acetate=1:1 was used as a developing solvent. After the column purification, the solvent of the obtained solution was concentrated to obtain 6.3 g of an orange solid of PPr in the yield of 60% (Synthesis Scheme (e-2)).

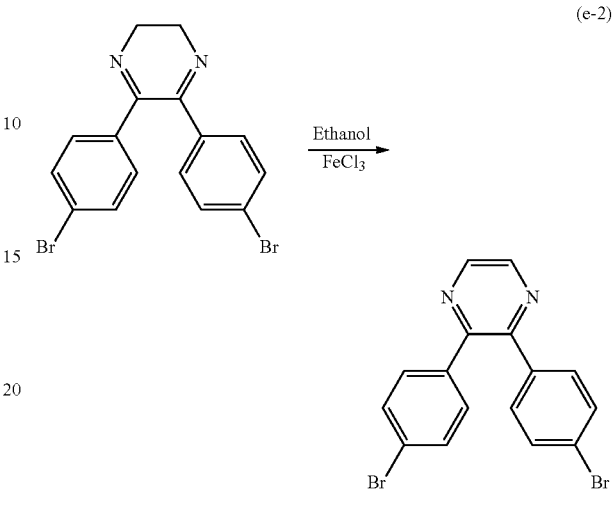

Step 2: Synthesis method of di(biphenyl-4-yl)amine (hereinafter, referred to as BBA)

(1) Synthesis of 4,4'-dibromodiphenylamine 50 g (169 mmol) of diphenylamine and 1000 mL of ethyl acetate were put into a 2000 mL three neck flask, and 108 g (605 mmol) of N-bromosuccinimide was added. This mixture was stirred for approximately 12 hours at the room temperature to be reacted. After the reaction, the reaction solution was washed with water. An aqueous layer was extracted from the solution by ethyl acetate to be separated from an organic layer, and the organic layer was dried with magnesium sulfate and filtered. After the filtration, the filtrate was concentrated, and the obtained solid was washed with hexane, whereby 73 g of a white solid of 4,4'-dibromophenylamine was obtained in the yield of 76% (Synthesis Scheme (e-3)).

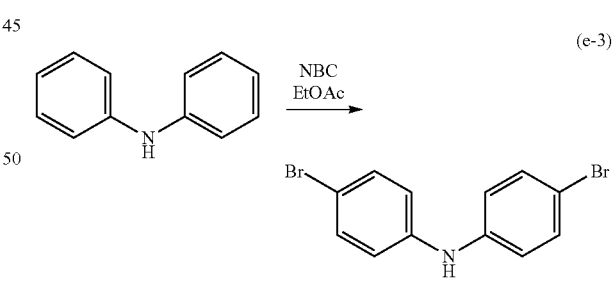

(2) Synthesis of BBA 30 g (92 mmol) of 4,4'-dibromodiphenylamine, 25 g of (204 mmol) of phenylboronic acid, 0.46 g (2.0 mmol) of palladium acetate, and 1.4 g (4.5 mmol) of tris(o-tolyl)phosphine were put into a 500 mL three neck flask, and nitrogen was substituted for the content of the flask. Then, 300 mL of ethylene glycol dimethylether and 300 mL (2.0 mol/L) of potassium carbonate solution were added thereto, and this mixture was stirred for 5 hours at 80° C. to be reacted. After the reaction, a precipitated object was filtered, and the filtered object was re-crystallized with chloroform and hexane, whereby 23 g of a white solid of BBA was obtained in the yield of 78% (Synthesis Scheme (e-4)).

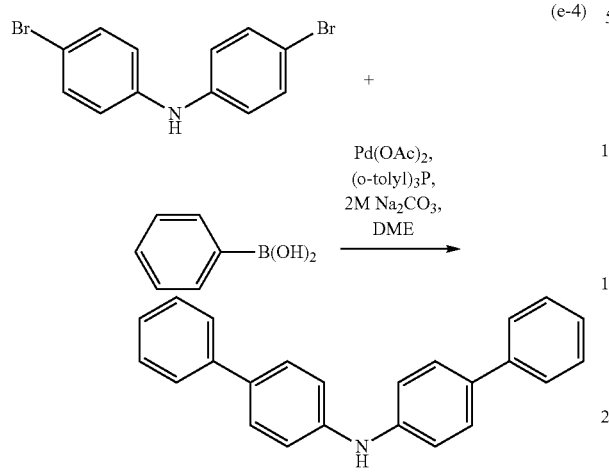

(e-4)

Step 3: Synthesis Method of BBAPPr 1.5 g of (3.9 mmol) of PPr, 2.5 g (7.7 mmol) of BBA, and 1.5 g (15.4 mmol) of sodium-tert-butoxide were put into a 200 mL three neck flask, and nitrogen was substituted for the content of the flask. Then, 20 mL of toluene, 1.0 mL of a hexane solution (10 wt %) of tri-tert-butylphosphine, and 0.1 g (0.2 mmol) of bis(dibenzylideneacetone)palladium(0) were added thereto, and this mixture was heated and stirred for 3 hours at 80° C. to be reacted. After the reaction, the reaction mixture was filtered through florisil, celite, and alumina. The filtrate was washed with water and dried with magnesium sulfate, and then filtration was performed. A solid that was obtained by concentrating the filtrate was dissolved in toluene to be purified by silica column chromatography. For the column purification, first, toluene was used as a developing solvent, and then a mixed solvent of toluene:ethyl acetate=9:1 was used as a developing solvent. After the column purification, the obtained solution was re-crystallized with chloroform and hexane, whereby 0.51 g of a yellow solid was obtained in the yield of 15%.

The obtained yellow solid was sublimated and purified by a train sublimation method. The sublimation and purification were performed for 12 hours at 280° C. under the condition of 7 Pa of reduced pressure and 3 mL/min of flow of argon. When the charged amount of the obtained yellow solid was 0.51 g, 0.28 g of a yellow solid of BBAPPr that is an object was obtained in the yield of 54% (Synthesis Scheme (e-5)).

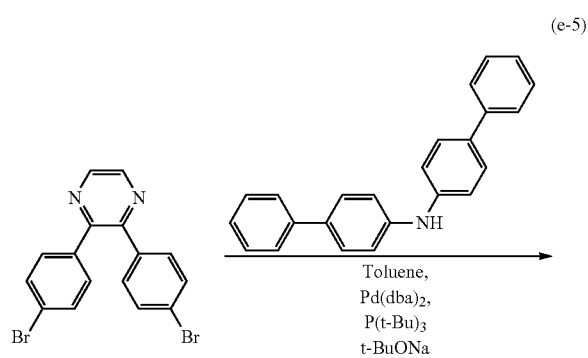

(e-5)

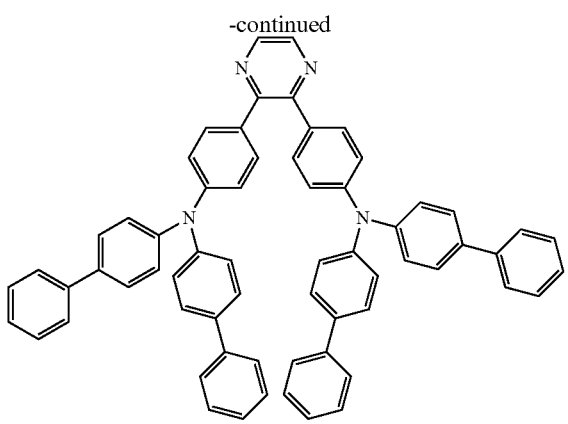

An analysis result by a proton nuclear magnetic resonance method ($^1$H-NMR) of BBAPPr is shown below. As a reference substance, tetramethylsilane (abbreviated to TMS) was used.

$^1$H-NMR (300 MHz, CDCl$_3$); δ=7.12-7.58 (m, 44H), δ=8.54 (s, 2H)

Figure 10A:
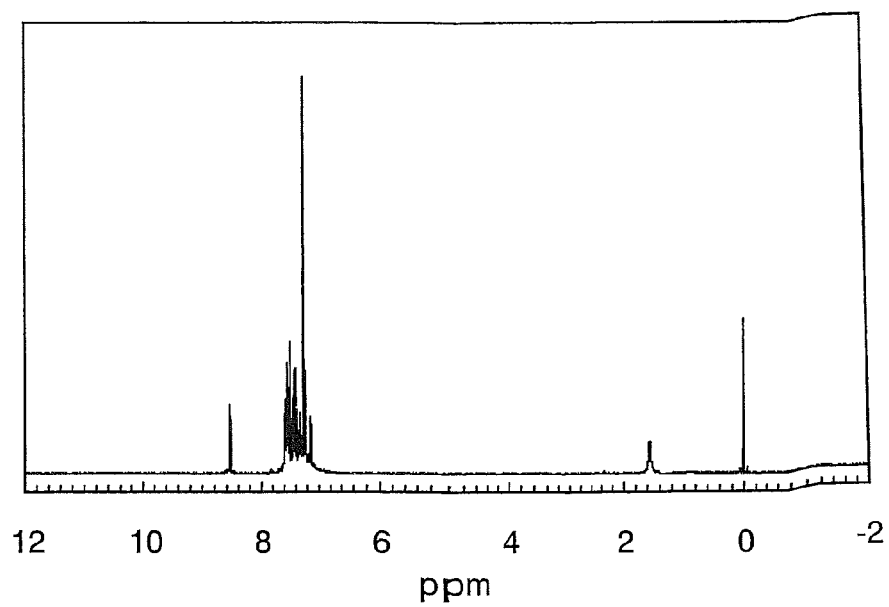
FIGS. 10A and 10B are $^1$H-NMR charts of BBAPPr.
Figure 10B:
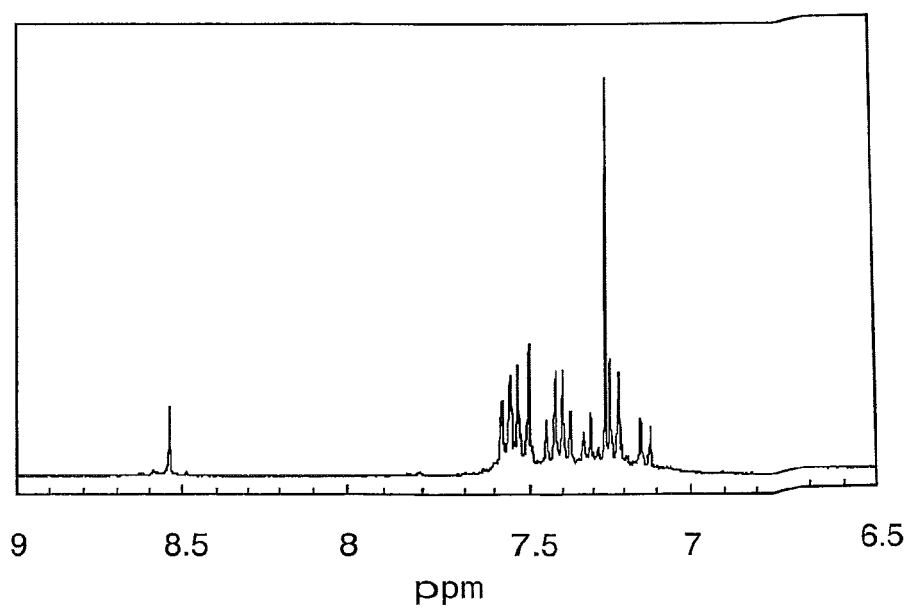

FIGS. 10A and 10B each show a $^1$H-NMR chart of BBAPPr. FIG. 10B is an enlarged chart of a range of 6.5 to 9.0 ppm of the chart of FIG. 10A.

Figure 11:
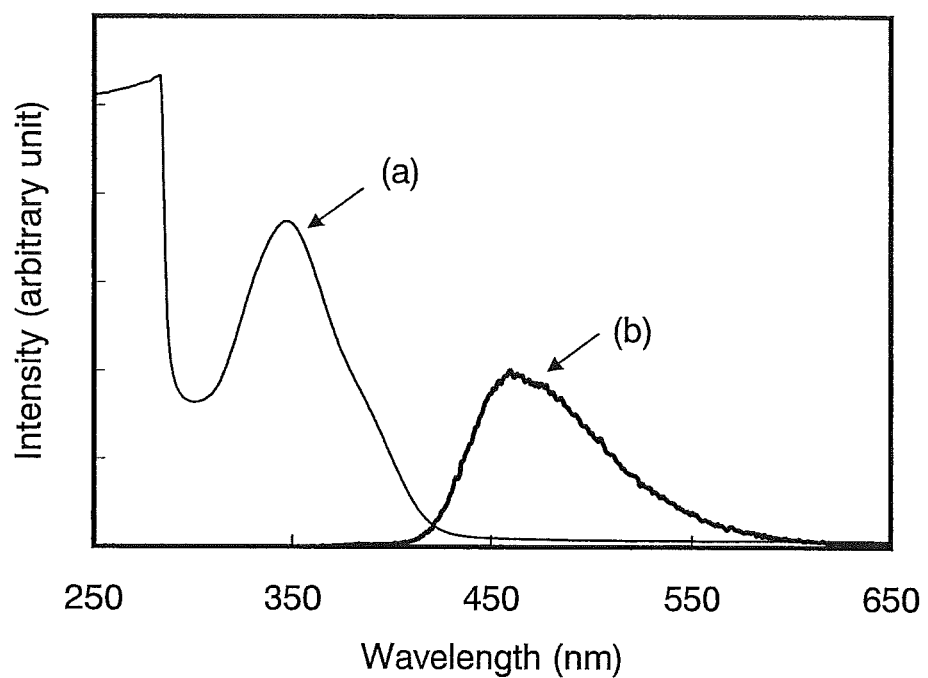
FIG. 11 is a graph showing an absorption spectrum and an emission spectrum in a state where BBAPPr is dissolved in a toluene solution.

FIG. 11 shows an absorption spectrum and an emission spectrum in a state where BBAPPr is dissolved in a toluene solution. The ultraviolet-visible spectrophotometer (V-550, manufactured by JASCO Corporation) was used for the measurement. In FIG. 11, the horizontal axis represents a wavelength (nm) and the vertical axis represents intensity (arbitrary unit). Further, in FIG. 11, a line (a) indicates the absorption spectrum whereas a line (b) indicates the emission spectrum (347 nm of an excited wavelength).

Figure 12A:
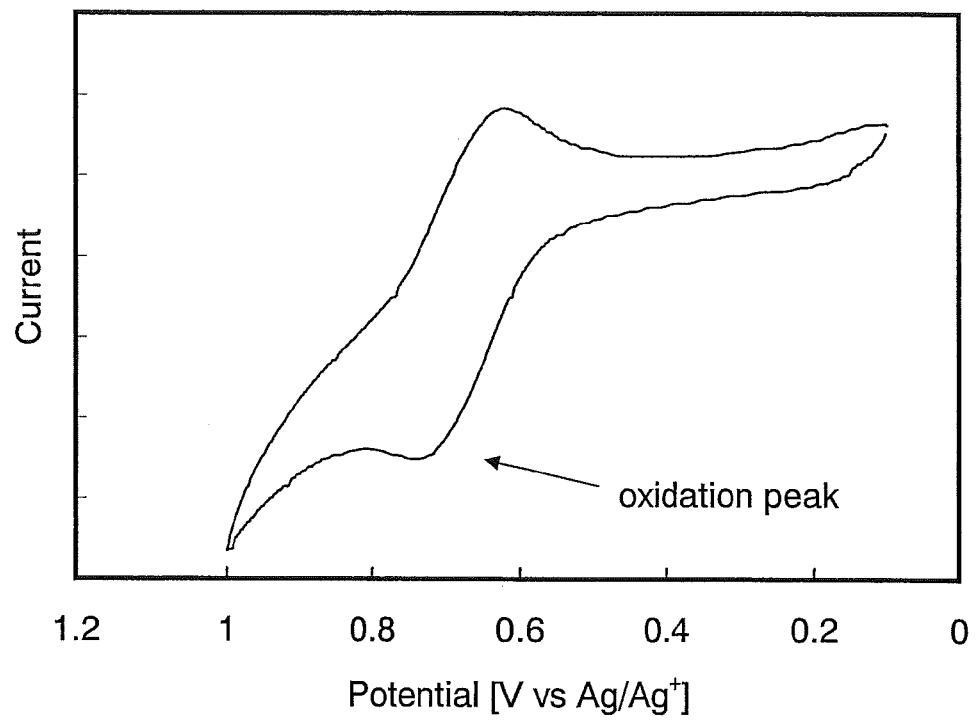
FIGS. 12A and 12B are graphs showing a measurement result by cyclic voltammetry (CV) of BBAPPr.
Figure 12B:
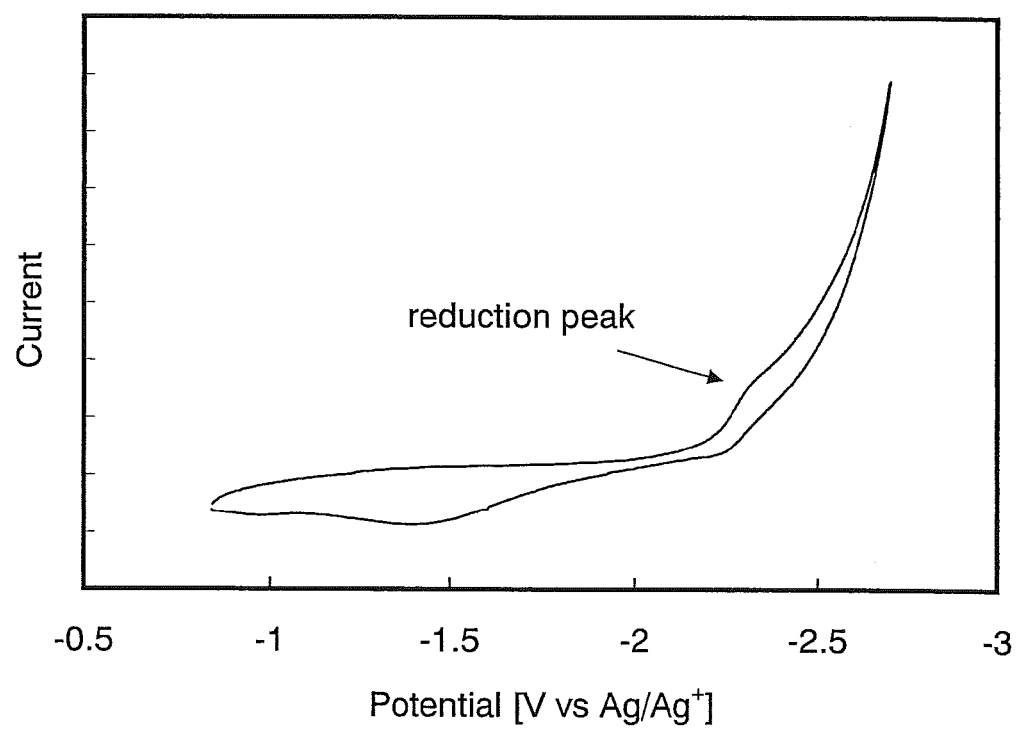

In addition, an oxidation-reduction reaction characteristic of BBAPPr was measured by cyclic voltammetry (CV) measurement. FIGS. 12A and 12B each show a result thereof. Further, an electrochemical analyzer (ALS model 600A, manufactured by BAS Inc.) was used for the measurement.

As for a solution used in the CV measurement, dehydrated dimethylformamide (abbreviated to DMF) was used as a solvent. Tetra-n-butylammonium perchlorate (n-Bu$_4$NClO$_4$), which was a supporting electrolyte, was dissolved in the solvent to have the concentration of 100 mmol/L. Moreover, BBAPPr that is a measuring object was dissolved to have the concentration of 1 mmol/L. Further, a platinum electrode (a PTE platinum electrode, manufactured by BAS Inc.) was used as a work electrode. A platinum electrode (a VC-3 Pt counter electrode (5 cm), manufactured by BAS Inc.) was used as an auxiliary electrode. An Ag/Ag$^+$ electrode (an RE5 nonaqueous solvent reference electrode, manufactured by BAS Inc.) was used as a reference electrode.

The oxidation reaction characteristic was measured as follows: potential of the work electrode with respect to the reference electrode was scanned from at 0.10 to 1.00 V; and potential of the work electrode was scanned from at 1.00 to 0.10 V. It is to be noted that the scanning speed of the CV measurement was set to be at 0.1 V/s.

The reduction reaction characteristic was measured as follows: potential of the work electrode with respect to the reference electrode was scanned from at −0.84 to −2.70 V; and potential of the work electrode was scanned from at −2.70 to −0.84 V. It is to be noted that the scanning speed of the CV measurement was set to be at 0.1 V/s.

A CV curved line for measuring the oxidation reaction characteristic of BBAPPr is shown in FIG. 12A. Moreover, a CV curved line for measuring the reduction reaction characteristic of BBAPPr is shown in FIG. 12B. In both FIGS. 12A and 12B, the horizontal axis indicates the potential of the work electrode with respect to the reference electrode, whereas the vertical axis indicates the current value flowing between the work electrode and the auxiliary electrode. As shown in FIGS. 12A and 12B, both a peak showing oxidization and a peak showing reduction in BBAPPr were definitely observed. In other words, it was found that BBAPPr is a substance in which holes and electrons easily enter. From this, it was found that BBAPPr is a substance having a bipolar property.

Embodiment 2

Synthesis Example 2

As one example of a pyrazine derivative of the present invention, a synthesis method of a compound represented by a structural formula (s-16), that is, 2,3-bis{4-[N-(biphenyl-4-yl)-N-phenylamino]phenyl}pyrazine (hereinafter, referred to as BPhAPPr), will be explained.

Step 1: Synthesis Method of 4-phenyldiphenylamine (Hereinafter, Referred to as BPhA)

40 g (172 mmol) of 4-bromobiphenyl, 19 g (206 mmol) of aniline, 0.99 g (1.7 mmol) of bis(dibenzylideneacetone)palladium(0), 41 g (429 mmol) sodium-tert-butoxide were put into a 500 mL three neck flask, and nitrogen was substituted for the content of the flask. Then, 300 mL of toluene and 5.9 g (2.9 mmol) of a hexane solution (10 wt %) of tri-tert-butylphosphine were added thereto, and this mixture was stirred for 2 hours at 80° C. to be reacted. After the reaction, the reaction mixture was washed with water. Then, an aqueous layer was extracted from the mixture by toluene to be separated from an organic layer, and the organic layer was dried with magnesium sulfate and filtered. Then, a solid that was obtained by concentrating the filtrate was purified by silica column chromatography, whereby 33 g of a white solid of BPhA that is an object was obtained in the yield 80% (Synthesis Scheme (f-1)). The column purification was performed using toluene as a developing solution.

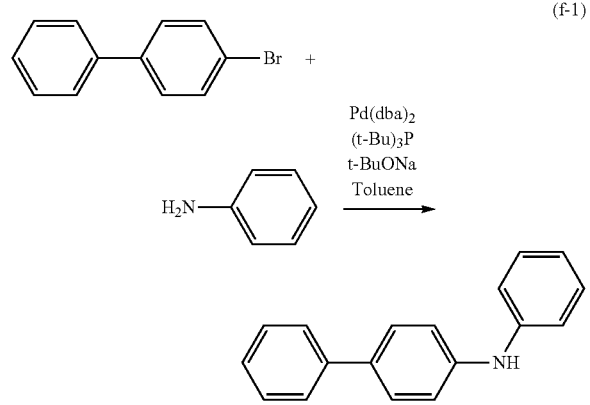

(f-1)

Step 2: Synthesis Method of BPhAPPr 0.74 g (1.9 mmol) of PPr, 0.93 g (3.9 mmol) of BPhA, and 0.8 g of sodium-tert-butoxide were put into a 200 mL three neck flask, and nitrogen was substituted for the content of the flask. Then, 70 mL of toluene, 1.5 mL of a hexane solution (10 wt %) of tri-tert-butylphosphine, and 0.2 g (0.4 mmol) of bis(dibenzylideneacetone)palladium(0) were added thereto, and this mixture was stirred for 3 hours at 80° C. to be reacted. After the reaction, the reaction mixture was filtered through florisil, celite, and alumina. The filtrate was washed with water and dried with magnesium sulfate, and then filtration was performed. A solid that was obtained by concentrating the filtrate was re-crystallized with dichloromethane and hexane, whereby 1.0 g of a yellow solid was obtained in the yield of 70%.

The obtained yellow solid was sublimated and purified by a train sublimation method. The sublimation and purification were performed for 12 hours at 300° C. under the condition of 7 Pa of reduced pressure and 3 mL/min of flow of argon. When the charged amount of the obtained yellow solid was 1.0 g, 0.90 g of a yellow solid of BPhAPPr that is an object was obtained in the yield of 90% (Synthesis Scheme (f-2)).

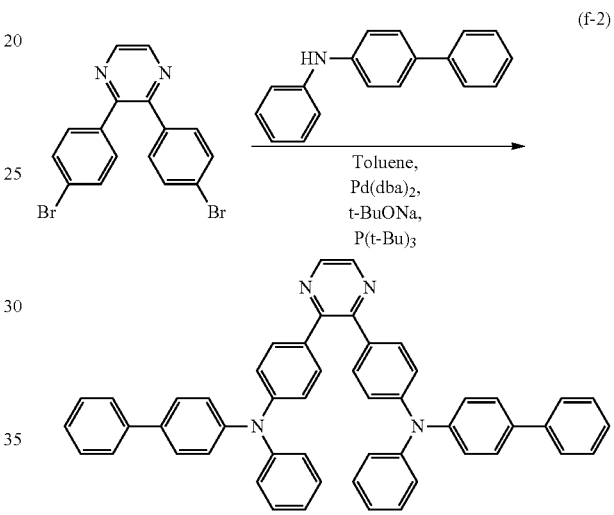

(f-2)

An analysis result by a proton nuclear magnetic resonance method ($^1$H-NMR) of BPhAPPr is shown below. As a reference substance, tetramethylsilane (abbreviated to TMS) was used.

$^1$H-NMR (300 MHz, CDCl$_3$); δ=7.06-7.44 (m, 28H), δ=7.49 (d, J=9.0, 4H), δ=7.56 (d, J=7.2, 4H), δ=8.52 (s, 2H)

Figure 13A:
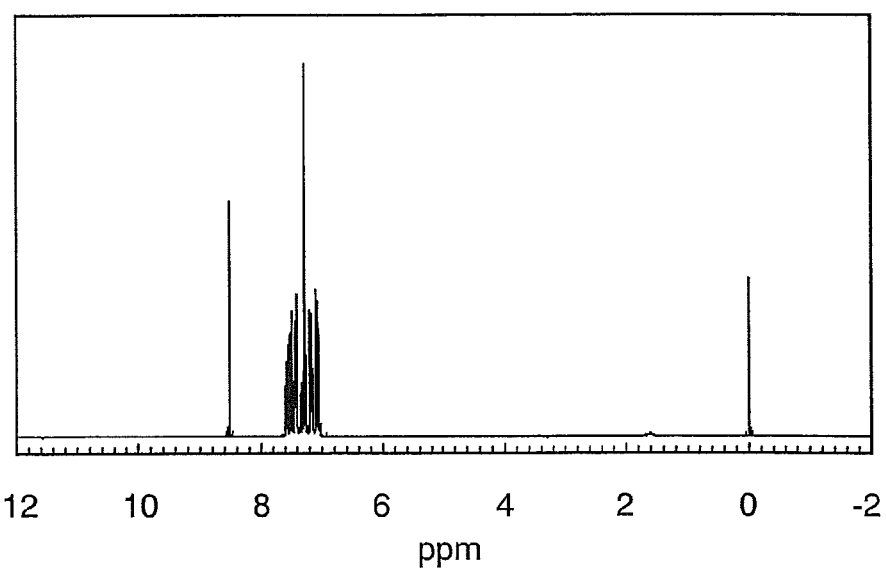
FIGS. 13A and 13B are $^1$H-NMR charts of BBhAPPr.
Figure 13B:
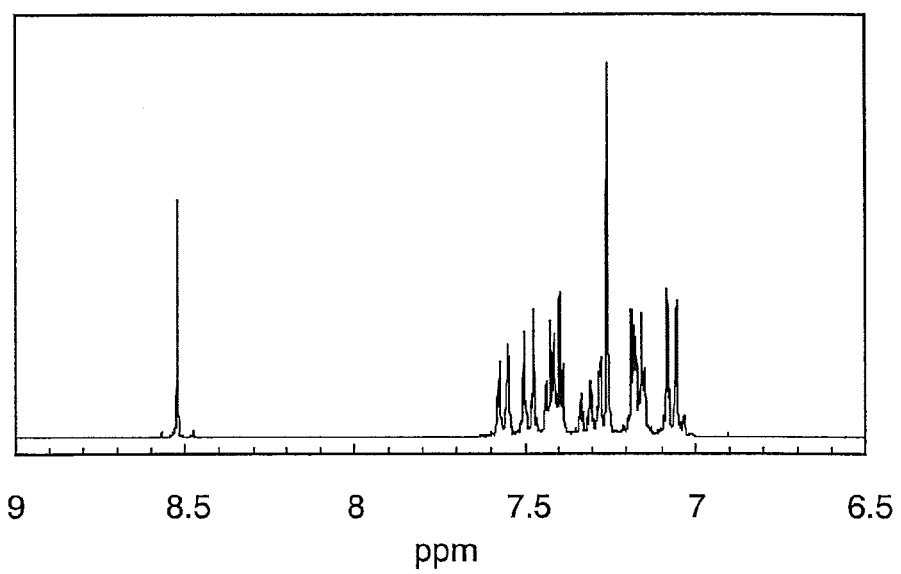

FIGS. 13A and 13B each show a $^1$H-NMR chart of BPhAPPr. FIG. 13B is an enlarged chart of a range of 6.5 to 9.0 ppm of the chart of FIG. 13A.

Figure 14:
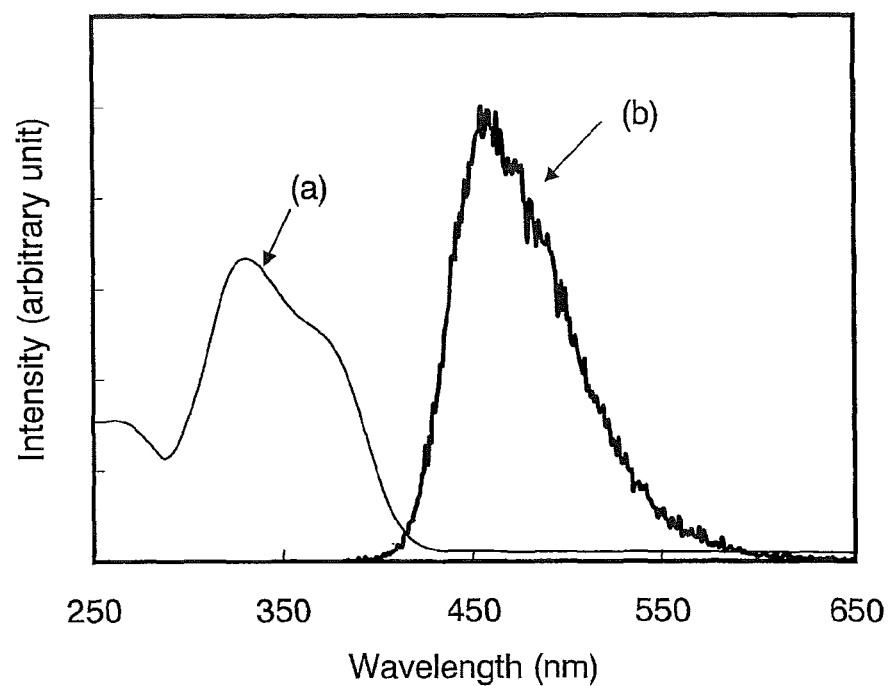
FIG. 14 is a graph showing an absorption spectrum and an emission spectrum in a state where BBhAPPr is dissolved in a toluene solution.

FIG. 14 shows an absorption spectrum and an emission spectrum in a state where BPhAPPr is dissolved in a toluene solution. The ultraviolet-visible spectrophotometer (V-550, manufactured by JASCO Corporation) was used for the measurement. In FIG. 14, the horizontal axis represents a wavelength (nm) and the vertical axis represents intensity (arbitrary unit). Further, in FIG. 14, a line (a) indicates the absorption spectrum whereas a line (b) indicates the emission spectrum (352 nm of an excited wavelength).

Figure 15:
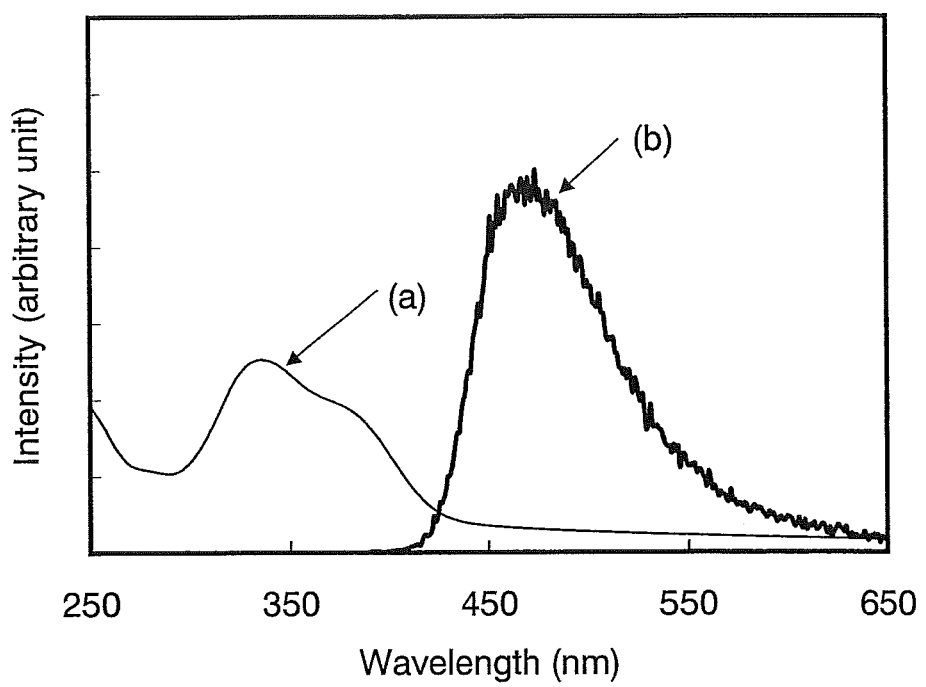
FIG. 15 is a graph showing an absorption spectrum and an emission spectrum in a single film state of BPhAPPr.

FIG. 15 shows an absorption spectrum and an emission spectrum in a single film state of BPhAPPr. The ultraviolet-visible spectrophotometer (V-550, manufactured by JASCO Corporation) was used for the measurement. In FIG. 15, the horizontal axis represents a wavelength (nm) and the vertical axis represents intensity (arbitrary unit). Further, in FIG. 15, a line (a) indicates the absorption spectrum whereas a line (b) indicates the emission spectrum (336 nm of an excited wavelength).

Embodiment 3

Synthesis Example 3

As one example of a pyrazine derivative of the present invention, a synthesis method of a compound represented by a structural formula (s-13), that is, 2,3-bis[4-(N,N-diphenylamino)phenyl]pyrazine (hereinafter, referred to as DPhAPPr), will be explained.

Step 1: Synthesis Method of DPhAPPr 3.0 g (7.7 mmol) of PPr, 2.6 g (15.4 mmol) of diphenylamine (manufactured by Tokyo Chemical Industry Co., Ltd) (hereinafter, referred to as DPhA), and 3.0 g (30.8 mmol) of sodium-tert-butoxide were put into a 200 mL three neck flask, and nitrogen was substituted for the content of the flask. Then, 40 mL of toluene, 0.3 mL of a hexane solution (10 wt %) of tri-tert-butylphosphine, and 0.3 g (0.6 mmol) of bis(dibenzylideneacetone)palladium(0) were added thereto, and this mixture was stirred for 5 hours at 80° C. to be reacted. After the reaction, the reaction mixture was filtered through florisil, celite, and alumina. The filtrate was washed with water and dried with magnesium sulfate, and then filtration was performed. A solid that is obtained by concentrating the filtrate was dissolved in toluene to be purified by silica column chromatography. For the column purification, first, toluene was used as a developing solution, and then a mixed solvent of toluene:ethyl acetate=9:1 was used as a developing solvent. After the column purification, the obtained solution was re-crystallized with chloroform and hexane, whereby 3.5 g of a yellow solid was obtained in the yield of 80%.

The obtained yellow solid was sublimated and purified by a train sublimation method. The sublimation and purification were performed for 12 hours at 240° C. under the condition of 7 Pa of reduced pressure and 3 mL/min of flow of argon. When the charged amount of the yellow solid was 3.5 g, 3.0 g of a yellow solid of DPhAPPr that is an object was obtained in the yield of 86% (Synthesis Scheme (h-1)).

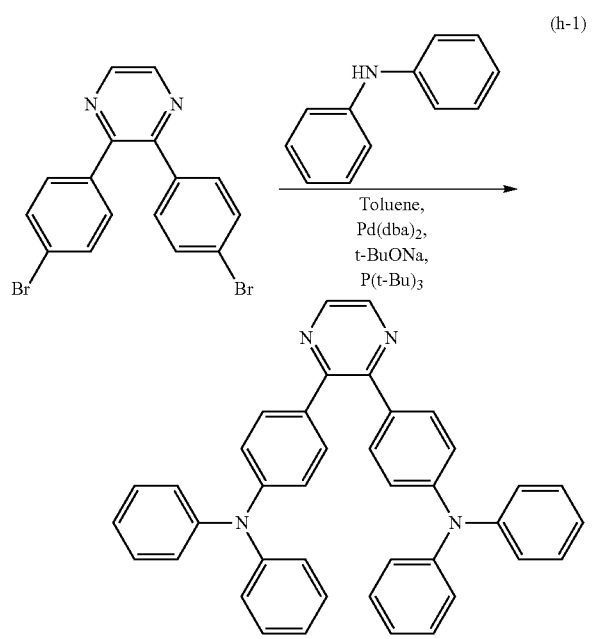

An analysis result by a proton nuclear magnetic resonance method ($^1$H-NMR) of DPhAPPr is shown below. As a reference substance, tetramethylsilane (abbreviated to TMS) was used.

$^1$H-NMR (300 MHz, CDCl$_3$); δ=6.98-7.14 (m, 16H), δ=7.23-7.30 (m, 8H), δ=7.37 (d, J=9.0, 4H), δ=8.50 (s, 2H)

Figure 16A:
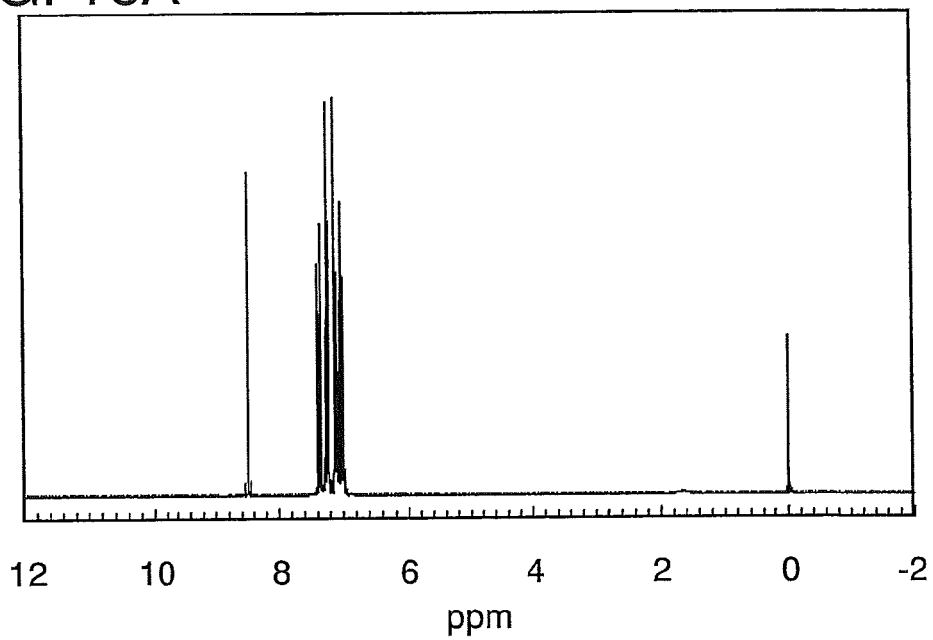
FIGS. 16A and 16B are $^1$H-NMR charts of DPhAPPr.
Figure 16B:
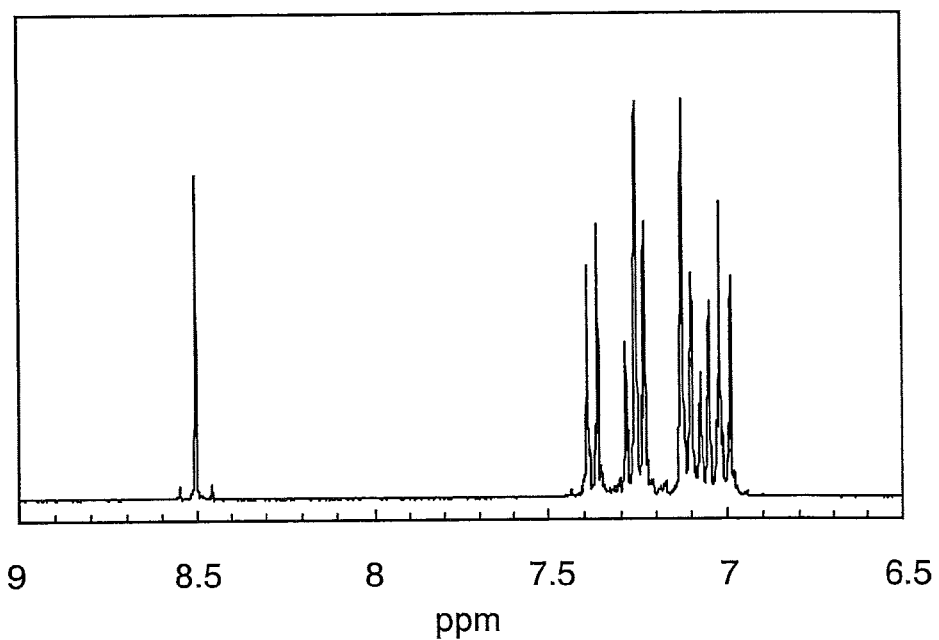

FIGS. 16A and 16B each show a $^1$H-NMR chart of DPhAPPr. FIG. 16B is an enlarged chart of a range of 6.5 to 9.0 ppm of the chart of FIG. 16A.

Figure 17:
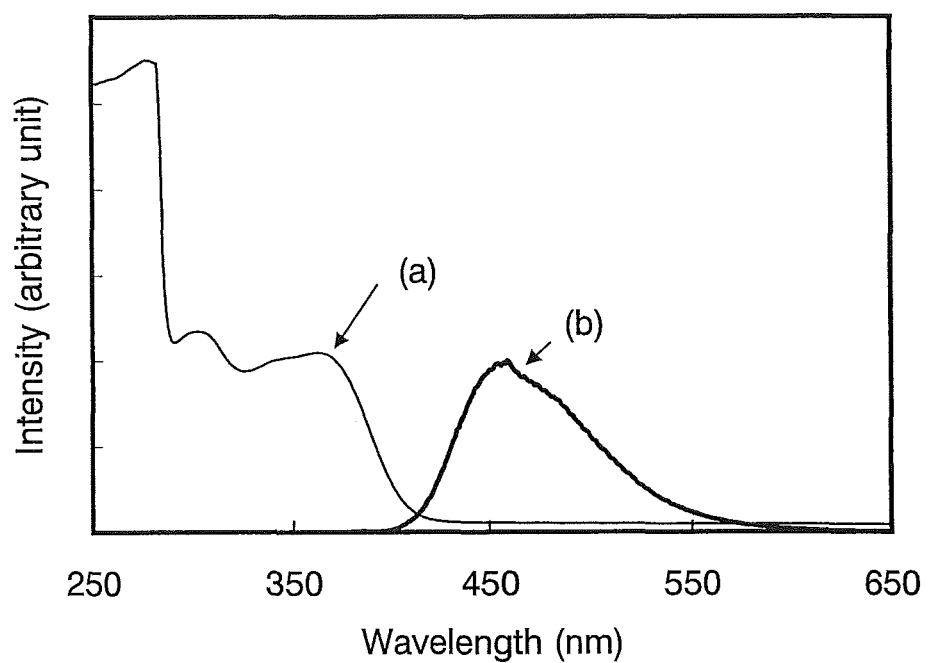
FIG. 17 is a graph showing an absorption spectrum and an emission spectrum in a state where DPhAPPr is dissolved in a toluene solution.

FIG. 17 shows an absorption spectrum and an emission spectrum in a state where DPhAPPr is dissolved in a toluene solution. The ultraviolet-visible spectrophotometer (V-550, manufactured by JASCO Corporation) was used for the measurement. In FIG. 17, the horizontal axis represents a wavelength (nm) and the vertical axis represents intensity (arbitrary unit). Further, in FIG. 17, a line (a) indicates the absorption spectrum whereas a line (b) indicates the emission spectrum (364 nm of an excited wavelength).

Figure 18:
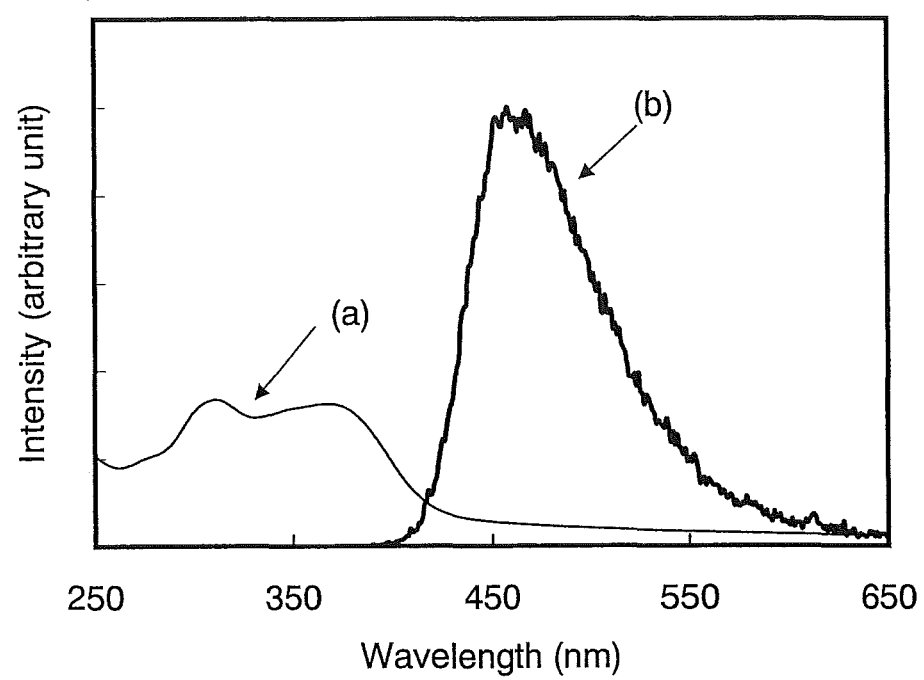
FIG. 18 is a graph showing an absorption spectrum and an emission spectrum in a single film state of DPhAPPR.

FIG. 18 shows an absorption spectrum and an emission spectrum in a single film state of DPhAPPr. In FIG. 18, the horizontal axis represents a wavelength (nm) and the vertical axis represents intensity (arbitrary unit). Further, in FIG. 18, a line (a) indicates the absorption spectrum whereas a line (b) indicates the emission spectrum (368 nm of an excited wavelength).

Embodiment 4

Synthesis Example 4

As one example of a pyrazine derivative of the present invention, a synthesis method of a compound represented by a structural formula (s-53), that is, 2,3-bis{4-[N-(4-diphenylaminophenyl)-N-phenylamino]phenyl}pyrazine (hereinafter, referred to as DPAPPr), will be explained.

Step 1: Synthesis method of N,N,N'-triphenyl-1,4-phenylenediamine (hereinafter, referred to as DPA)

(1) Synthesis of 4-bromotriphenylamine 25 g (100 mmol) of triphenylamine, 18 g (100 mmol) of N-bromosuccinimide, and 400 mL of ethyl acetate were put into a 1000 mL Erlenmeyer flask, and were stirred for approximately 12 hours at the room temperature in the air to be reacted. After the reaction was completed, the reaction solution was washed twice with a saturated sodium carbonate solution to separate an aqueous layer and an organic layer. Then, the aqueous layer was extracted twice with ethyl acetate, and the extract was combined with the organic layer, and washed with a saturated saline solution. The solution was dried with magnesium sulfate, and then filtration was performed. The filtrate was concentrated, and an obtained solid of 4-bromotriphenylamine was re-crystallized with ethyl acetate and hexane, whereby 22 g of a white powder solid was obtained in the yield of 66% (Synthesis Scheme (i-1)).

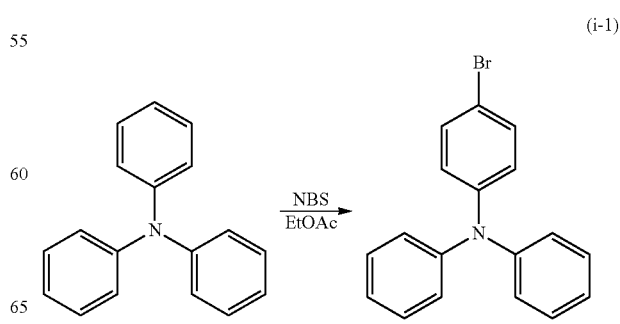

(2) Synthesis of DPA 0.56 g (6 mmol) of 4-bromotriphenylamine, 0.35 g (0.6 mmol) of bis(dibenzylideneacetone)palladium(0), and 0.58 g (6 mmol) of sodium-tert-butoxide were put into a 100 mL three neck flask, and 5 mL of toluene was added thereto. After nitrogen was substituted for the content of the flask, 0.56 g (6 mmol) of aniline and 0.37 mL (1.8 mmol) of a hexane solution (10 wt %) of tri-tert-butylphosphine were added. This mixture was stirred for 5 hours at 80° C. to be reacted. After the reaction, the reaction was completed by adding a saturated saline solution to the reaction mixture, and an aqueous layer was extracted by approximately 100 mL of ethyl acetate to be separated from an organic layer. The organic layer was dried with magnesium sulfate and filtered. A solid that was obtained by concentrating the filtrate was purified by silica column chromatography, whereby 0.24 g of a light yellow powder solid of DPA that is an object was obtained in the yield of 42% (Synthesis Scheme (i-2)). For the column purification, a mixed solvent of ethyl acetate:hexane=1:20 was used as a developing solvent.

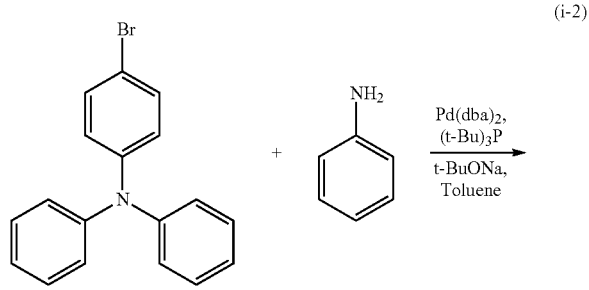

(i-2)

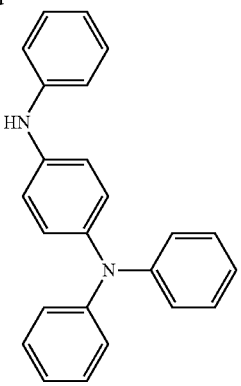

Step 2: Synthesis Method of DPAPPr 0.52 g (1.3 mmol) of PPr, 0.90 g (2.7 mmol) of DPA, and 0.8 g (8.3 mmol) of sodium-tert-butoxide were put into a 100 mL three neck flask, and nitrogen was substituted for the content of the flask. Then, 15 mL of toluene and 0.1 mL of a hexane solution (10 wt %) of tri-tert-butylphosphine were added, and nitrogen was substituted for the content of the flask again. Moreover, 0.1 g (0.2 mmol) of bis(dibenzylideneacetone)palladium(0) was added thereto, and this mixture was stirred for 5 hours at 120° C. to be reacted. After the reaction, the reaction mixture was filtered through celite. The filtrate was washed with water and dried with magnesium sulfate, and then filtration was performed. A solid that is obtained by concentrating the filtrate was dissolved in toluene to be purified by silica column chromatography. For the column purification, first, toluene was used as a developing solvent, and then a mixed solvent of toluene:ethyl acetate=9:1 was used as a developing solvent. After the column purification, the obtained solution was re-crystallized with chloroform and hexane, whereby 0.27 g of a yellow solid of DPAPPr was obtained in the yield of 80% (Synthesis Scheme (i-3)).

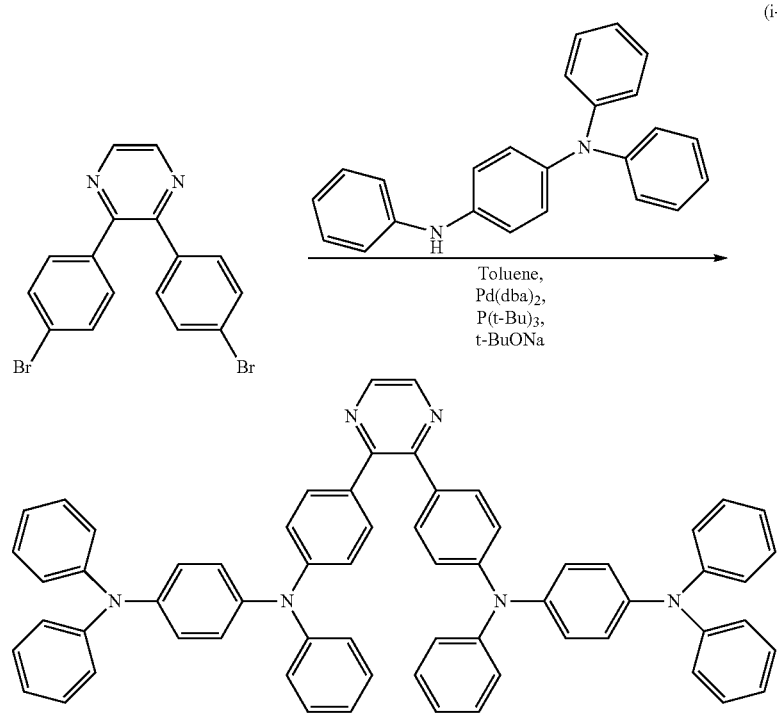

(i-3)

An analysis result by a proton nuclear magnetic resonance method (¹H-NMR) of DPAPPr is shown below. As a reference substance, tetramethylsilane (abbreviated to TMS) was used.

¹H-NMR (300 MHz, CDCl₃); δ=6.99-7.26 (m, 42H), δ=7.37 (d, J=8.4, 4H), δ=8.49 (s, 2H)

Figure 19A:
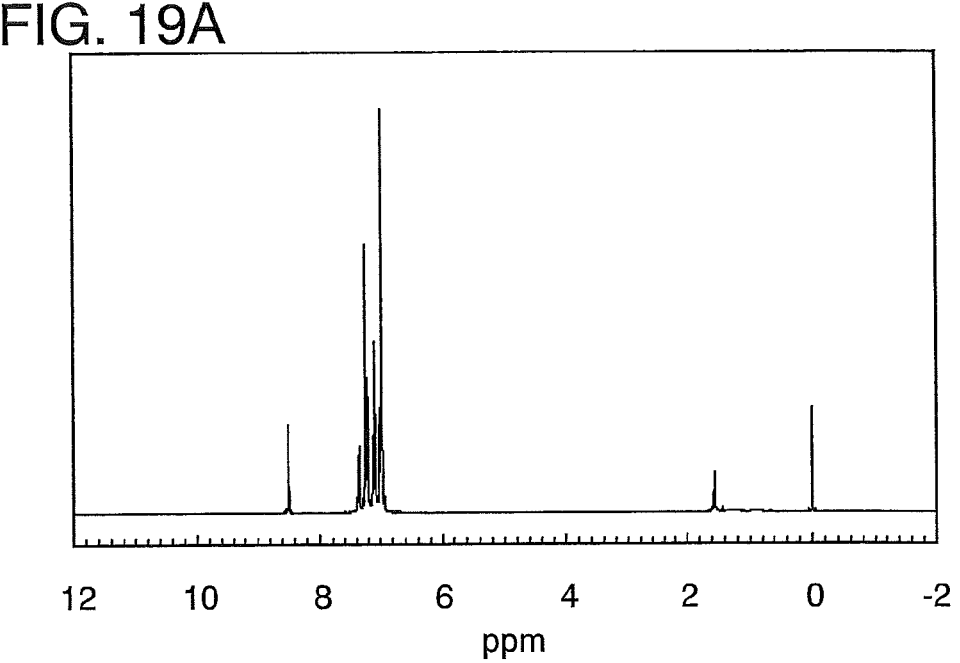
FIGS. 19A and 19B are $^1$H-NMR charts of DPAPPr.
Figure 19B:
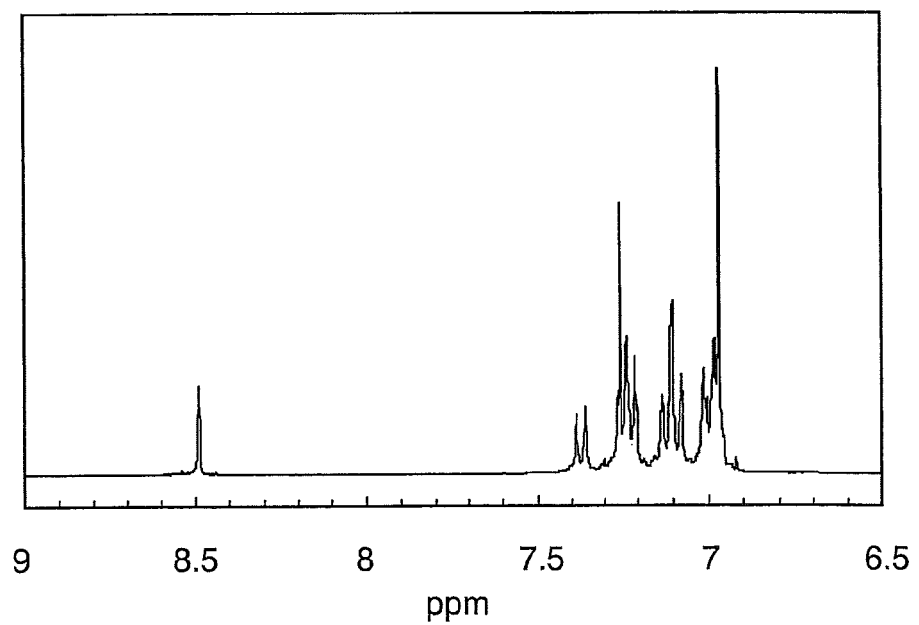

FIGS. 19A and 19B each show a ¹H-NMR chart of DPA-PPr. FIG. 19B is an enlarged chart of a range of 6.5 to 9.0 ppm of the chart of FIG. 19A.

Figure 20:
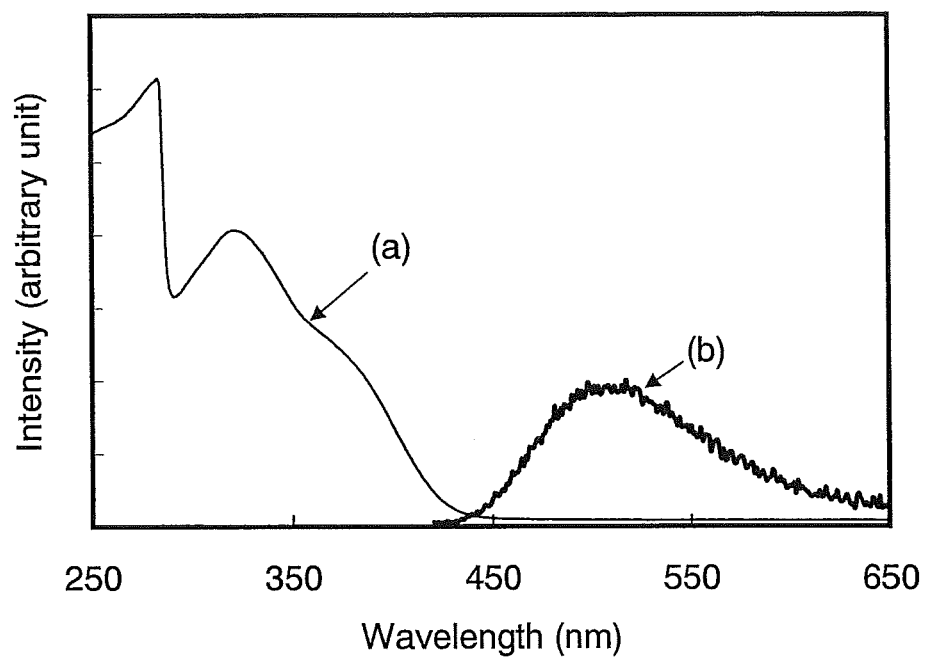
FIG. 20 is a graph showing an absorption spectrum and an emission spectrum in a state where DPAPPr is dissolved in a toluene solution.

FIG. 20 shows an absorption spectrum and an emission spectrum in a state where DPAPPr is dissolved in a toluene solution. The ultraviolet-visible spectrophotometer (V-550, manufactured by JASCO Corporation) was used for the measurement. In FIG. 20, the horizontal axis represents a wavelength (nm) and the vertical axis represents intensity (arbitrary unit). Further, in FIG. 20, a line (a) indicates the absorption spectrum whereas a line (b) indicates the emission spectrum (358 nm of an excited wavelength).

Embodiment 5

Synthesis Example 5

As one example of a pyrazine derivative of the present invention, a synthesis method of a compound represented by a structural formula (s-77), that is, 2,3-bis{4-[N-phenyl-N-(9-phenylcarbazole-3-yl)amino]phenyl}pyrazine (hereinafter, referred to as PCAPPr), will be explained.

Step 1: Synthesis method of N-phenyl-(9-phenylcarbazole-3-yl)amine (hereinafter, referred to as PCA)

(1) Synthesis of 3-bromo-9-phenylcarbazole 24.3 g (100 mmol) of N-phenylcarbazole was dissolved in 600 mL of glacial acetic acid, 17.8 g (100 mmol) of N-bromosuccinimide was slowly added, and the mixture was stirred for approximately 12 hours at the room temperature. This glacial acetic acid solution dropped to 1000 mL of iced water while being stirred. After the drop, a precipitated white solid was washed 3 times with water. This solid was dissolved in 150 mL of diethyl ether, and washed with a saturated sodium hydrogen carbonate solution and water to separate an aqueous layer and an organic layer. This organic layer was dried with magnesium sulfate and filtered. The filtrate was concentrated to obtain a solid. Then, about 50 mL of methanol was added to the solid and the solid was uniformly dissolved by irradiation with ultrasonic waves. By leaving this solution at rest, a white solid was extracted. This white solid was filtered and dried, whereby 28.4 g of a white powdered solid of 3-bromo-9-phenylcarbazole was obtained in the yield of 88% (Synthesis Scheme (j-1)).

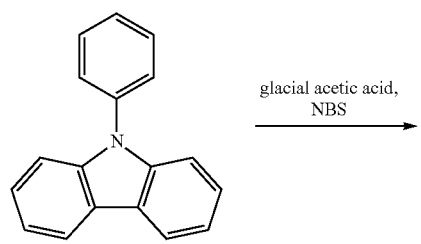

(j-1)

(Synthesis of PCA)

Under nitrogen, 110 mL of dehydrated xylene and 7.0 g (75 mmol) of aniline were added to a mixture containing 19 g (60 mmol) of 3-bromo-9-phenylcarbazole, 340 mg (0.6 mmol) of bis(dibenzylideneacetone)palladium(0) (abbreviated to Pd(dba)₂), 1.6 g (3.0 mmol) of 1,1-bis(diphenylphosphino)ferrocene (abbreviated to DPPF), and 13 g (180 mmol) of sodium-tert-butoxide (abbreviated to t-BuONa). This mixture was then heated and stirred for 7.5 hours at 90° C. under a nitrogen atmosphere. After the reaction was completed, approximately 500 mL of toluene warmed to 50° C. was added to this suspension. Then, the solution was filtered through florisil, alumina, and celite. Hexane and ethyl acetate were added to a solid that was obtained by concentrating the filtrate, and irradiation with ultrasonic waves was performed. An obtained suspension was filtered and dried, whereby 15 g of a light yellow solid of PCA was obtained in the yield of 75% (Synthesis Scheme (j-2)).

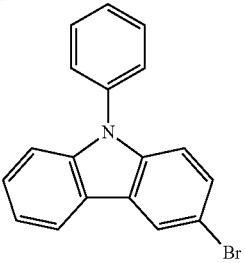

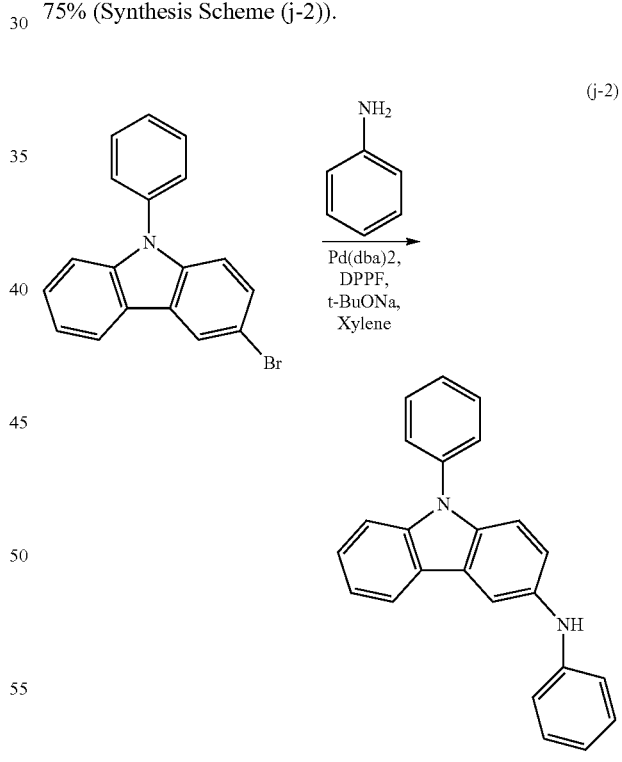

(j-2)

Step 2: Synthesis Method of PCAPPr 1.0 g (2.6 mmol) of PPr, 1.9 g (10.4 mmol) of PCA, and 1.0 g (10.3 mmol) of sodium-tert-butoxide were put into a 100 mL three neck flask, and nitrogen was substituted for the content of the flask. Then, 15 mL of toluene, 0.3 mL of a hexane solution (10 wt %) of tri-tert-butylphosphine, and 0.1 g (0.2 mmol) of bis(dibenzylideneacetone)palladium(0) were added thereto, and this mixture was stirred for 4 hours at 80° C. to be reacted. After the reaction, the reaction mixture was filtered through florisil, celite, and alumina. The filtrate was washed with water and dried with magnesium sulfate, and then filtration was performed. A solid that was obtained by concentrating the filtrate was dissolved in toluene to be purified by silica column chromatography. For the column purification, first, toluene was used as a developing solvent, and then a mixed solvent of toluene:ethyl acetate=9:1 was used as a developing solvent. After the column purification, the obtained solution was re-crystallized with chloroform and hexane, whereby 1.3 g of a yellow solid was obtained in the yield of 57%.

The obtained yellow solid was sublimated and purified by a train sublimation method. The sublimation and purification were performed for 12 hours at 330° C. under the condition of 7 Pa of reduced pressure and 3 mL/min of flow of argon. When the charged amount of the yellow solid was 1.2 g, 0.32 g of a yellow solid of PCAPPr that is an object was obtained in the yield of 26% (Synthesis Scheme (j-3)).

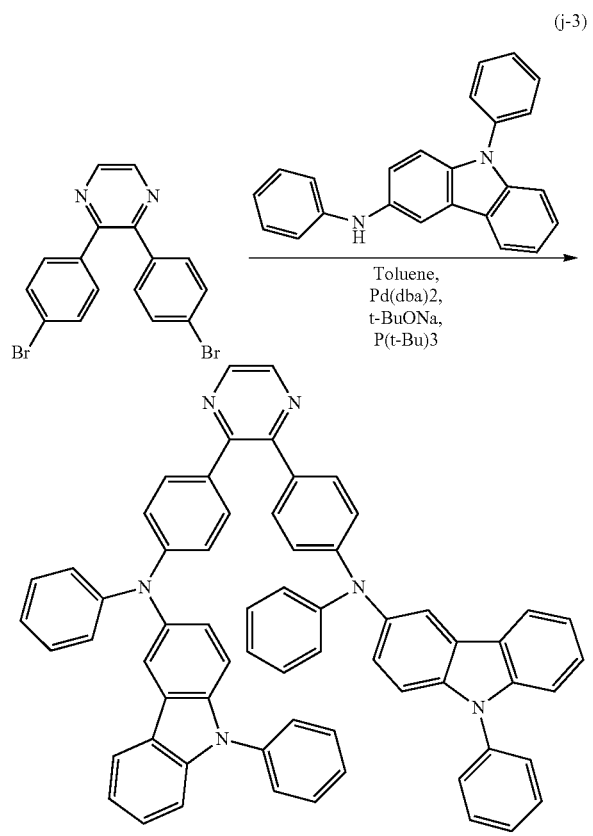

(j-3)

An analysis result by a proton nuclear magnetic resonance method ($^1$H-NMR) of PCAPPr is shown below. As a reference substance, tetramethylsilane (abbreviated to TMS) was used.

$^1$H-NMR (CDCl$_3$, 300 MHz); δ=6.97-7.67 (m, 40H), δ=7.93-7.97 (m, 2H), δ=8.48 (s, 2H)

Figure 21A:
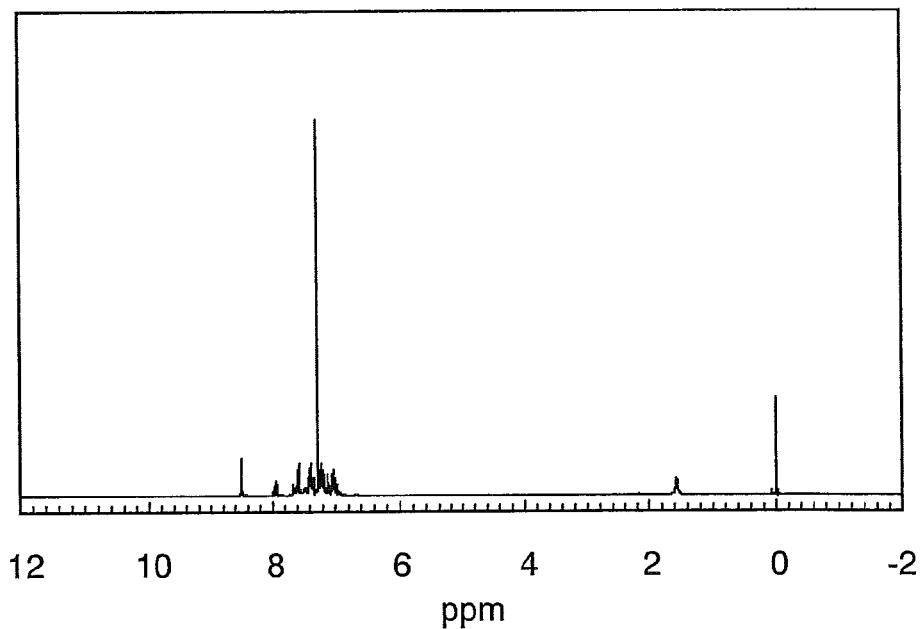
FIGS. 21A and 21B are $^1$H-NMR charts of PCAPPr.
Figure 21B:
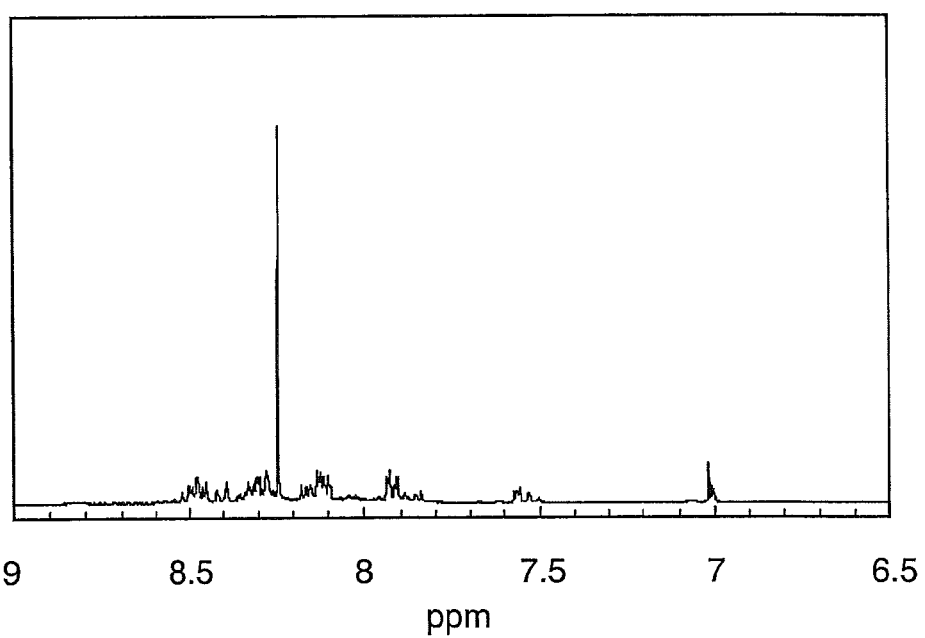

FIGS. 21A and 21B each show a $^1$H-NMR chart of PCAPPr. FIG. 21B is an enlarged chart of a range of 6.5 to 9.0 ppm of the chart of FIG. 21A.

Figure 22:
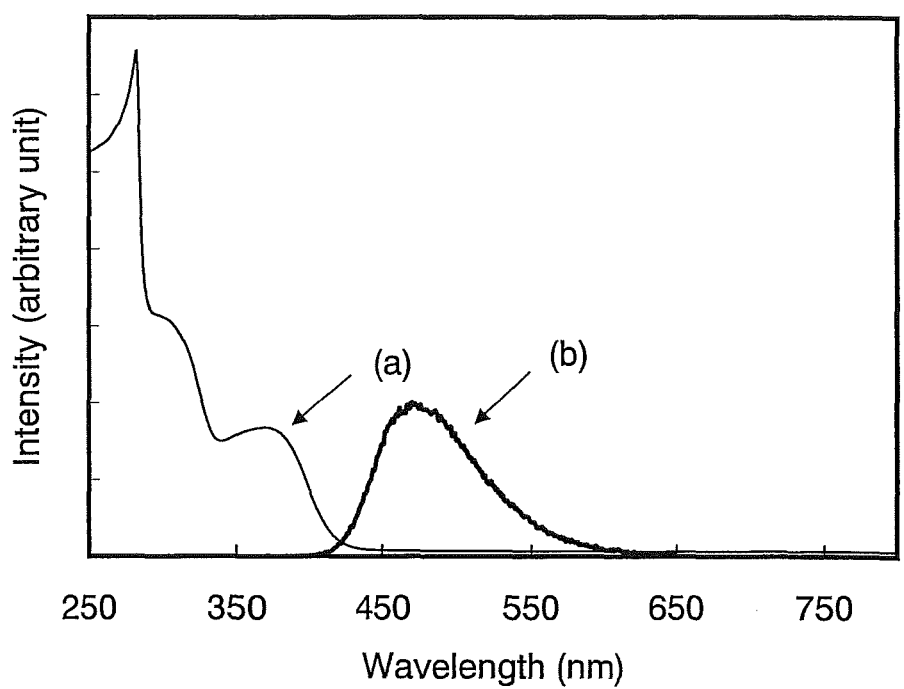
FIG. 22 is a graph showing an absorption spectrum and an emission spectrum in a state where PCAPPr is dissolved in a toluene solution.

FIG. 22 shows an absorption spectrum and an emission spectrum in a state where PCAPPr is dissolved in a toluene solution. The ultraviolet-visible spectrophotometer (V-550, manufactured by JASCO Corporation) was used for the measurement. In FIG. 22, the horizontal axis represents a wavelength (nm) and the vertical axis represents intensity (arbitrary unit). Further, in FIG. 22, a line (a) indicates the absorption spectrum whereas a line (b) indicates the emission spectrum (367 nm of an excited wavelength).

Figure 23:
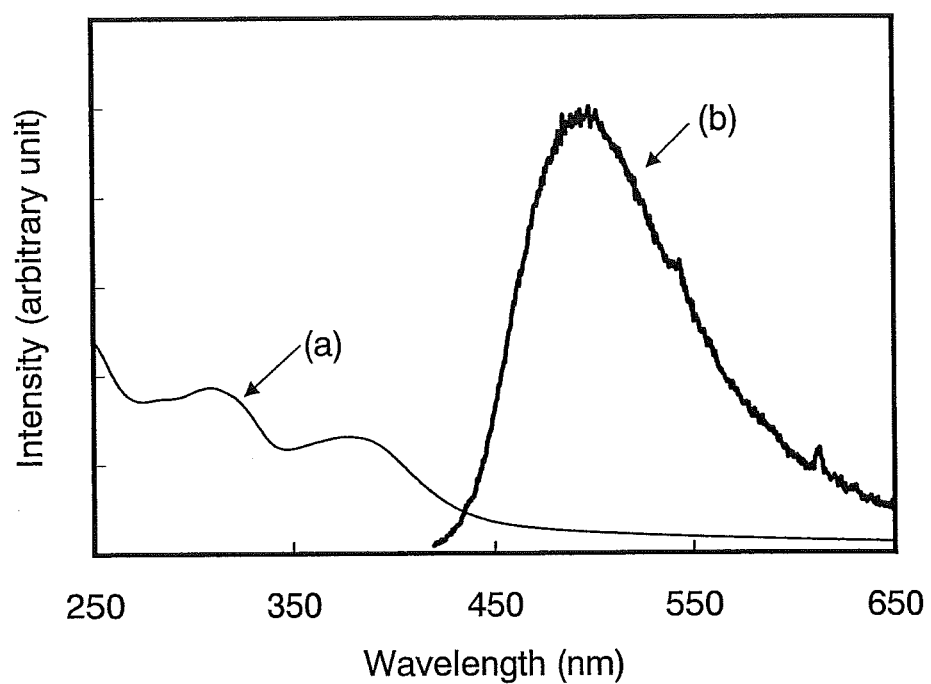
FIG. 23 is a graph showing an absorption spectrum and an emission spectrum in a single film state of PCAPPr.

FIG. 23 shows an absorption spectrum and an emission spectrum in a single film state of PCAPPr. The ultraviolet-visible spectrophotometer (V-550, manufactured by JASCO Corporation) was used for the measurement. In FIG. 23, the horizontal axis represents a wavelength (nm) and the vertical axis represents intensity (arbitrary unit). Further, in FIG. 23, a line (a) indicates the absorption spectrum whereas a line (b) indicates the emission spectrum (376 nm of an excited wavelength).

Embodiment 6

Synthesis Example 6

As one example of a pyrazine derivative of the present invention, a synthesis method of a compound represented by a structural formula (s-103), that is, 2,3-bis(4-{N-[4-(carbazole-9-yl)phenyl]-N-phenylamino}phenyl)pyrazine (hereinafter, referred to as YGAPPr), will be explained.

Step 1: Synthesis method of 4-(carbazole-9-yl)diphenylamine (hereinafter, referred to as YGA)

(1) Synthesis of 9-(4-bromophenyl)carbazole 56 g (240 mmol) of p-dibromobenzene, 31 g (180 mmol) of carbazole, 4.6 g (24 mmol) of copper iodide, 66 g (480 mmol) of potassium carbonate, and 2.1 g (8 mmol) of 18-crown-6-ether were put into a 300 mL three-necked flask, and nitrogen was substituted for the content of the flask. Then, 8 mL of N—N'-dimetylpropyleneurea was added thereto, and this mixture was stirred for 6 hours at 180° C. to be reacted. After the reaction, cooling of the reaction mixture to the room temperature was performed, and the precipitated object was removed by suction filtration. The filtrate was washed with dilute hydrochloric acid, a saturated sodium hydrogen carbonate solution, and a saturated saline solution, in this order, and then dried with magnesium sulfate. After drying, filtration was performed, and an oily substance that was obtained by concentrating the filtrate was purified by silica column chromatography. For the column purification, a mixed solvent of hexane:ethyl acetate=9:1 was used as a developing solvent. After the column purification, an obtained solution was re-crystallized with chloroform and hexane, whereby 21 g of a light brown solid of 9-(4-bromophenyl)carbazole was obtained in the yield of 35% (Synthesis Scheme (k-1)).

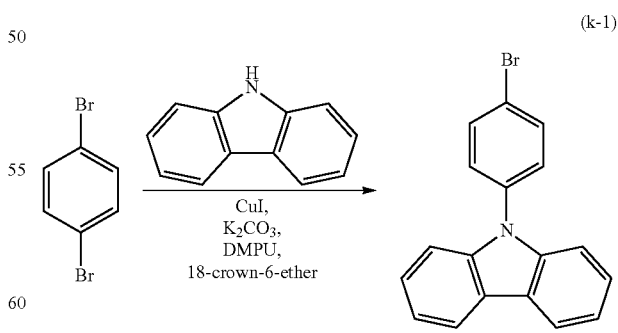

(k-1)

(2) Synthesis of YAG 5.4 g (17 mmol) of 9-(4-bromophenyl)carbazole, 1.8 mL (20 mmol) of aniline, 0.1 g (0.2 mmol) of bis(dibenzylideneacetone)palladium(0), and 3.9 g (40 mmol) of sodium-tert-butoxide were put into a 200 mL three neck flask. After nitrogen was substituted for the content of the flask, 0.1 mL of a hexane solution (10 wt %) of tri-tert-butylphosphine and 50 mL of toluene were added. This mixture was stirred for 6 hours at 80° C. to be reacted. After the reaction, the reaction mixture was filtered through florisil, celite, and alumina. The filtrate was washed with water and a saturated saline solution, dried with magnesium sulfate, and filtration was naturally performed. An oily substance that was obtained by concentrating the filtrate was purified by silica gel column chromatography, whereby 4.1 g of a white solid of YGA was obtained in the yield of 73% (Synthesis Scheme (k-2)). For the column purification, a mixed solvent of hexane:ethyl acetate=9:1 was used as a developing solvent.

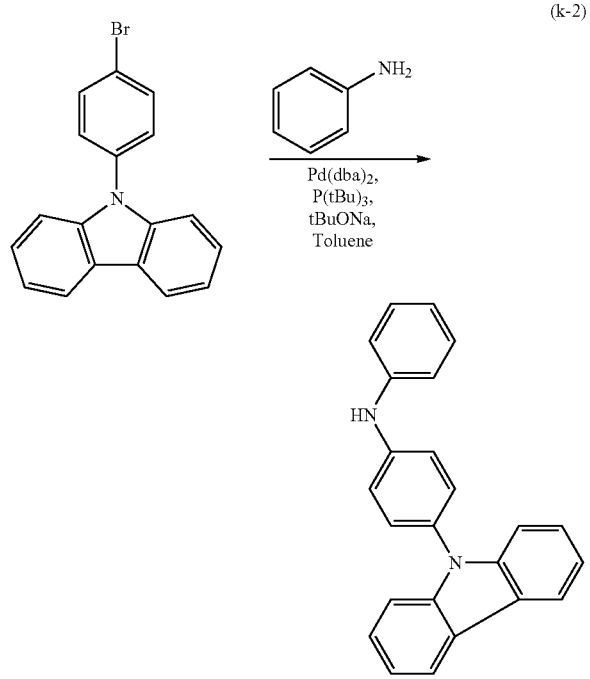

(k-2)

Step 2: Synthesis Method of YGAPPr 2.0 g (5.1 mmol) of PPr, 3.5 g (10.5 mmol) of YGA, and 1.9 g (20.1, mmol) of sodium-tert-butoxide were put into a 100 mL three neck flask, and nitrogen was substituted for the content of the flask. Then, 30 mL of toluene and 0.2 mL of a hexane solution (10 wt %) of tri-tert-butylphosphine were added, and nitrogen was substituted for the content of the flask again. Moreover, 0.2 g (0.4 mmol) of bis(dibenzylideneacetone)palladium(0) was added thereto, and this mixture was heated and stirred for 5 hours at 120° C. to be reacted. After the reaction, the reaction mixture was filtered through celite. The filtrate was washed with water and dried with magnesium sulfate, and then filtration was performed. A solid that was obtained by concentrating the filtrate was dissolved in toluene to be purified by silica column chromatography. For the column purification, first, toluene was used as a developing solvent, and then a mixed solvent of toluene:ethyl acetate=9:1 was used as a developing solvent. After the column purification, an obtained solution was re-crystallized with chloroform and hexane, whereby 4.1 g of a yellow solid was obtained in the yield of 89%.

The obtained yellow solid was sublimated and purified by a train sublimation method. The sublimation and purification were performed for 12 hours at 320° C. under the condition of 7 Pa of reduced pressure and 3 mL/min of flow of argon. When the charged amount of the yellow solid was 3.4 g, 0.65 g of a yellow solid of YGAPPr that is an object was obtained in the yield of 19% (Synthesis Scheme (k-3)).

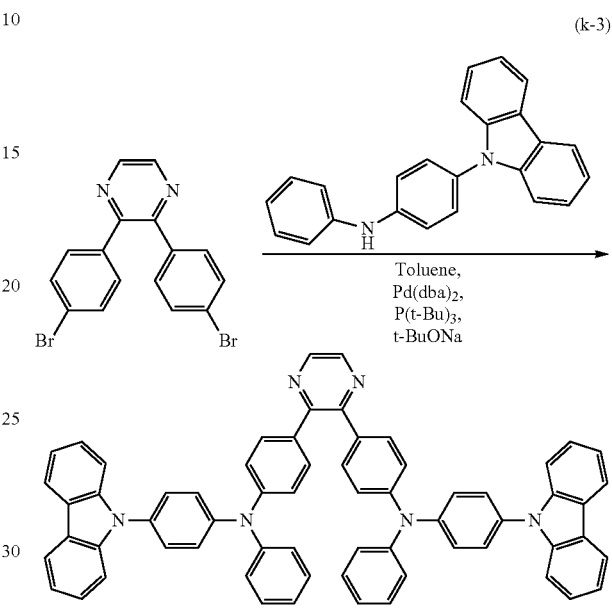

(k-3)

An analysis result by a proton nuclear magnetic resonance method ($^1$H-NMR) of YGAPPr is shown below. As a reference substance, tetramethylsilane (abbreviated to TMS) was used.

$^1$H-NMR (300 MHz, CDCl$_3$): δ=7.11 (d, J=12.0, 4H), δ=7.16-7.44 (m, 26H), δ=7.48 (d, J=8.4, 4H), δ=8.13 (d, J=7.8, 4H), δ=8.55 (s, 2H)

Figure 24A:
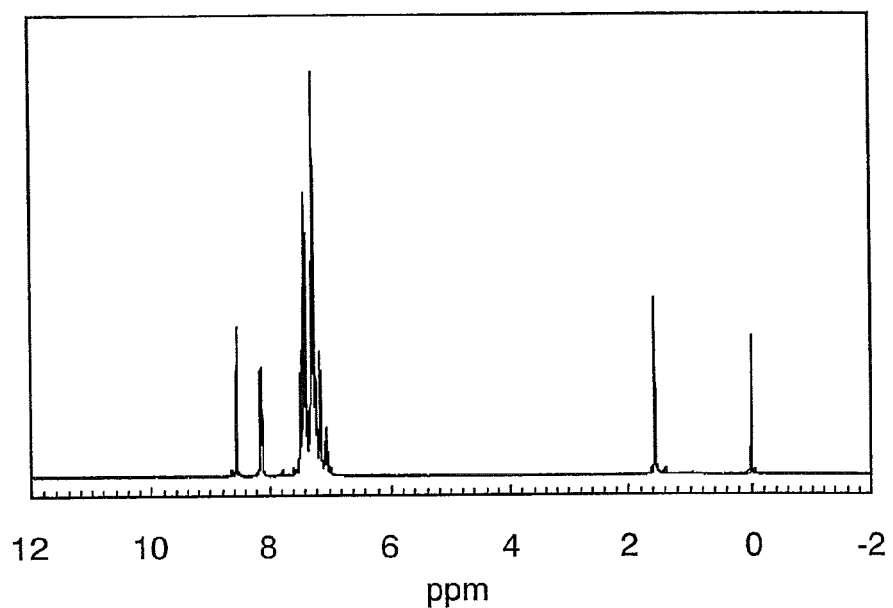
FIGS. 24A and 24B are $^1$H-NMR charts of YGAPPr.
Figure 24B:
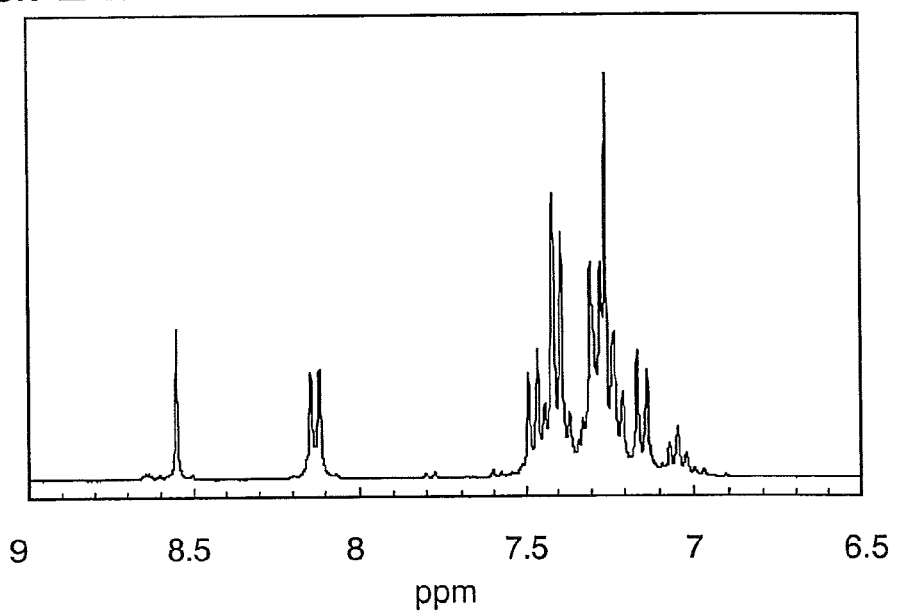

FIGS. 24A and 24B each show a $^1$H-NMR chart of YGA-PPr. FIG. 24B is an enlarged chart of a range of 6.5 to 9.0 ppm of the chart of FIG. 24A.

Figure 25:
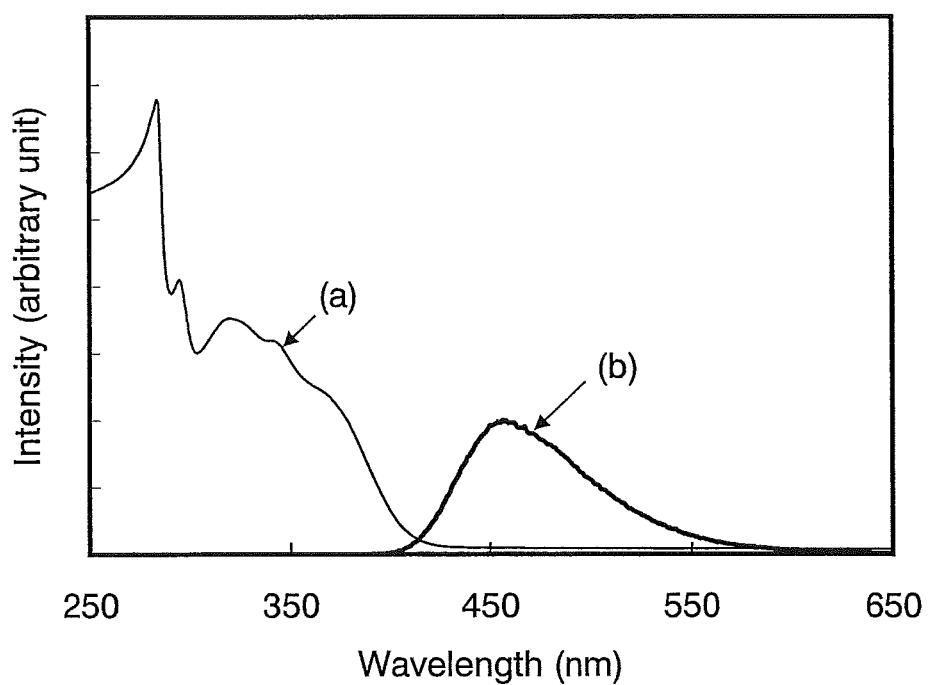
FIG. 25 is a graph showing an absorption spectrum and an emission spectrum in a state where YGAPPr is dissolved in a toluene solution.

FIG. 25 shows an absorption spectrum and an emission spectrum in a state where YGAPPr is dissolved in a toluene solution. The ultraviolet-visible spectrophotometer (V-550, manufactured by JASCO Corporation) was used for the measurement. In FIG. 25, the horizontal axis represents a wavelength (nm) and the vertical axis represents intensity (arbitrary unit). Further, in FIG. 25, a line (a) indicates the absorption spectrum whereas a line (b) indicates the emission spectrum (355 nm of an excited wavelength).

Figure 26:
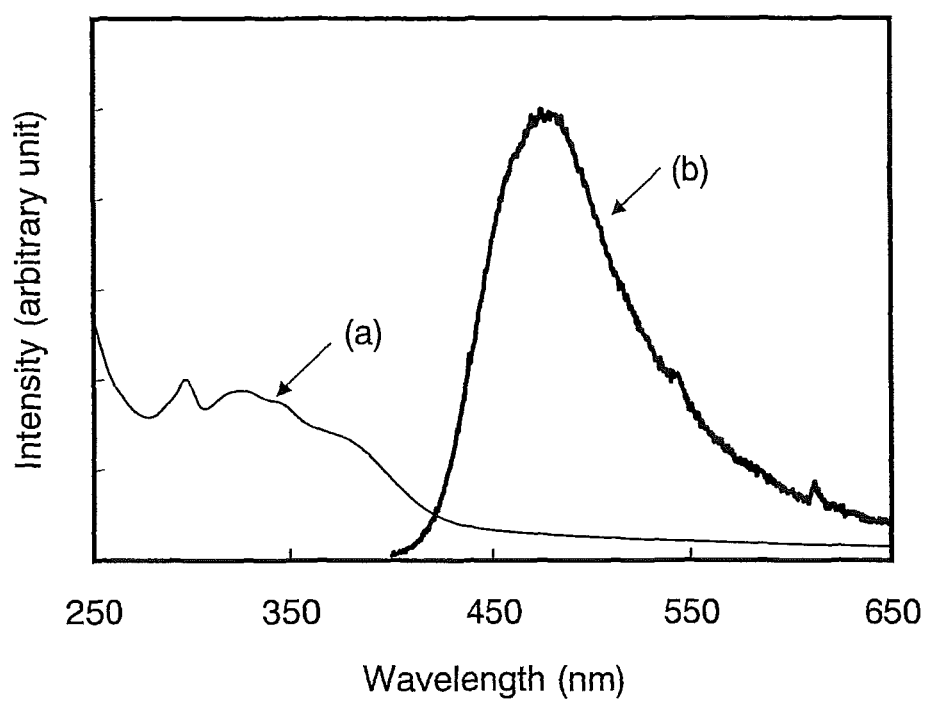
FIG. 26 is a graph showing an absorption spectrum and an emission spectrum in a single film state of YGAPPr.

FIG. 26 shows an absorption spectrum and an emission spectrum in a single film state of YGAPPr. The ultraviolet-visible spectrophotometer (V-550, manufactured by JASCO Corporation) was used for the measurement. In FIG. 26, the horizontal axis represents a wavelength (nm) and the vertical axis represents intensity (arbitrary unit). Further, in FIG. 26, a line (a) indicates the absorption spectrum whereas a line (b) indicates the emission spectrum in the single film state (375 nm of an excited wavelength).

Embodiment 7

Figure 27:
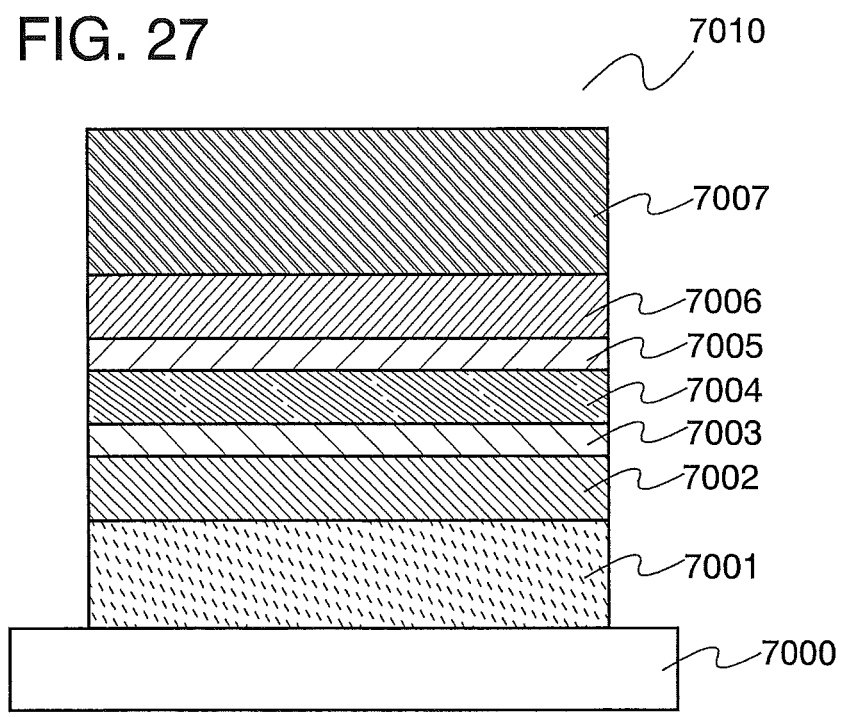
FIG. 27 is a view showing an example of a light emitting element of Embodiment 7.

In this embodiment, an example of a light emitting element will be specifically described, in which DPhAPPr (the struc tural formula (s-13)) that is one example of a pyrazine derivative of the present invention synthesized in Synthesis Example 3 of Embodiment 3 is used as a host material of a light emitting layer, and a phosphorescent compound is used as a guest material. An element structure is shown in FIG. 27.

First, a glass substrate 7000 over which indium tin oxide containing silicon (ITSO) with a thickness of 100 nm is formed was prepared. A periphery of the ITSO was covered with an insulating film. At this time, the insulating film was formed so that a surface of the ITSO was exposed with a size of 2×2 mm. It is to be noted that the ITSO is a first electrode 7001 serving as an anode of a light emitting element. As a pretreatment for forming a light emitting element over the substrate 7000 over which the first electrode 7001 was formed, a surface of the substrate 7000 was washed with a porous resin brush, baked for 1 hour at 200° C., and subjected to UV ozone treatment for 370 seconds.

Next, the substrate 7000 was fixed to a holder provided in a vacuum evaporation device in such a way that a surface over which the first electrode 7001 was formed faces downward.

Subsequently, the pressure in the vacuum evaporation device was reduced to $10^{-4}$ Pa. NPB represented by the following structural formula (s-116) and molybdenum oxide (VI) were co-evaporated over the first electrode 7001 so that the ratio thereof is to be NPB:molybdenum oxide (VI)=4:1 in the mass ratio, thereby forming a hole injecting layer 7002. The hole injecting layer 7002 was formed to have a thickness of 50 nm. It is to be noted that the co-evaporation is an evaporation method in which a plurality of substances different from each other is simultaneously evaporated from evaporation sources different from each other.

Then, 10 nm of NPB was evaporated over the hole injecting hole layer 7002, thereby forming a hole transporting layer 7003. In addition, DPhAPPr (the structural formula (s-13)) that is a pyrazine derivative of the present invention and a phosphorescent compound that is (acetylacetonato)bis[2,3-bis(4-fluorophenyl)quinoxalinato]iridium(III) (hereinafter, referred to as Ir(Fdpq)$_2$(acac)) represented by the following structural formula (s-117) were co-evaporated over the hole transporting layer 7003 so that the ratio thereof is set to be DPhAPPr:Ir(Fdpq)$_2$(acac)=1:0.05 in the mass ratio, thereby forming a light emitting layer 7004. The light emitting layer 7004 was formed to have a thickness of 30 nm. Accordingly, Ir(Fdpq)$_2$(acac) is dispersed in a layer made from DPhAPPr (the structural formula (s-13)) that is a pyrazine derivative of the present invention.

Then, 10 nm of BAlq represented by the following structural formula (s-118) was evaporated over the light emitting layer 7004 to have a thickness of 10 nm, thereby forming an electron transporting layer 7005. In addition, Alq$_3$ represented by the following structural formula (s-119) and lithium (Li) were co-evaporated over the electron transporting layer 7005 so that the ratio thereof is set to be Alq$_3$:Li=1:0.01 in the mass ratio, thereby forming an electron injecting layer 7006. The electron injecting layer was formed to have a thickness of 50 nm.

Finally, 200 nm of aluminum as a second electrode 7007 was foiled over the electron injecting layer 7006, thereby obtaining a light emitting element 7010 of this embodiment. It is to be noted that the second electrode 7007 served as a cathode. Further, in the above evaporation process, a heat resistance method was used for the entire evaporation.

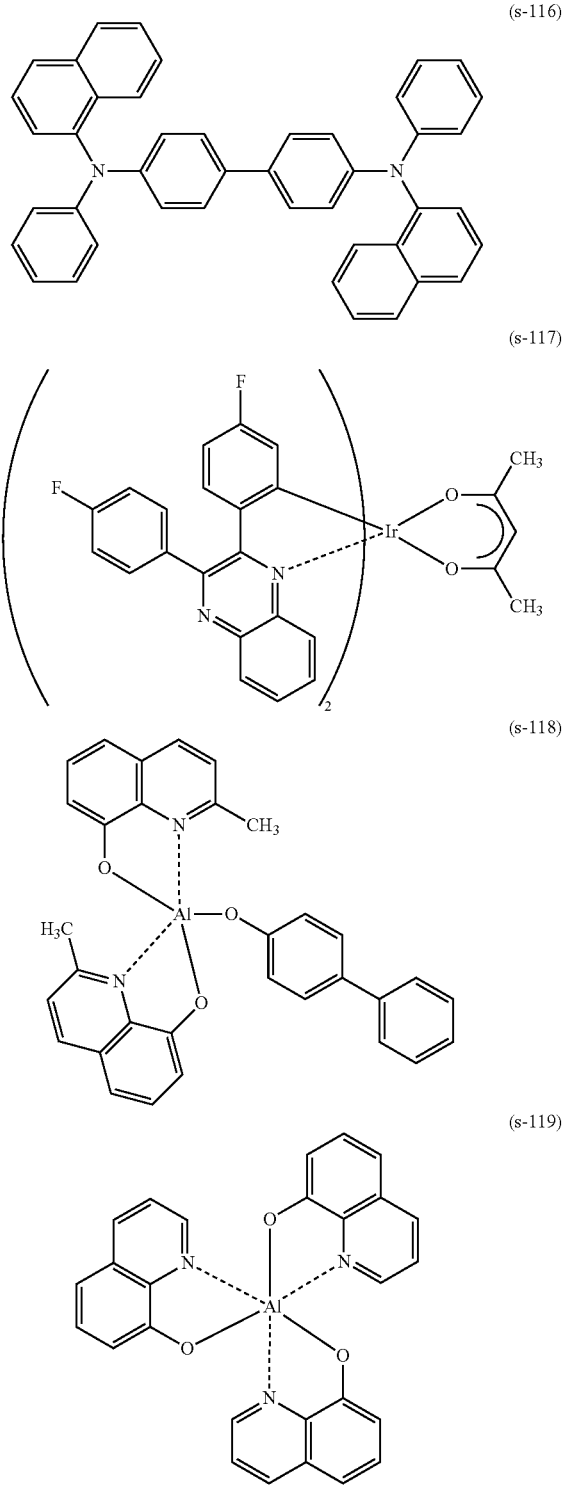

By placing the light emitting element 7010 of this embodiment in a gloved box under a nitrogen atmosphere, sealing of the light emitting element 7010 was performed so that the light emitting element 7010 was not exposed to the atmospheric air. Then, an operation characteristic of the light emitting element 7010 of this embodiment was measured. The measurement was performed at the room temperature (in the atmosphere where the temperature was held at 25° C.).

Figure 28:
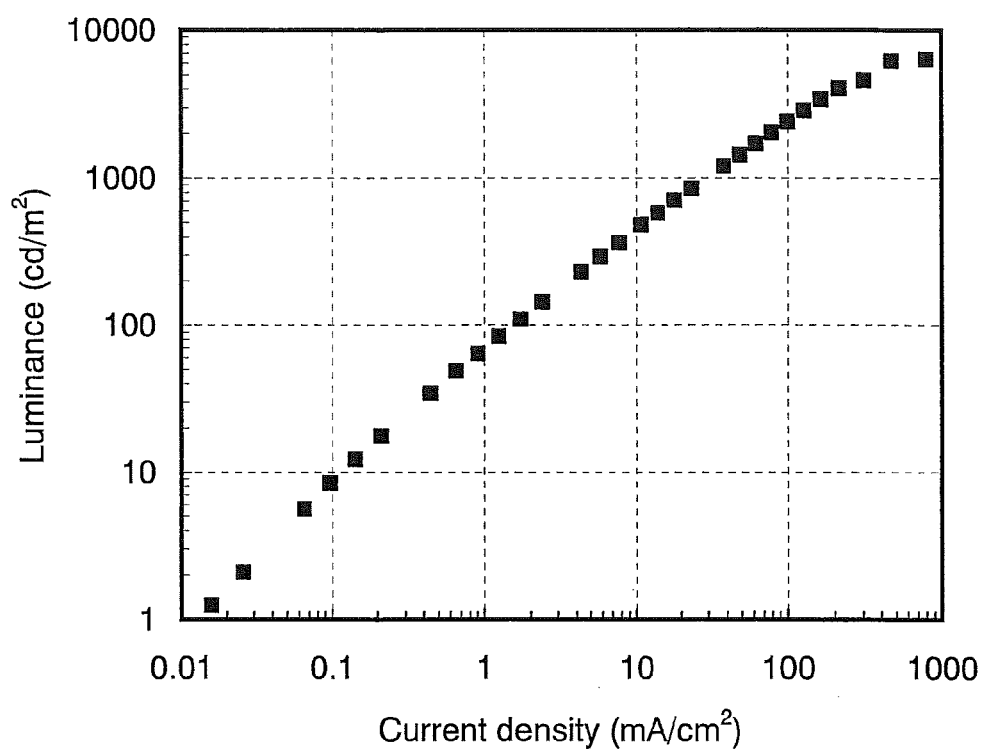
FIG. 28 is a graph showing a current density-luminance characteristic of a light emitting element of Embodiment 7.
Figure 29:
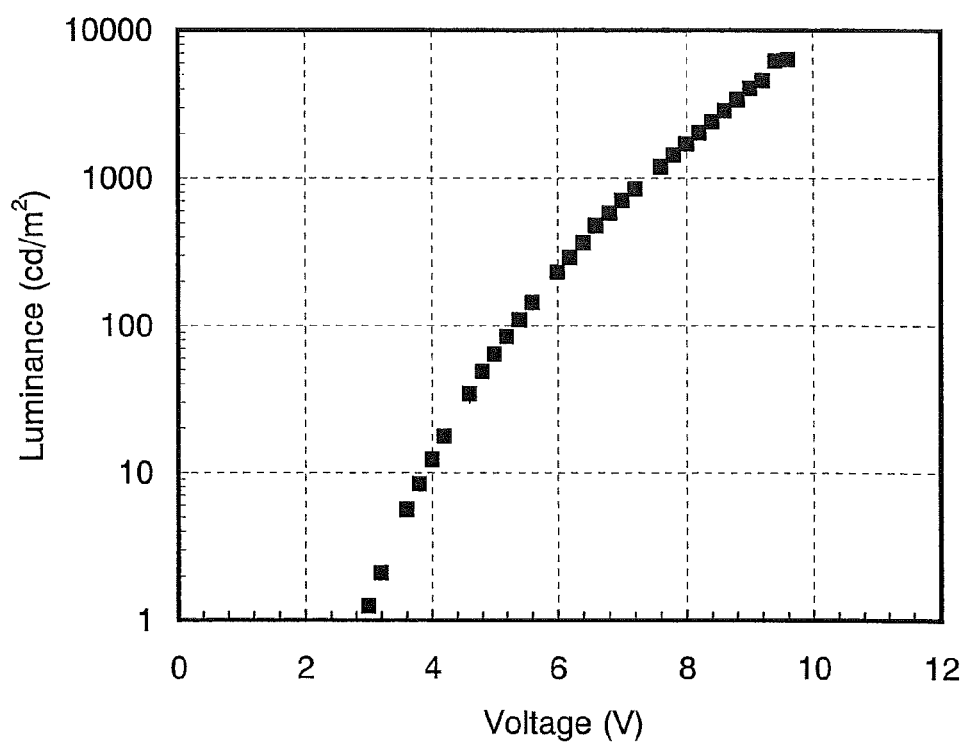
FIG. 29 is a graph showing a voltage-luminance characteristic of a light emitting element of Embodiment 7.

FIG. 28 shows a current density-luminance characteristic of the light emitting element 7010 of this embodiment, and FIG. 29 shows a voltage-luminance characteristic thereof. In the light emitting element 7010 of this embodiment, by applying a voltage of 7.2 V, the current flowed with the current density of 23.4 mA/cm$^2$, and light was emitted with the luminance of 843 cd/m$^2$. The CIE chromaticity coordinate at this time was (x=0.70, y=0.29), and light emission with deep red color was exhibited. A peak wavelength of an emission spectrum was 640 nm, and light emission from Ir(Fdpq)$_2$(acac) that is a guest material was obtained.

Figure 30:
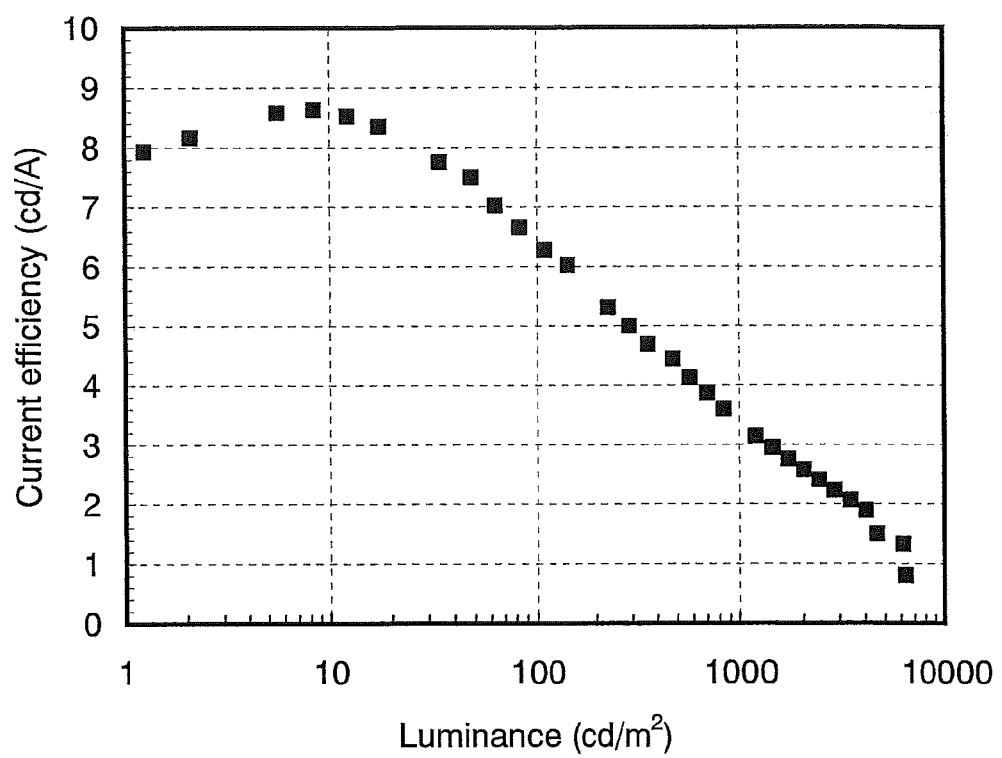
FIG. 30 is a graph showing a luminance-current efficiency characteristic of a light emitting element of Embodiment 7.
Figure 31:
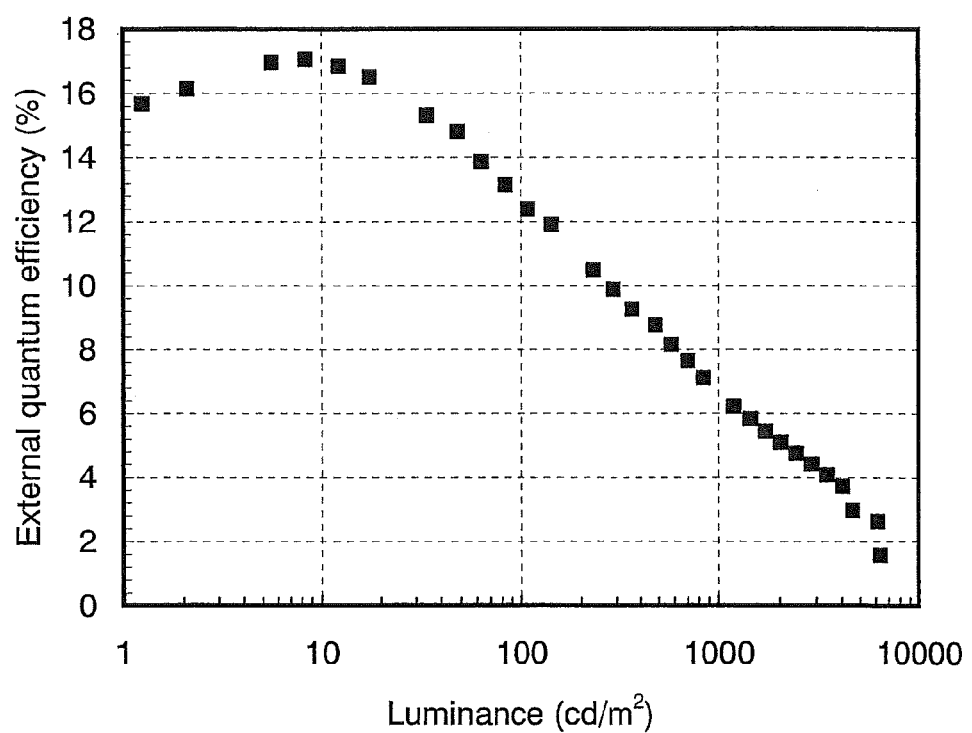
FIG. 31 is a graph showing a luminance-external quantum efficiency characteristic of a light emitting element of Embodiment 7.

FIG. 30 shows a luminance-current efficiency characteristic of the light emitting element 7010. FIG. 31 shows a graph in which a vertical axis of FIG. 30 is converted to external quantum efficiency. As shown in FIG. 30 and FIG. 31, the maximum current efficiency was 8.63 cd/A, the external quantum efficiency at this time was 17.0%, and extremely high light emitting efficiency was shown.

According to the above, a light emitting element is manufactured by using a pyrazine derivative of the present invention as a host material of a light emitting layer and a phosphorescent compound as a guest material, whereby it was found that a light emitting element having extremely high light emitting efficiency can be obtained.

Embodiment 8

Figure 32:
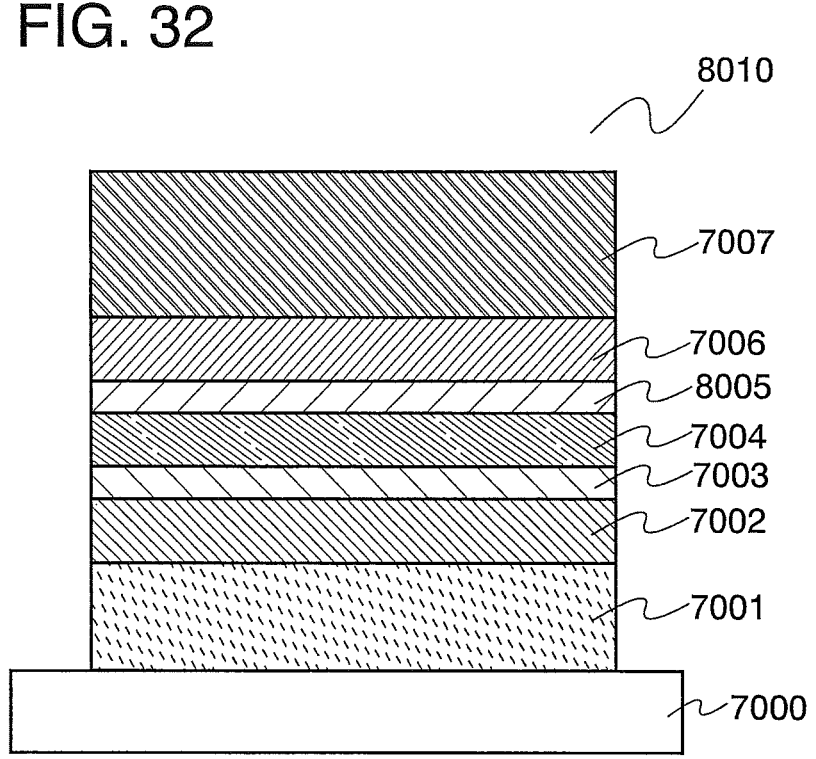
FIG. 32 is a view showing an example of a light emitting element of Embodiment 8.

In this embodiment, a light emitting element having different structure from that shown in Embodiment 7 will be explained. It is to be noted that the light emitting element except for an electron transporting layer 8005 has the same structure as that of Embodiment 7; therefore, explanation thereof is omitted. An element structure is shown in FIG. 32.

In this embodiment, Alq$_3$ was used for the electron transporting layer 8005 replacing with BAlq used in Embodiment 7. The other structure is similar to that of Embodiment 7.

Figure 33:
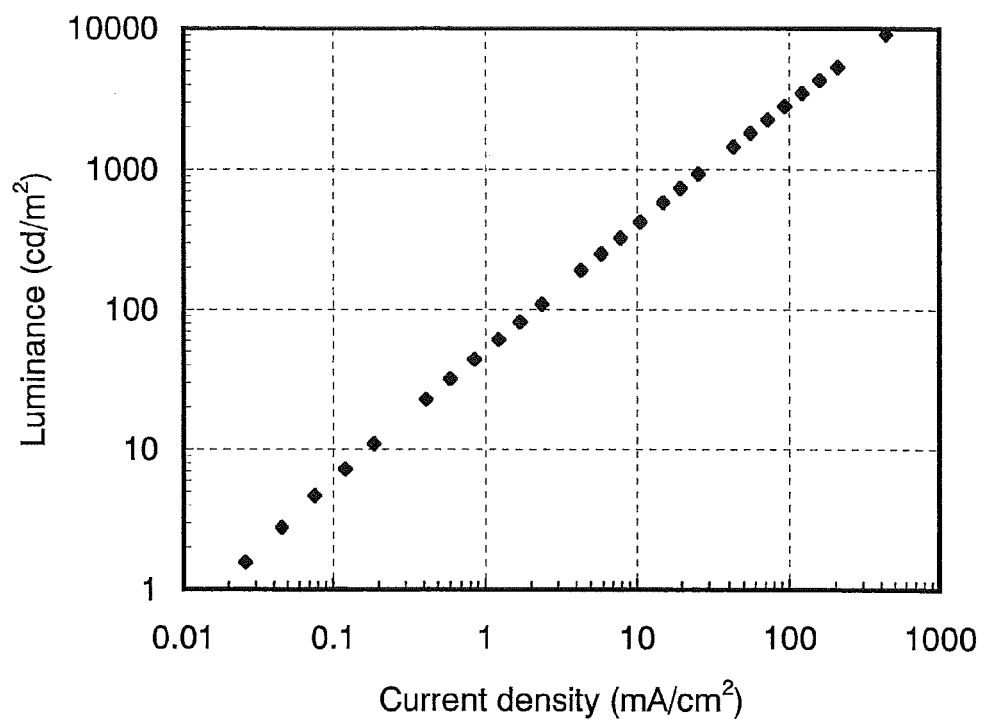
FIG. 33 is a graph showing a current density-luminance characteristic of a light emitting element of Embodiment 8.
Figure 34:
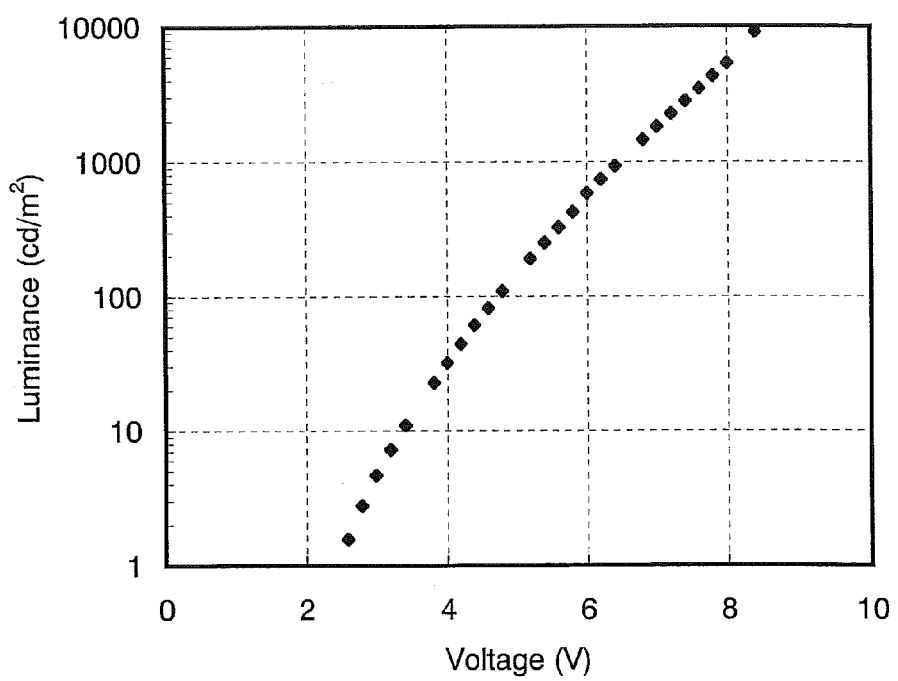
FIG. 34 is a graph showing a voltage-luminance characteristic of a light emitting element of Embodiment 8.

FIG. 33 shows a current density-luminance characteristic of a light emitting element 8010 of this embodiment, and FIG. 34 shows a voltage-luminance characteristic thereof. In the light emitting element 8010 of this embodiment, by applying a voltage of 6.4 V, a current flowed with the current density of 25.5 mA/cm$^2$, and light was emitted with the luminance of 927 cd/m$^2$. The CIE chromaticity coordinate at this time was (x=0.68, y=0.31), and light emission with deep red color was exhibited. A peak wavelength of an emission spectrum was 640 nm, and light emission from Ir(Fdpq)$_2$(acac) that is a guest material can be obtained.

Figure 35:
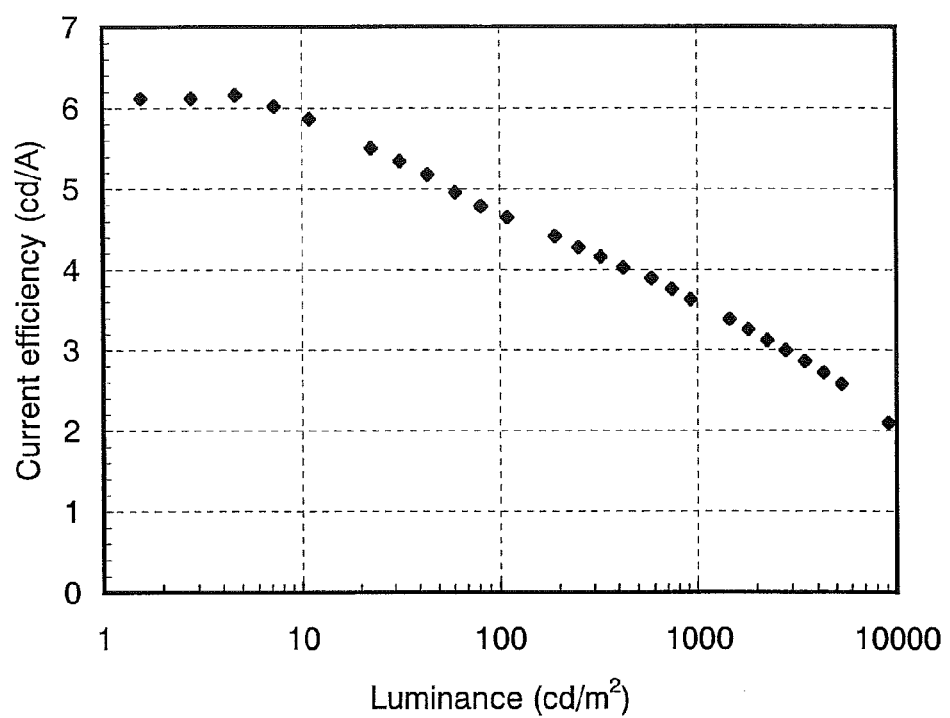
FIG. 35 is a graph showing a luminance-current efficiency characteristic of a light emitting element of Embodiment 8.
Figure 36:
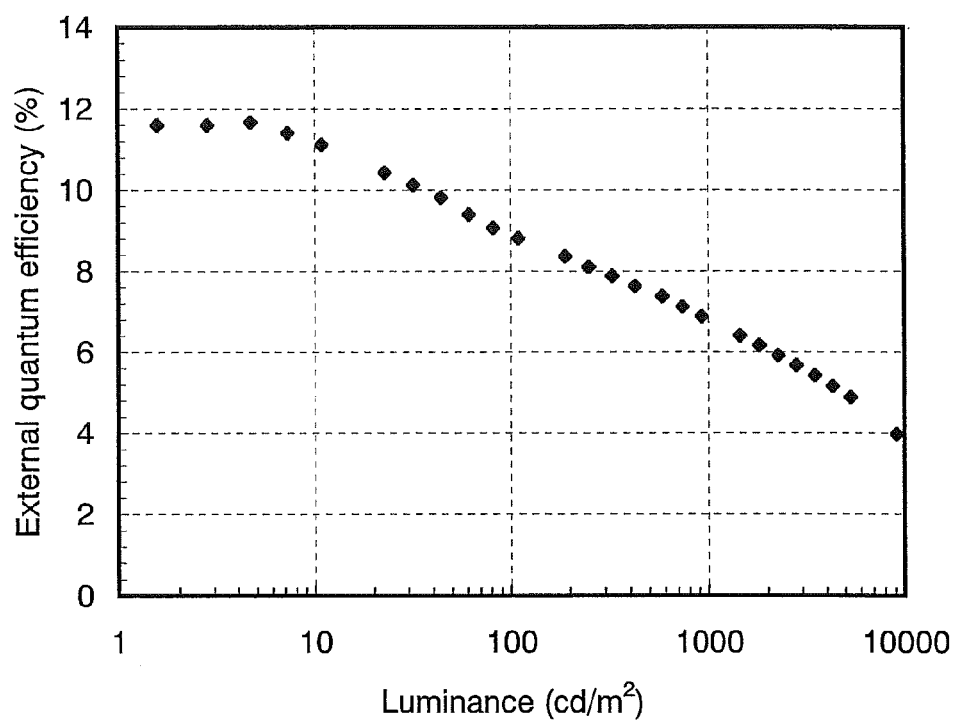
FIG. 36 is a graph showing a luminance-external quantum efficiency characteristic of a light emitting element of Embodiment 8.

FIG. 35 shows a luminance-current efficiency characteristic of the light emitting element 8010 of this embodiment. FIG. 36 is a graph in which a vertical axis of FIG. 35 is converted to external quantum efficiency. As shown in FIG. 35 and FIG. 36, the maximum current efficiency was 6.16 cd/A, the external quantum efficiency at this time was 11.7%, and high light emitting efficiency was shown.

According to the above, a light emitting element is manufactured by using a pyrazine derivative of the present invention as a host material of the light emitting layer 7004 and a phosphorescent compound as a guest material, whereby it was found that a light emitting element having extremely high light emitting efficiency can be obtained. In this embodiment, Alq$_3$ is used for the electron transporting layer 8005 provided in contact with the light emitting layer 7004. Alq$_3$ is generally known as a quench for quenching light emission of a phosphorescent compound. However, in this embodiment, the electron transporting layer 8005 made from Alq$_3$ is in contact with the light emitting layer 7004, and a light emitting element having high light emitting efficiency can be achieved. As a reason of this, it is considered that a pyrazine derivative of the present invention has a bipolar property for transporting electrons as well as holes.

Embodiment 9

Synthesis Example 7

As one example of a pyrazine derivative of the present invention, a synthesis method of a compound represented by a structural formula (s-14), that is, 2,3-bis[4-(N,N-diphenylamino)phenyl]5,6-diphenylpyrazine (hereinafter, referred to as DPhAPPPr), will be explained.

Step 1: Synthesis method of
2,3-bis(4-bromophenyl)-5,6-diphenylpyrazine
(hereinafter, referred to as PPPr)

3.0 g (8.1 mmol) of 4,4'-dibromobenzyl and 1.8 g (8.1 mmol) of meso-diphenlyetylenediamine were put into a 300 mL three neck flask, 100 mL of ethanol was added thereto, and this mixture was heated and stirred for 5 hours at 80° C. to be reacted. After the reaction, the reaction solution was concentrated, and 2.3 g of manganese dioxide and 100 mL of chloroform were added thereto. Then, the solution was further heated and stirred for 1 hour at 80° C. to be reacted. After the reaction, the reaction solution was washed with water, and an aqueous layer and an organic layer were separated. The organic layer was subjected to suction filtration through celite. A solid that was obtained by concentrating the filtrate was washed with a mixed solvent of chloroform and hexane, whereby 1.6 g of a white powder solid of PPPr was obtained in the yield of 37% (Synthesis Scheme (1-1)).

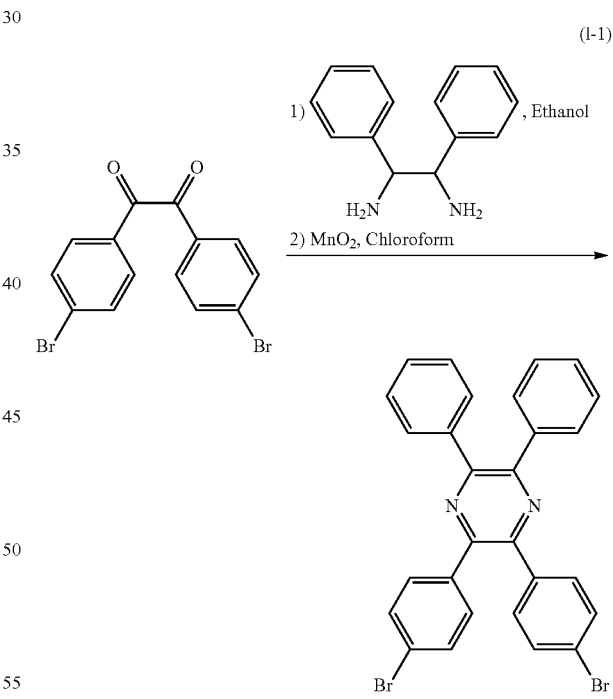

(1-1)

Step 2: Synthesis Method of DPhAPPPr 3.2 g (5.9 mmol) of PPPr, 2.0 g (12 mmol) of DPhA, and 1.5 g (16 mmol) of sodium-tert-butoxide were put into a 200 mL three neck flask. After nitrogen was substituted for the content of the flask, 30 mL of toluene, 0.1 mL of a hexane solution (10 wt %) of tri-tert-butylphosphine, and 0.1 g (0.2 mmol) of bis(dibenzylideneacetone)palladium(0) were added thereto. This mixture was heated and stirred for 8 hours at 120° C. to be reacted. After the reaction, chloroform was added to the reaction mixture to dissolve the precipitated object, and the reaction mixture was subjected to suction and filtration through florisil, celite, and alumina. The filtrate was washed with water, dried with magnesium sulfate, and subjected to suction and filtration. Then, by concentrating the filtrate, an obtained solid was washed with a mixed solvent of toluene and methanol, and re-crystallization was performed with chloroform and methanol, whereby 1.8 g of a yellow powder solid was obtained in the yield of 42%.

The obtained yellow solid was sublimated and purified by a train sublimation method. The sublimation and purification were performed for 15 hours at 294° C. under the condition of 7 Pa of reduced pressure and 3 mL/min of flow of argon. When the charged amount of the obtained yellow solid was 1.8 g, 1.3 g of a yellow solid of DPhAPPPr that is an object was obtained in the yield of 72% (Synthesis Scheme (l-2)).

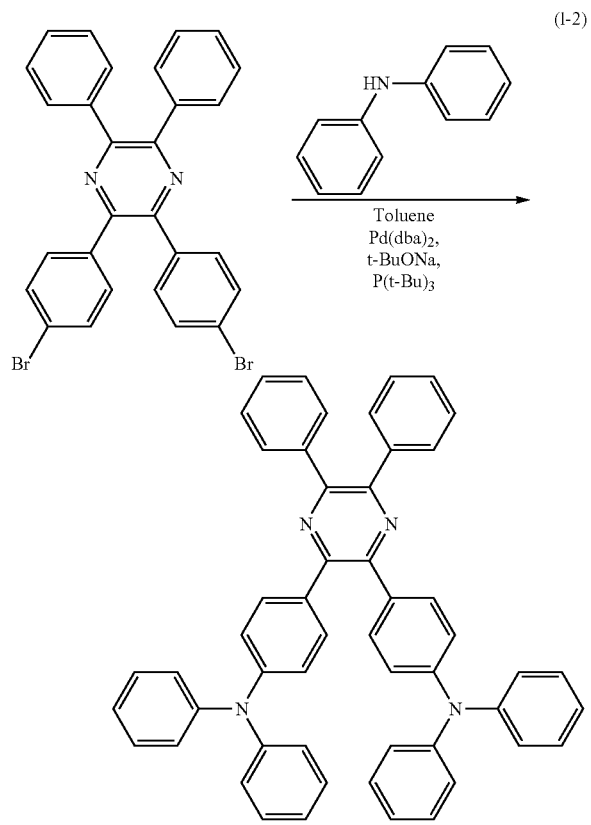

(l-2)

An analysis result by a proton nuclear magnetic resonance method ($^1$H-NMR) of DPhAPPPr that was obtained is shown below. As a reference substance, TMS was used.

$^1$H-NMR (300 MHz, CDCl$_3$); δ=6.95-7.18 (m, 16H), δ=7.22-7.40 (m, 14H), δ=7.57 (d, J=8.3, 4H), δ=7.60-7.68 (m, 4H)

Figure 37A:
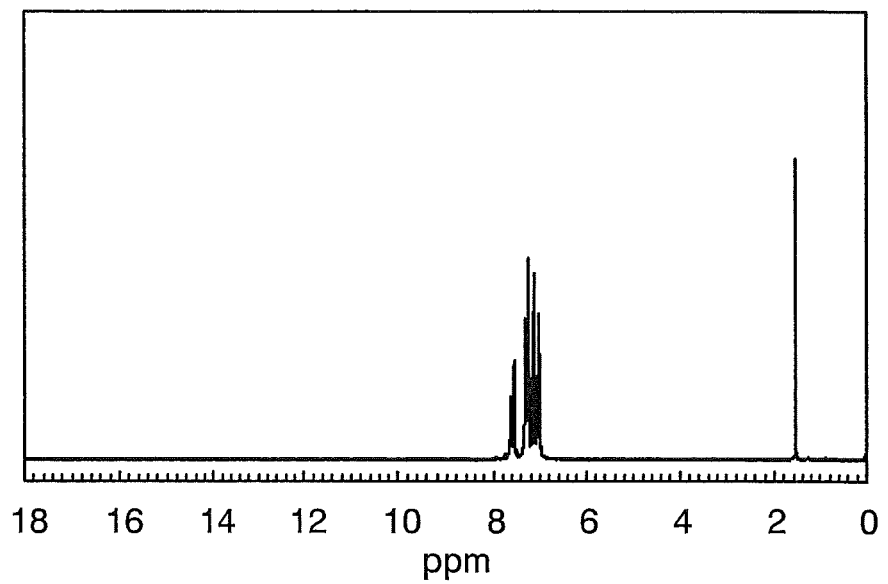
FIGS. 37A and 37B are $^1$H-NMR charts of DPhAPPPr.
Figure 37B:
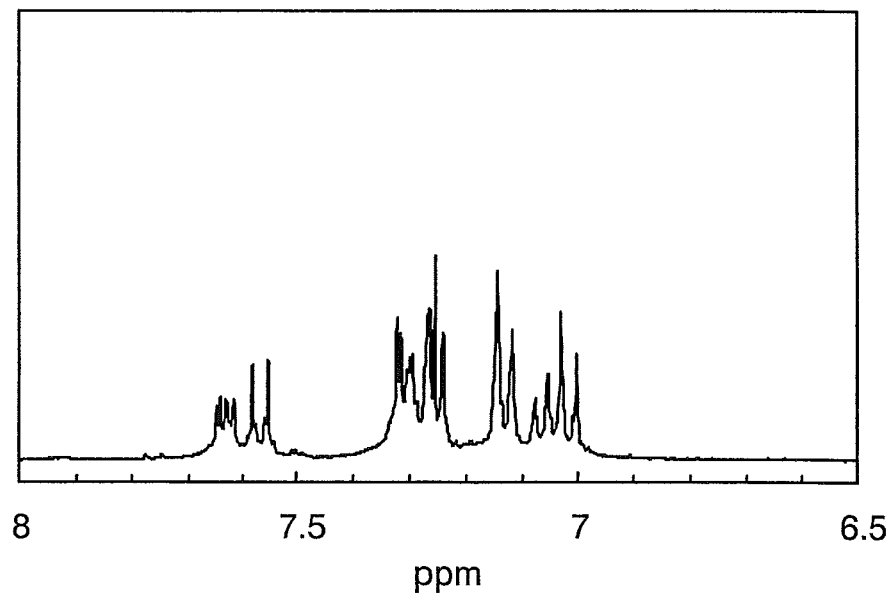

FIGS. 37A and 37B each show a $^1$H-NMR chart of DPhAPPPr. FIG. 37B is an enlarged chart of a range of 6.5 to 8.0 ppm of the chart of FIG. 37A.

Figure 38:
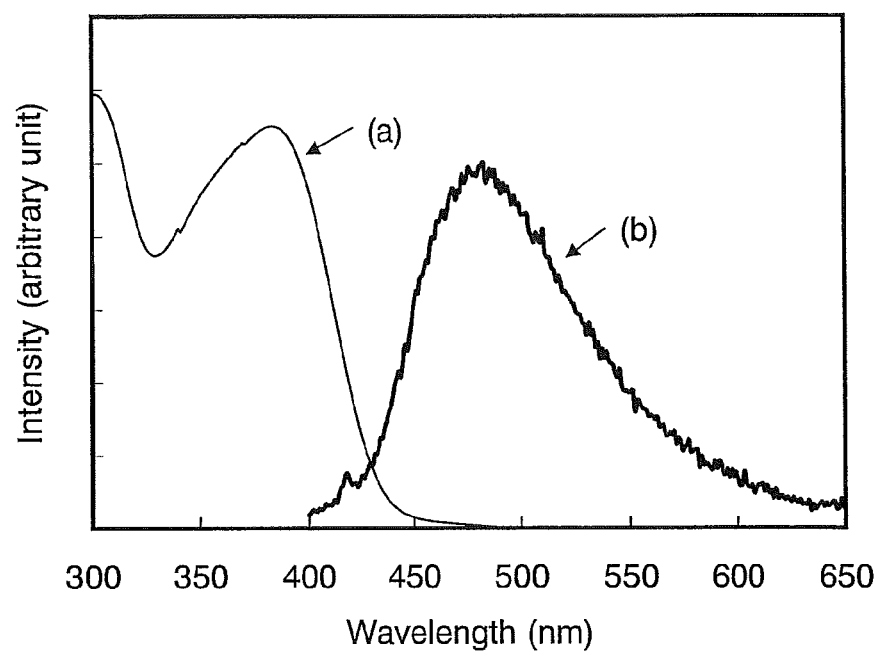
FIG. 38 is a graph showing an absorption spectrum and an emission spectrum in a state where DPhAPPPr is dissolved in a toluene solution.

FIG. 38 shows an absorption spectrum and an emission spectrum in a state where DPhAPPPr is dissolved in a toluene solution. The ultraviolet-visible spectrophotometer (V-550, manufactured by JASCO Corporation) was used for the measurement. In FIG. 38, the horizontal axis represents a wavelength (nm) and the vertical axis represents intensity (arbitrary unit). Further, in FIG. 38, a line (a) indicates the absorption spectrum whereas a line (b) indicates the emission spectrum (371 nm of an excited wavelength).

Embodiment 10

Synthesis Example 8

As one example of a pyrazine derivative of the present invention, a synthesis method of a compound represented by a structural formula (s-52), that is, 2,3-bis(4-{N-[4-(carbazole-9-yl)phenyl]-N-phenylamino}phenyl)-5,6-diphenylpyrazine (hereinafter, referred to as YGAPPPr), will be explained.

1.6 g (3.0 mmol) of PPPr, 2.0 g (6.0 mmol) of YGA, and 1.1 g (11 mmol) of sodium-tert-butoxide were put into a 100 mL three neck flask. After nitrogen was substituted for the content of the flask, 30 mL of toluene and 0.1 mL of a hexane solution (10 wt %) of tri-tert-butylphosphine were added thereto. Then, nitrogen was substituted for the content of the flask again, and 0.1 g (0.2 mmol) of bis(dibenzylideneacetone) palladium(0) were added. This mixture was heated and stirred for 5 hours at 80° C. to be reacted. After the reaction, toluene was added to the reaction mixture to dissolve the precipitated object, and the reaction mixture was subjected to suction and filtration through celite, florisil, and alumina. The filtrate was washed with water, dried with magnesium sulfate, and subjected to suction and filtration. A solid that was obtained by concentrating the filtrate was dissolved in toluene to be purified by silica column chromatography. For the column purification, first, a mixed solvent of toluene:hexane=1:1 was used as a developing solvent, and then toluene was used as a developing solvent. After the column purification, a solid that was extracted by concentrating the obtained solution was re-crystallized with chloroform and hexane, whereby 1.0 g of a yellow powder solid was obtained in the yield of 16% (Synthesis Scheme (m-1)).

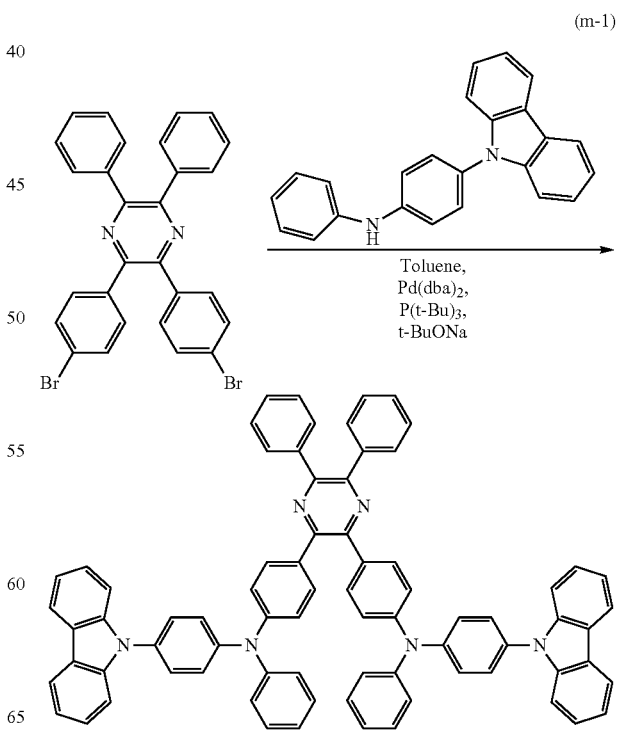

(m-1)

An analysis result by a proton nuclear magnetic resonance method ($^1$H-NMR) of YGAPPPr that was obtained is shown below. As a reference substance, TMS was used.

$^1$H-NMR (300 MHz, CDCl$_3$); δ=7.00-7.10 (m, 2H), δ=7.16 (d, J=8.8, 4H), δ=7.21-7.47 (m, 34H), δ=7.62-7.77 (m, 8H), δ=8.13 (d, J=7.3, 4H)

Figure 39A:
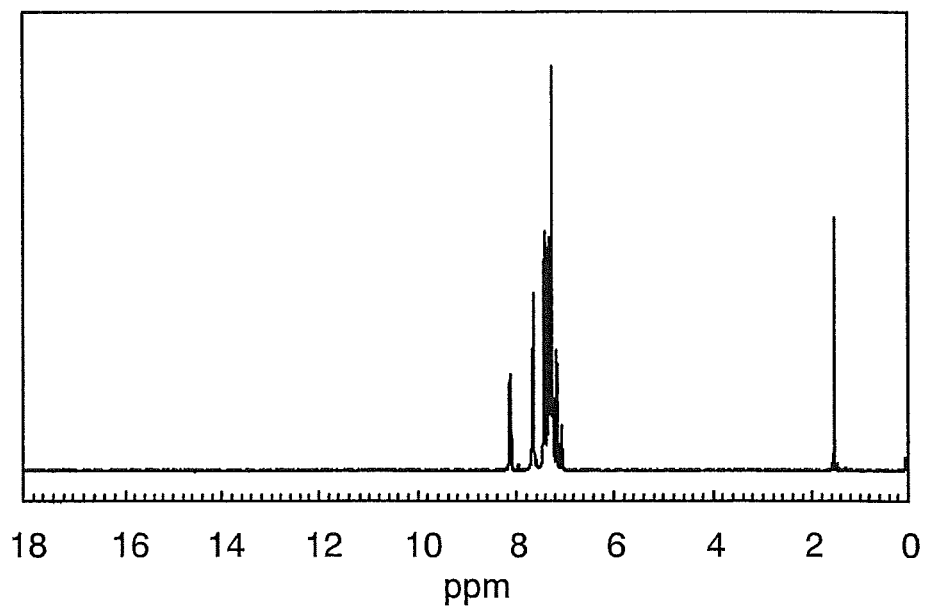
FIGS. 39A and 39B are $^1$H-NMR charts of YGAPPPr.
Figure 39B:
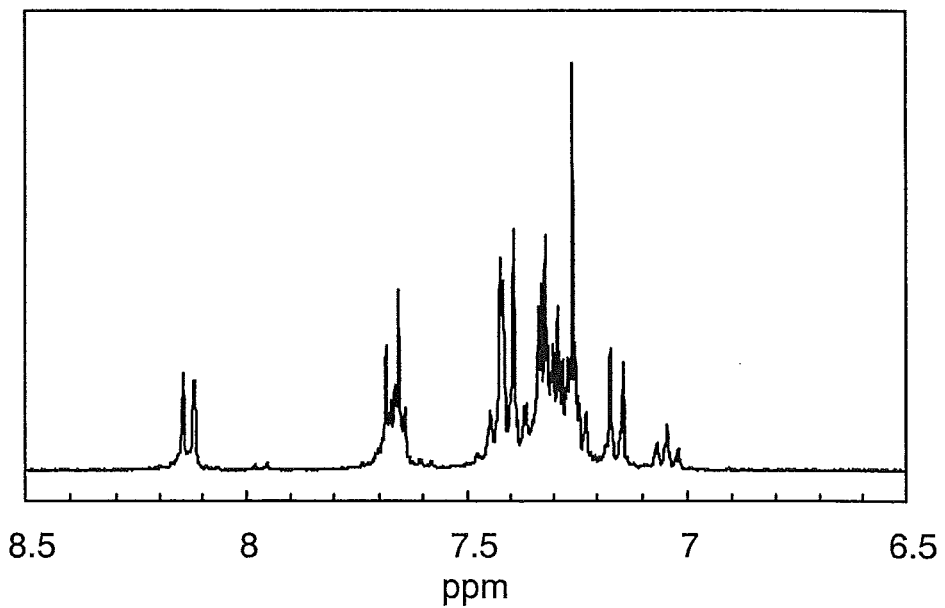

FIGS. 39A and 39B each show a $^1$H-NMR chart of YGA-PPPr. FIG. 39B is an enlarged chart of a range of 6.5 to 8.5 ppm of the chart of FIG. 39A.

Figure 40:
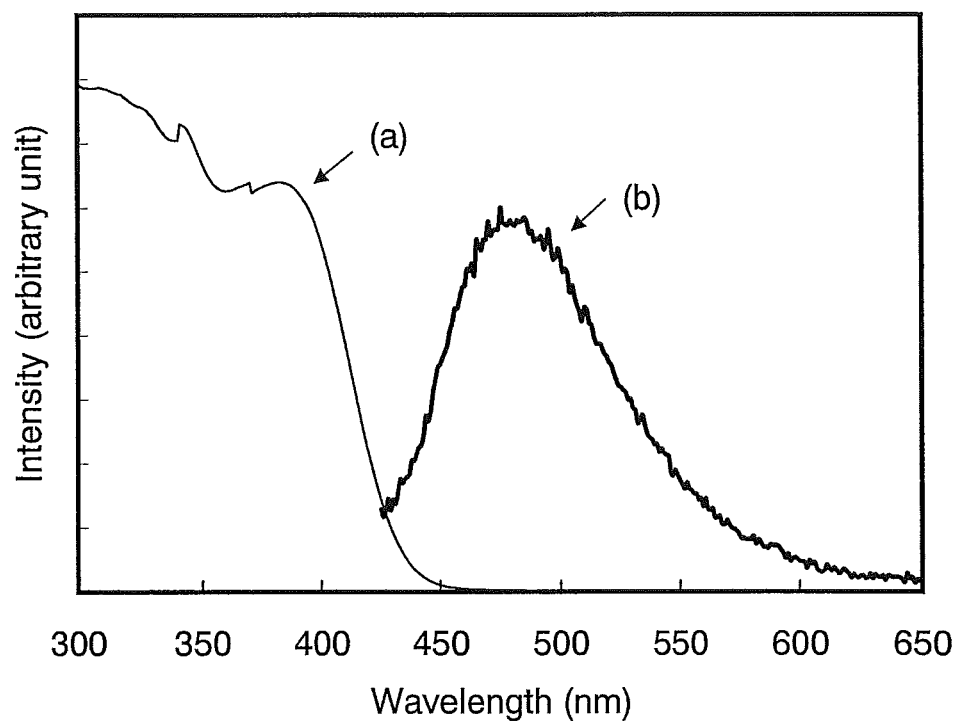
FIG. 40 is a graph showing an absorption spectrum and an emission spectrum in a state where YGAPPPr is dissolved in a toluene solution.

FIG. 40 shows an absorption spectrum and an emission spectrum in a state where YGAPPPr is dissolved in a toluene solution. The ultraviolet-visible spectrophotometer (V-550, manufactured by JASCO Corporation) was used for the measurement. In FIG. 40, the horizontal axis represents a wavelength (nm) and the vertical axis represents intensity (arbitrary unit). Further, in FIG. 40, a line (a) indicates the absorption spectrum whereas a line (b) indicates the emission spectrum (371 nm of an excited wavelength).

Embodiment 11

Figure 49:
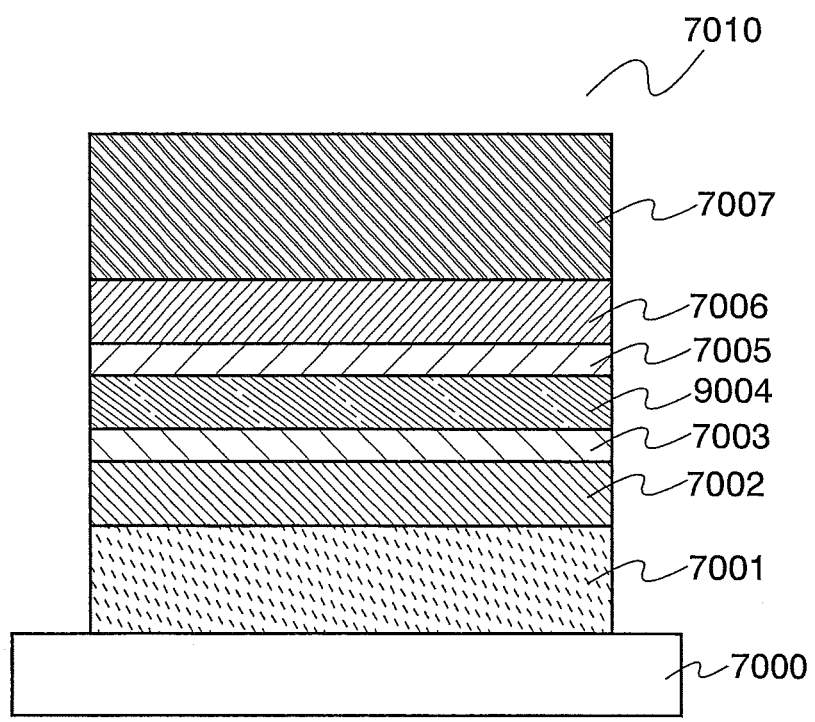
FIG. 49 is a view showing an example of a light emitting element of Embodiment 11.

In this embodiment, an example of a light emitting element will be specifically described, in which DPhAPPPr (the structural formula (s-14)) that is one example of a pyrazine derivative of the present invention synthesized in Synthesis Example 7 of Embodiment 9 is used as a host material of a light emitting layer, and a phosphorescent compound is used as a guest material. FIG. 49 shows an element structure. It is to be noted that the light emitting element except for a light emitting layer 9004 has the same structure as that of Embodiment 7; therefore, explanation thereof is omitted.

In this embodiment, the light emitting layer 9004 was formed by co-evaporating DPhAPPPr that is a pyrazine derivative (the structural formula (s-14)) and a phosphorescent compound represented by the above structural formula (s-117), that is, (acetylacetonato)bis[2,3-bis(4-fluorophenyl)quinoxalinato]iridium (III) (hereinafter, referred to as Ir(Fdpq)$_2$(acac)) so that a ratio thereof was set to be 1:0.07 in a mass ratio. The light emitting layer 9004 was formed to have a thickness of 30 nm. Accordingly, Ir(Fdpq)$_2$(acac) is dispersed in a layer made from DPhAPPPr (the structural formula (s-14)) that is a pyrazine derivative of the present invention. Other structures are the same as those of Embodiment 7.

Figure 41:
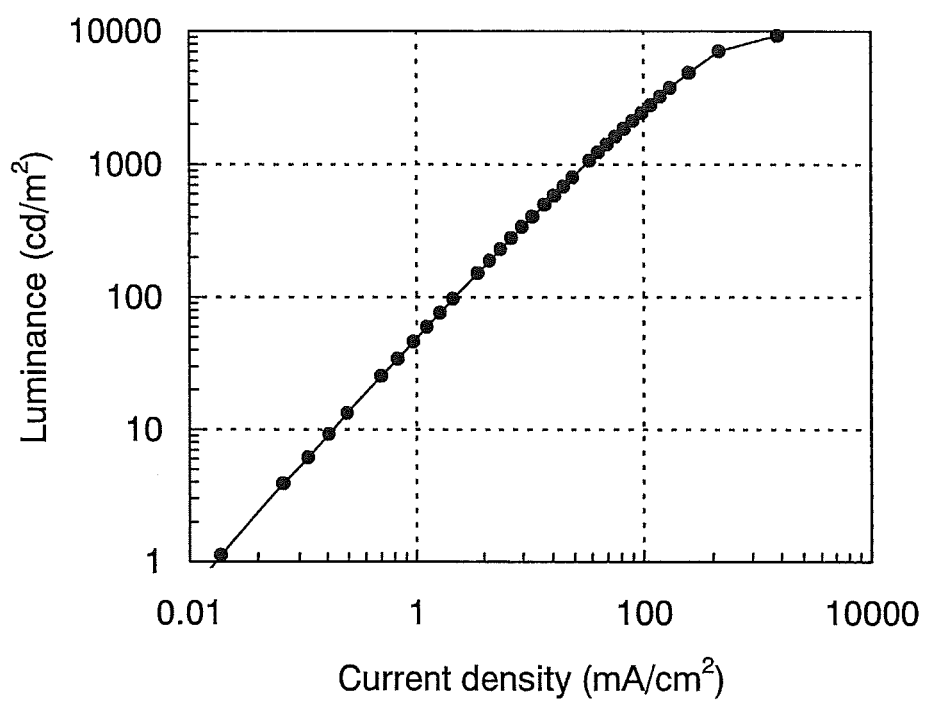
FIG. 41 is a graph showing a current density-luminance characteristic of a light emitting element of Embodiment 11.
Figure 42:
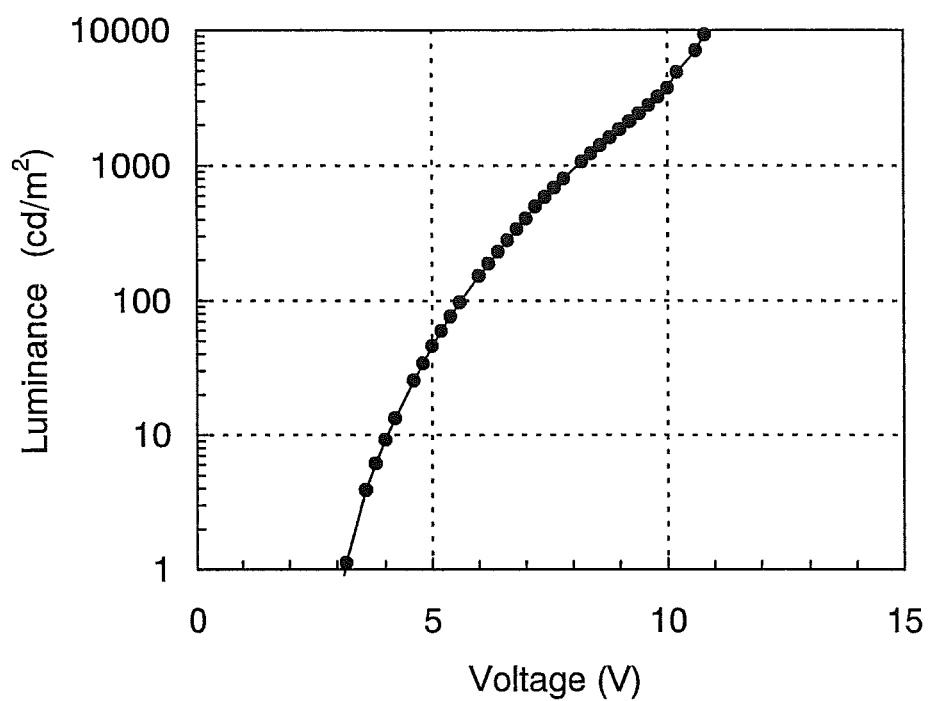
FIG. 42 is a graph showing a voltage-luminance characteristic of a light emitting element of Embodiment 11.
Figure 43:
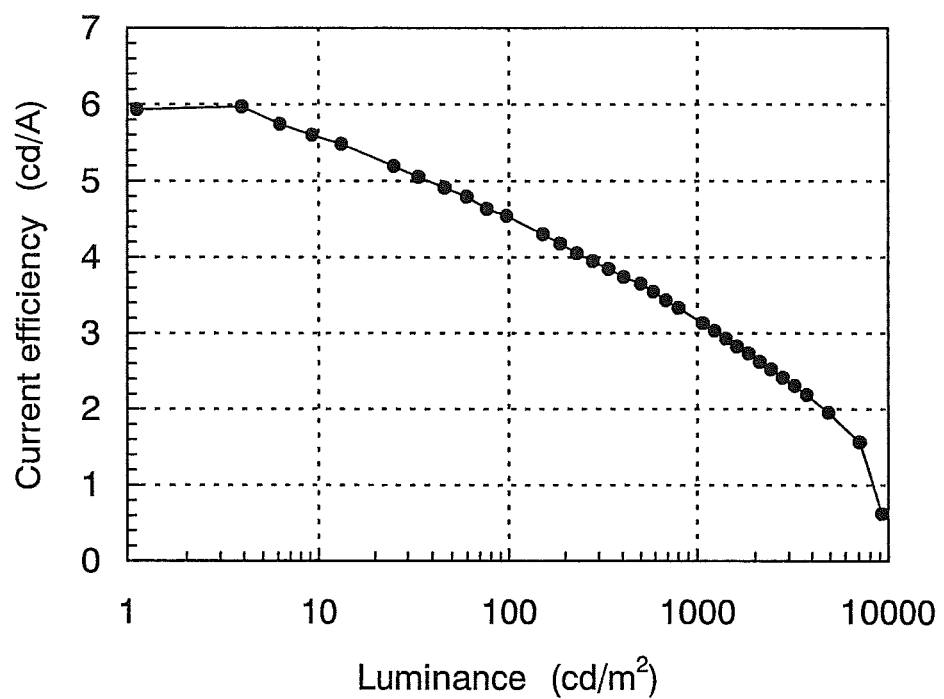
FIG. 43 is a graph showing a luminance-current efficiency characteristic of a light emitting element of Embodiment 11.
Figure 44:
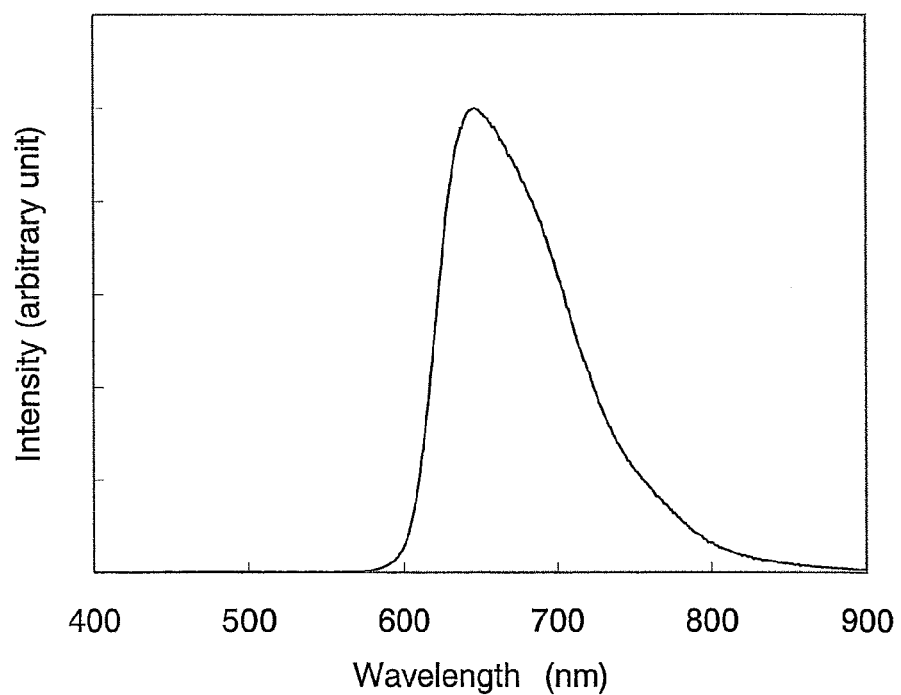
FIG. 44 is a graph showing an emission spectrum of a light emitting element of Embodiment 11.

FIG. 41 shows a current density-luminance characteristic of the light emitting element 9010 of this embodiment, and FIG. 42 shows a voltage-luminance characteristic thereof. FIG. 43 shows a luminance-current efficiency characteristic thereof, and FIG. 44 shows an emission spectrum. In the light emitting element 7010 of this embodiment, by applying a voltage of 8.2 V, a current flowed with the current density of 34.1 mA/cm$^2$, and light was emitted with the luminance of 1100 cd/m$^2$. The current efficiency at this time was 3.1 cd/A. The emission spectrum has a peak in 647 nm, and light emission with a red color that is derived from Ir(Fdpq)$_2$(acac) of a guest material was obtained. The CIE chromaticity coordinate at 1100 cd/m$^2$ was (x=0.71, y=0.29), and light emission with a deep red color having high color purity was exhibited.

According to the above, a light emitting element is manufactured by using a pyrazine derivative of the present invention as a host material of a light emitting layer and a phosphorescent compound as a guest material, whereby it was found that a light emitting element having extremely high light emitting efficiency can be obtained.

Embodiment 12

Figure 50:
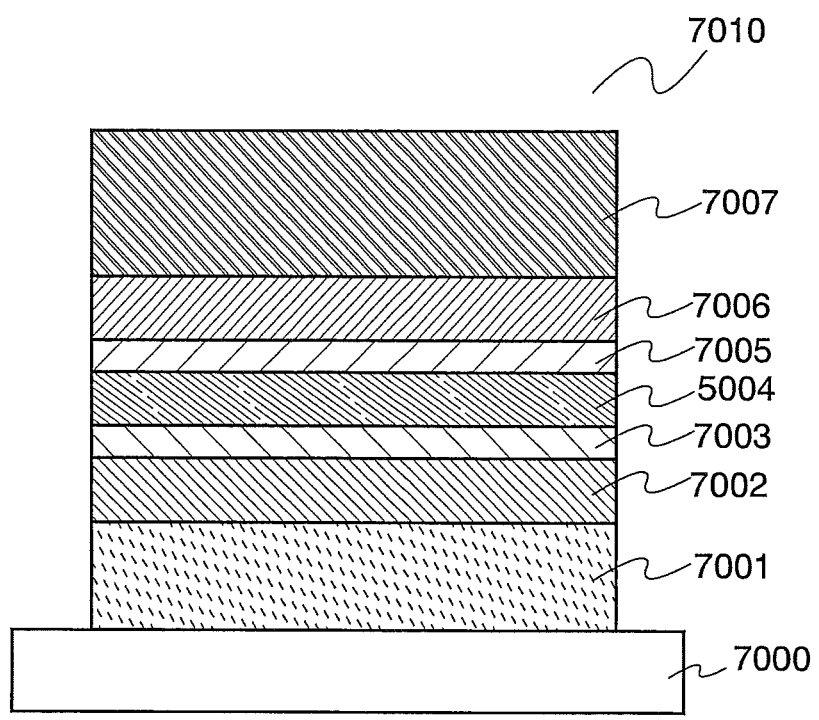
FIG. 50 is a view showing an example of a light emitting element of Embodiment 12.

In this embodiment, an example of a light emitting element will be specifically described, in which YGAPPPr (the structural formula (s-52)) that is one example of a pyrazine derivative of the present invention synthesized by Synthesis Example 8 of Embodiment 10 is used as a host material of a light emitting layer, and a phosphorescent compound is used as a guest material. FIG. 50 shows an element structure. It is to be noted that the light emitting layer except for a light emitting layer 5004 has the same structure as that of Embodiment 7; therefore, explanation thereof is omitted.

In this embodiment, the light emitting layer 5004 was formed by co-evaporating YGAPPPr (the structural formula (s-52)) that is a pyrazine derivative and a phosphorescent compound represented by the above structural formula (s-117), that is, (acetylacetonato)bis[2,3-bis(4-fluorophenyl)quinoxalinato]iridium(III) (hereinafter, referred to as Ir(Fdpq)$_2$(acac)) so that a ratio thereof was set to be 1:0.07 in a mass ratio. The light emitting layer 5004 was formed to have a thickness of 30 nm. Accordingly, Ir(Fdpq)$_2$(acac) is dispersed in a layer made from YGAPPPr (the structural formula (s-52)) that is a pyrazine derivative of the present invention. Other structures are the same as those of Embodiment 7.

Figure 45:
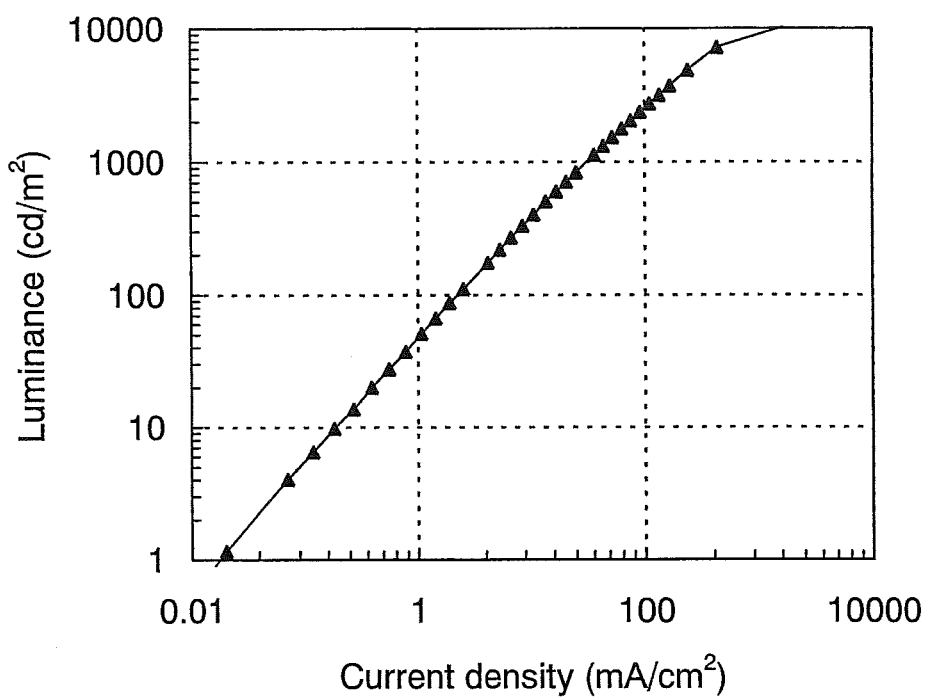
FIG. 45 is a graph showing a current density-luminance characteristic of a light emitting element of Embodiment 12.
Figure 46:
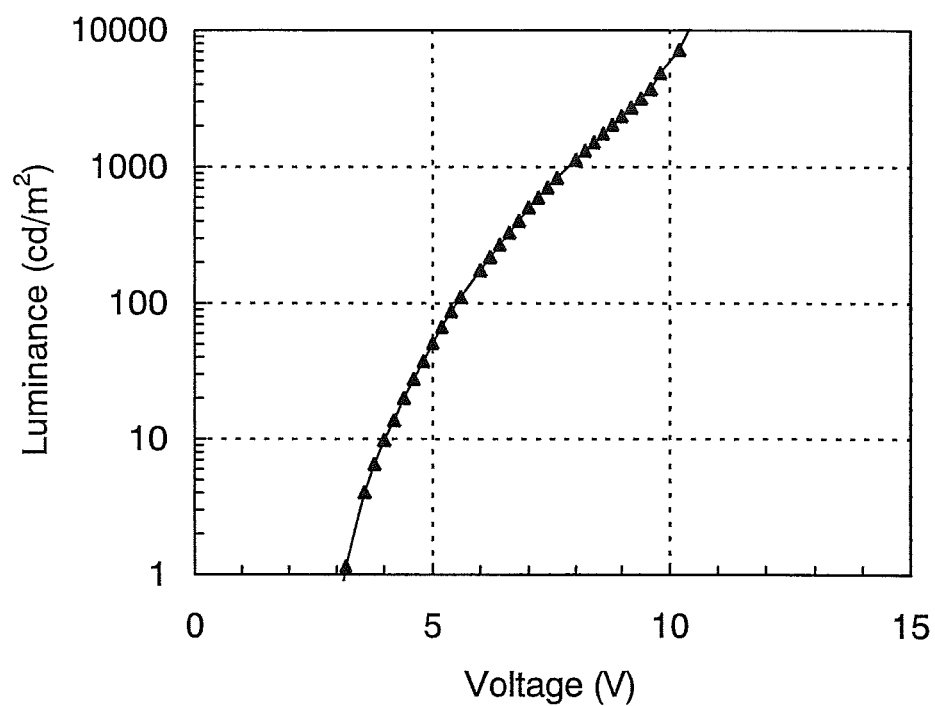
FIG. 46 is a graph showing a voltage-luminance characteristic of a light emitting element of Embodiment 12.
Figure 47:
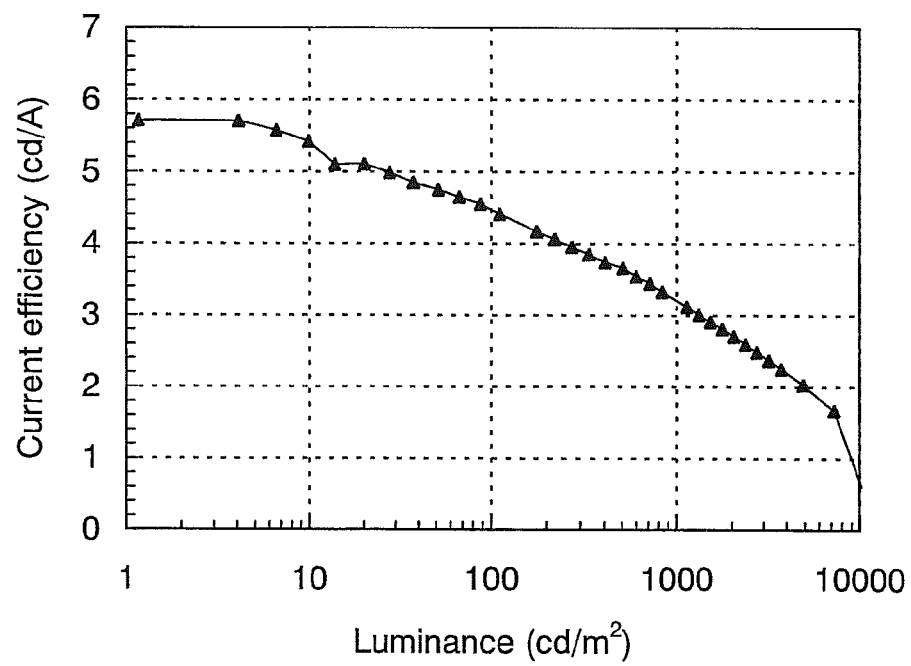
FIG. 47 is a graph showing a luminance-current efficiency characteristic of a light emitting element of Embodiment 12.
Figure 48:
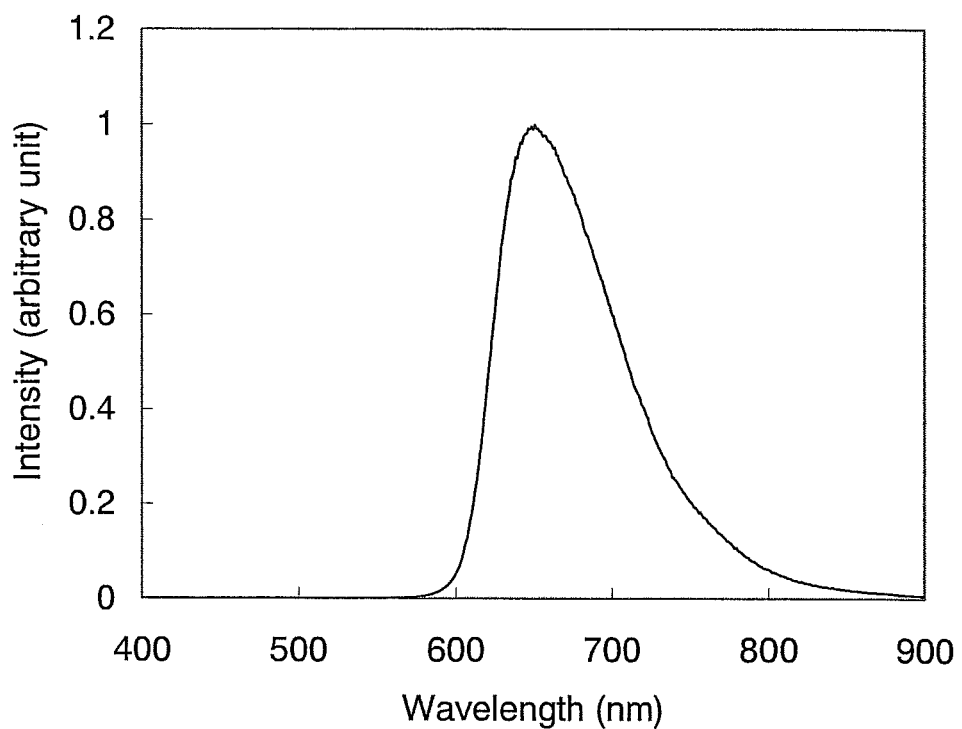
FIG. 48 is a graph showing an emission spectrum of a light emitting element of Embodiment 12.

FIG. 45 shows a current density-luminance characteristic of a light emitting element 7010 of this embodiment, and FIG. 46 shows a voltage-luminance characteristic thereof. FIG. 47 shows a luminance-current efficiency characteristic thereof, and FIG. 48 shows an emission spectrum. In the light emitting element 5010 of this embodiment, by applying a voltage of 8.0 V, a current flowed with the current density of 36.4 mA/cm$^2$, and light was emitted with the luminance of 1100 cd/m$^2$. The current efficiency at this time was 3.1 cd/A. The emission spectrum has a peak in 650 nm, and light emission with a red color that is derived from Ir(Fdpq)$_2$(acac) of a guest material was obtained. The CIE chromaticity coordinate at 1100 cd/m$^2$ was (x=0.71, y=0.29), and light emission with a deep red color having extremely high color purity was exhibited.

According to the above, a light emitting element is manufactured by using a pyrazine derivative of the present invention as a host material of a light emitting layer and a phosphorescent compound as a guest material, whereby it was found that a light emitting element having extremely high light emitting efficiency can be obtained.

Embodiment 13

Synthesis Example 10

As one example of a pyrazine derivative of the present invention, a synthesis method of a compound represented by a structural formula (s-88), that is, 2-(4-{N-[4-(carbazole-9-yl)phenyl]-N-phenylamino}phenyl)-3,5,6-triphenylpyrazine (hereinafter, referred to as YGAlPPPr), will be explained.

Step 1: Synthesis method of 2-(4-bromophenyl)-3,5,6-triphenylpyrazine (hereinafter, referred to as 1PPPr)

(1) Synthesis of 1-(4-bromophenyl)-2-phenylacetylene 28.3 g (0.10 mol) of p-bromoiodebenzene, 10.2 g (0.10 ml) of phenylacetylene, 0.70 g (1.0 mmol) of bis(triphenylphosphine)palladium(II)dichloride, and 0.19 g (1.0 mmol) of copper iodide (I) were put into a 1000 mL three neck flask, and nitrogen was substituted for the content of the flask. Then, 350 mL of tetrahydrofuran and 18 mL of trietylamine were added thereto, and this mixture was stirred for 20 hours at the room temperature to be reacted. After the reaction, the reaction solution was washed with a 3 wt % hydrochloride acid solution, an organic layer and an aqueous layer were separated. After the aqueous layer was extracted by ethyl acetate, the extract combined with the organic layer was washed with a sodium carbonate solution and saturated saline, in that order. Then, the organic layer was dried with magnesium sulfate. The mixture of the organic layer and magnesium sulfate was filtered through celite, florisil, and alumina. A solid that was obtained by concentrating the filtrate was washed with hexane, whereby 19 g of a solid of 1-(4-bromophenyl)-2-phenylacetylene that is an object was obtained in the yield of 74% (Synthesis Scheme (n-1)).

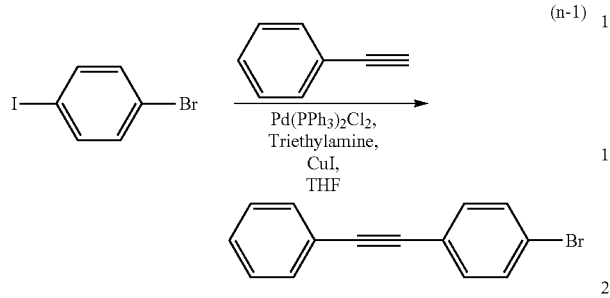

(2) Synthesis of 4-bromobenzyle 19 g (74 mmol) of 1-(4-bromophenyl)-2-phenylacetylene, 9.4 g (37 mmol) of iodine, and 200 mL of dimethyl sulfoxide were put into a 500 mL three neck flask and stirred for 4 hours at 155° C. to be reacted. After the reaction, the reaction mixture was cooled, and then, a 3 wt % sodium thiosulfate solution was added thereto. This mixture was stirred for 1 hour at the room temperature. Ethyl acetate was added to this mixture, and the mixture was washed with 1N diluted hydrochloric acid, a sodium hydrogen carbonate solution, and saturated saline to separate an organic layer and an aqueous layer. The organic layer was dried with magnesium sulfate, and the mixture of the organic layer and magnesium sulfate was filtered. A solid that was obtained by concentrating the filtrate was washed with hexane that was cooled with ice, whereby 15 g of a solid of 4-bromobenzyl that is an object was obtained in the yield of 58% (Synthesis Scheme (n-2)).

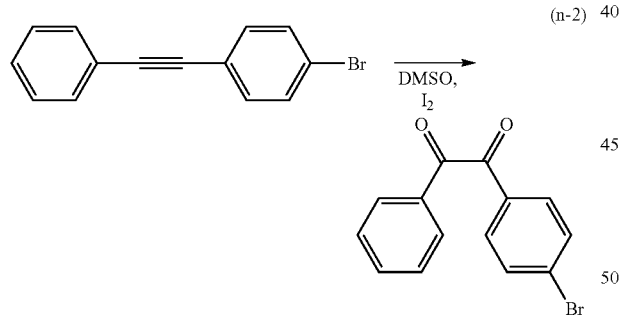

(3) Synthesis of 1PPPr 3.0 g (1.0 mmol) of 4-bromobenzyl and 2.2 g (1.0 mmol) of meso-diphenylethylendiamine were put into a 500 mL three neck flask, and 100 mL of ethanol was added thereto. This mixture was heated and stirred for 5 hours at 80° C. to be reacted. After the reaction, the reaction solution was concentrated, and 1.1 g of manganese dioxide and 100 mL of chloroform were added thereto. Then, the reaction solution was further heated and stirred for 1 hour at 80° C. to be reacted. Thereafter, water was added to the reaction solution and washed, and an organic layer and an aqueous layer were separated. The organic layer was filtered through celite, and the filtrate was concentrated. Then, an obtained object was re-crystallized with a mixed solvent of chloroform and hexane, whereby 2.1 g of a light brown powder solid of 1PPPr that is an object was obtained in the yield of 45% (Synthesis Scheme (n-3)).

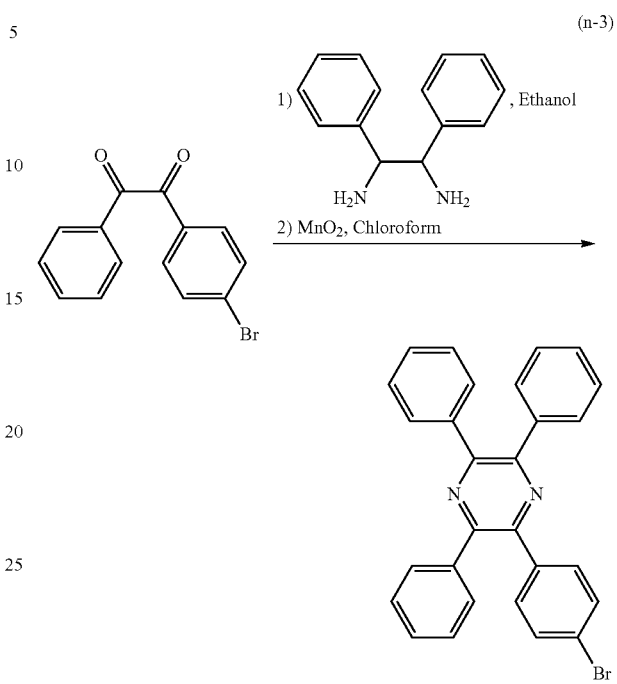

Step 2: Synthesis Method of YGAlPPPr

1PPPr (2.2 mmol), 0.72 g (2.2 mmol) of YGA, and 0.3 g (3.1 mmol) of sodium-tert-butoxide were put into a 100 mL three neck flask. After nitrogen was substituted for the content of the flask, 20 mL of toluene and 0.10 mL of a hexane solution (10 wt %) of tri-tert-butylphosphine were added. Then, nitrogen was substituted for the content of the flask again, and 0.10 g (0.2 mmol) of bis(dibenzylideneacetone)palladium(0) were added thereto. This mixture was heated and stirred for 5 hours at 80° C. to be reacted. After the reaction, toluene was added to the reaction mixture and filtered through celite, florisil, and alumina. After the filtrate was washed with water, an organic layer and an aqueous layer were separated, the organic layer was dried with magnesium sulfate, and filtration was performed. A solid that was obtained by concentrating the filtrate was re-crystallized with a mixed solvent of chloroform and hexane, whereby 0.90 g of a light yellow powder solid of YGAlPPPr that is an object was obtained in the yield of 58% (Synthesis Scheme (n-4)).

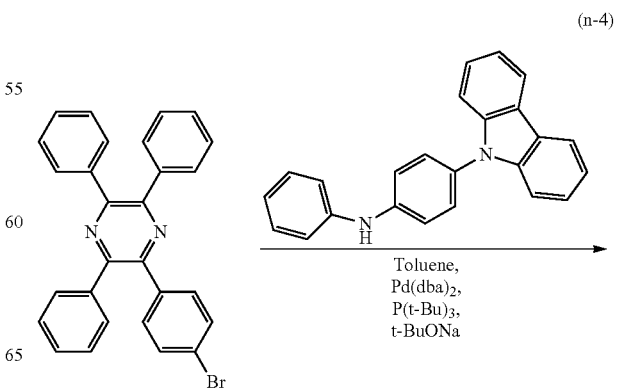

-continued

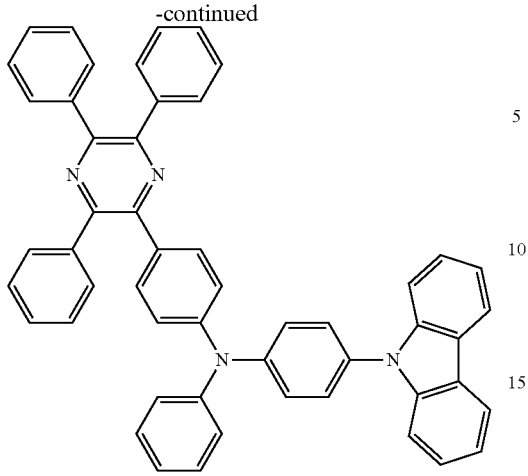

An analysis result by a proton nuclear magnetic resonance method ($^1$H-NMR) of YGAPPPr is shown below. As a reference substance, TMS was used.

$^1$H-NMR (300 MHz, CDCl$_3$); δ=7.07-7.17 (m, 3H), δ=7.19-7.51 (m, 23H), δ=7.53-7.82 (m, 8H), δ=8.14 (d, J=7.3, 2H)

Figure 51A:
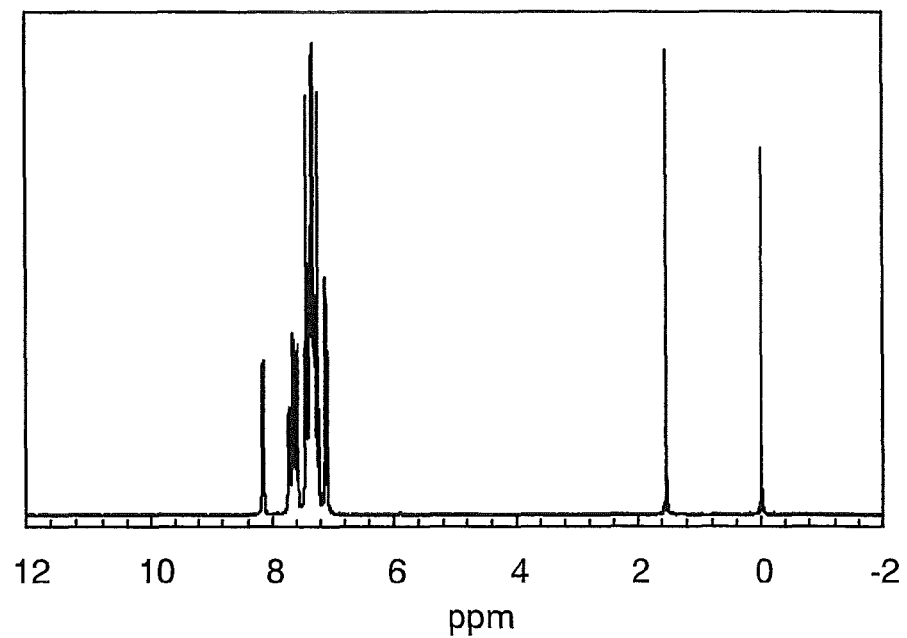
FIGS. 51A and 51B are $^1$H-NMR charts of YGAlPPPr.
Figure 51B:
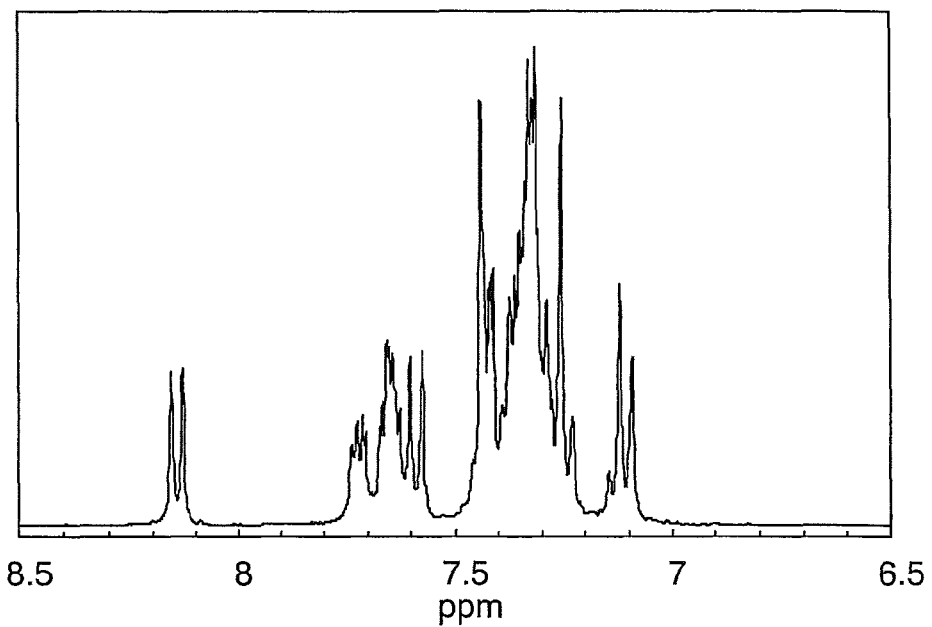

FIGS. 51A and 51B each show a $^1$H-NMR chart of YGA-lPPPr. FIG. 51B is an enlarged chart of a range of 6.5 to 8.5 ppm of the chart of FIG. 51A.

Figure 52:
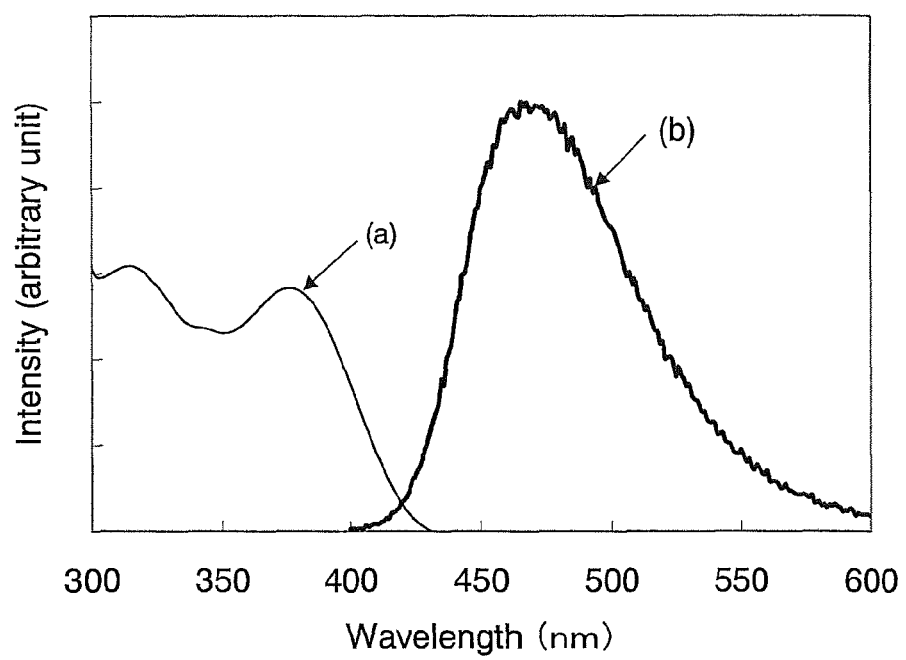
FIG. 52 is a graph showing an absorption spectrum and an emission spectrum in a state where YGAlPPPr is dissolved in a toluene solution.

FIG. 52 shows an absorption spectrum and an emission spectrum in a state where YGAlPPPr is dissolved in a toluene solution. The ultraviolet-visible spectrophotometer (V-550, manufactured by JASCO Corporation) was used for the measurement. In FIG. 52, the horizontal axis represents a wavelength (nm) and the vertical axis represents intensity (arbitrary unit). Further, in FIG. 52, a line (a) indicates the absorption spectrum whereas a line (b) indicates the emission spectrum (376 nm of an excited wavelength).

This application is based on Japanese Patent Application serial no. 2005-378811 filed in Japan Patent Office on Dec. 28, 2005, the entire contents of which are hereby incorporated by reference.

What is claimed is:

1. A compound represented by the formula (1)

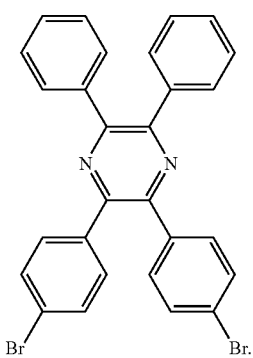

(1)

2. A compound represented by the formula (2)

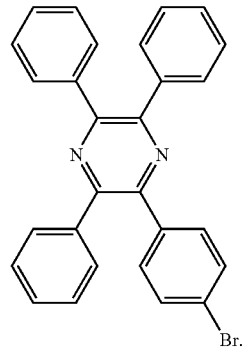

(2)

3. A method comprising making a reaction of a first compound with a second compound,
wherein the first compound is represented by the formula (1) or (2),

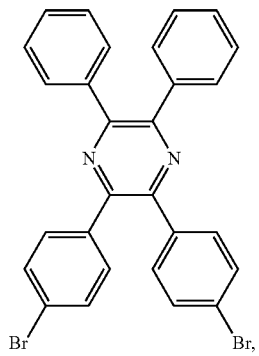

(1)

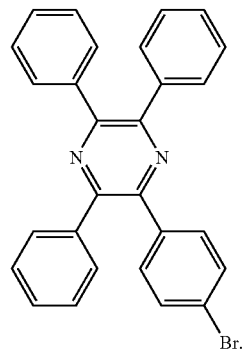

(2)

4. The method according to claim 3, wherein the first compound is represented by the formula (2).

5. The method according to claim 3, wherein the second compound is a secondary amine compound.

6. The method according to claim 3, wherein the reaction is accelerated by a palladium catalyst or a copper catalyst.

7. The method according to claim 6, wherein the palladium catalyst is one selected from the group consisting of palladium acetate, palladium chloride (II), and bis(dibenzylideneacetone)palladium(0).

8. The method according to claim 3, the reaction is performed in the presence of a base.

* * * * *